United States Patent
Bowe et al.

(10) Patent No.: US 10,368,900 B2
(45) Date of Patent: *Aug. 6, 2019

(54) TISSUE SLITTING METHODS AND SYSTEMS

(71) Applicant: The Spectranetics Corporation, Colorado Springs, CO (US)

(72) Inventors: Wade A. Bowe, Colorado Springs, CO (US); George Woodrow Burton, Colorado Springs, CO (US); Paul Joseph Dalby, Colorado Springs, CO (US); Ryan Michael Sotak, Colorado Springs, CO (US); Matthew Allan James, Divide, CO (US)

(73) Assignee: THE SPECTRANETICS CORPORATION, Colorado Springs, CO (US)

( * ) Notice: Subject to any disclaimer, the term of this patent is extended or adjusted under 35 U.S.C. 154(b) by 260 days.

This patent is subject to a terminal disclaimer.

(21) Appl. No.: 15/229,873

(22) Filed: Aug. 5, 2016

(65) Prior Publication Data

US 2016/0338727 A1    Nov. 24, 2016

Related U.S. Application Data

(63) Continuation of application No. 13/828,310, filed on Mar. 14, 2013, now Pat. No. 9,413,896.

(Continued)

(51) Int. Cl.
*A61B 17/3207* (2006.01)
*A61N 1/05* (2006.01)
(Continued)

(52) U.S. Cl.
CPC .... *A61B 17/32075* (2013.01); *A61B 17/3203* (2013.01); *A61B 17/3207* (2013.01);
(Continued)

(58) Field of Classification Search
CPC ............ A61B 17/32; A61B 17/320016; A61B 17/32002; A61B 17/3205; A61B 17/3207;
(Continued)

(56) References Cited

U.S. PATENT DOCUMENTS 1,663,761 A * 3/1928 Johnson ......... A61B 17/320783
30/240
3,400,708 A 9/1968 Scheidt
(Continued)

FOREIGN PATENT DOCUMENTS

DE 4038773 A1 6/1992
JP H05506382 A 9/1993
(Continued)

OTHER PUBLICATIONS

Decision to Grant for European Patent Application No. 07255018.9, dated Aug. 8, 2013, 2 pages.
(Continued)

*Primary Examiner* — Ryan J. Severson

(57) ABSTRACT

Methods and systems for separating an object, such as a lead, from formed tissue are provided. Specifically, a tissue slitting device is configured to engage patient formed tissue at a slitting engagement point. While the object is subjected to a first traction force, the tissue slitting device is caused to move further into the engaged tissue and slit the tissue past the point of engagement. The slitting device causes the tissue to separate along an axial direction of the length of the formed tissue and releases at least some of the force containing the object. The methods and systems are well suited for use in cardiac pacing or defibrillator lead explant procedures.

13 Claims, 19 Drawing Sheets

Related U.S. Application Data

(60) Provisional application No. 61/701,521, filed on Sep. 14, 2012.

(51) Int. Cl.

| | |
|---|---|
| *A61B 90/00* | (2016.01) |
| *A61B 17/3203* | (2006.01) |
| *A61B 17/3211* | (2006.01) |
| *A61B 17/50* | (2006.01) |
| *A61B 18/24* | (2006.01) |
| *G10L 21/00* | (2013.01) |
| *H04L 29/06* | (2006.01) |
| *H04M 3/56* | (2006.01) |
| *A61B 17/32* | (2006.01) |

(52) U.S. Cl.
CPC .... *A61B 17/3211* (2013.01); *A61B 17/32037* (2013.01); *A61B 17/320725* (2013.01); *A61B 17/50* (2013.01); *A61B 18/245* (2013.01); *A61B 90/02* (2016.02); *A61N 1/05* (2013.01); *A61N 1/056* (2013.01); *A61N 1/057* (2013.01); *G10L 21/00* (2013.01); *H04L 65/403* (2013.01); *H04M 3/568* (2013.01); *A61B 2017/320004* (2013.01); *A61B 2017/320044* (2013.01); *A61N 2001/0578* (2013.01); *F04C 2270/041* (2013.01)

(58) Field of Classification Search
CPC ...... A61B 17/32075; A61B 17/320783; A61B 17/50; A61B 2017/320004; A61B 2017/320024; A61B 2017/320028; A61B 2017/320032; A61B 2017/320741
See application file for complete search history.

(56) References Cited

U.S. PATENT DOCUMENTS

| | | |
|---|---|---|
| 3,521,640 A | 7/1970 | Carey et al. |
| 3,614,953 A | 10/1971 | Moss |
| 3,805,382 A | 4/1974 | Benedict |
| 3,831,274 A | 8/1974 | Horrocks |
| 3,858,577 A | 1/1975 | Bass et al. |
| 4,051,596 A | 10/1977 | Hofmann |
| 4,203,444 A | 5/1980 | Bonnell et al. |
| 4,246,902 A | 1/1981 | Martinez |
| 4,274,414 A | 6/1981 | Johnson et al. |
| 4,311,138 A | 1/1982 | Sugarman |
| 4,471,777 A | 9/1984 | McCorkle, Jr. |
| 4,517,977 A | 5/1985 | Frost |
| 4,559,927 A | 12/1985 | Chin |
| 4,566,438 A | 1/1986 | Liese et al. |
| 4,567,882 A | 2/1986 | Heller |
| 4,576,162 A | 3/1986 | McCorkle |
| 4,582,056 A | 4/1986 | McCorkle et al. |
| 4,598,710 A | 7/1986 | Kleinberg et al. |
| 4,627,436 A | 12/1986 | Leckrone |
| 4,641,912 A | 2/1987 | Goldenberg |
| 4,646,738 A | 3/1987 | Trott |
| 4,662,869 A | 5/1987 | Wright |
| 4,674,502 A | 6/1987 | Imonti |
| 4,718,417 A | 1/1988 | Kittrell et al. |
| 4,729,763 A | 3/1988 | Henrie |
| 4,754,755 A | 7/1988 | Husted |
| 4,767,403 A | 8/1988 | Hodge |
| 4,842,578 A * | 6/1989 | Johnson ............ A61B 17/1659 604/22 |
| 4,844,062 A | 7/1989 | Wells |
| 4,862,886 A | 9/1989 | Clarke et al. |
| 4,911,148 A | 3/1990 | Sosnowski et al. |
| 4,943,289 A | 7/1990 | Goode et al. |
| 4,988,347 A | 1/1991 | Goode et al. |
| 4,997,424 A | 3/1991 | Little |
| 5,011,482 A | 4/1991 | Goode et al. |
| 5,013,310 A | 5/1991 | Goode et al. |
| 5,030,207 A | 7/1991 | Mersch et al. |
| 5,031,634 A | 7/1991 | Simon |
| 5,041,108 A | 8/1991 | Fox et al. |
| 5,114,403 A | 5/1992 | Clarke et al. |
| 5,129,897 A | 7/1992 | Daikuzono |
| 5,139,494 A | 8/1992 | Freiberg |
| 5,139,495 A | 8/1992 | Daikuzono |
| 5,148,599 A | 9/1992 | Purcell |
| 5,152,744 A | 10/1992 | Krause et al. |
| 5,186,634 A | 2/1993 | Thompson |
| 5,201,316 A | 4/1993 | Pomeranz et al. |
| 5,207,683 A | 5/1993 | Goode et al. |
| 5,230,334 A | 7/1993 | Klopotek |
| 5,250,045 A | 10/1993 | Bohley |
| 5,263,928 A | 11/1993 | Trauthen et al. |
| 5,275,609 A | 1/1994 | Pingleton et al. |
| 5,290,275 A | 3/1994 | Kittrell et al. |
| 5,290,280 A | 3/1994 | Daikuzono |
| 5,290,303 A | 3/1994 | Pingleton et al. |
| 5,353,786 A | 10/1994 | Wilk |
| 5,358,487 A | 10/1994 | Miller |
| 5,373,840 A | 12/1994 | Knighton |
| 5,377,683 A | 1/1995 | Barken |
| 5,383,199 A | 1/1995 | Laudenslager et al. |
| 5,395,328 A | 3/1995 | Ockuly et al. |
| 5,396,902 A | 3/1995 | Brennen et al. |
| 5,423,330 A | 6/1995 | Lee |
| 5,456,680 A | 10/1995 | Taylor et al. |
| 5,460,182 A | 10/1995 | Goodman et al. |
| 5,466,234 A | 11/1995 | Loeb et al. |
| 5,468,238 A | 11/1995 | Mersch |
| 5,470,330 A | 11/1995 | Goldenberg et al. |
| 5,484,433 A | 1/1996 | Taylor et al. |
| 5,489,291 A * | 2/1996 | Wiley ............... A61B 17/32002 604/22 |
| 5,507,751 A | 4/1996 | Goode et al. |
| 5,522,795 A * | 6/1996 | Green .................... A61B 10/04 604/1 |
| 5,562,694 A | 10/1996 | Sauer et al. |
| 5,569,284 A | 10/1996 | Young et al. |
| 5,573,531 A | 11/1996 | Gregory |
| 5,575,797 A | 11/1996 | Neubauer et al. |
| 5,605,539 A | 2/1997 | Buelna et al. |
| 5,620,451 A | 4/1997 | Rosborough |
| 5,632,749 A | 5/1997 | Goode et al. |
| 5,651,781 A | 7/1997 | Grace |
| 5,665,051 A | 9/1997 | Quick et al. |
| 5,667,473 A | 9/1997 | Finn et al. |
| 5,674,217 A | 10/1997 | Walstrom |
| 5,682,199 A | 10/1997 | Lankford |
| 5,697,936 A | 12/1997 | Shipko et al. |
| 5,700,270 A | 12/1997 | Peyser et al. |
| 5,707,389 A | 1/1998 | Louw et al. |
| 5,718,237 A | 2/1998 | Haaga |
| 5,725,523 A | 3/1998 | Mueller |
| 5,735,847 A | 4/1998 | Gough et al. |
| 5,746,738 A | 5/1998 | Cleary et al. |
| 5,759,185 A * | 6/1998 | Grinberg ............ A61B 17/1615 606/180 |
| 5,766,164 A | 6/1998 | Mueller et al. |
| 5,782,823 A | 7/1998 | Mueller |
| 5,807,399 A | 9/1998 | Laske et al. |
| 5,814,044 A | 9/1998 | Hooven |
| 5,823,971 A | 10/1998 | Robinson et al. |
| 5,824,026 A | 10/1998 | Diaz |
| 5,825,958 A | 10/1998 | Gollihar et al. |
| 5,863,294 A | 1/1999 | Alden |
| 5,873,886 A | 2/1999 | Larsen et al. |
| 5,879,365 A | 3/1999 | Whitfield et al. |
| 5,893,862 A | 4/1999 | Pratt et al. |
| 5,899,915 A | 5/1999 | Saadat |
| 5,906,611 A | 5/1999 | Dodick et al. |
| 5,910,150 A | 6/1999 | Saadat |
| 5,916,210 A | 6/1999 | Winston |
| 5,931,848 A | 8/1999 | Saadat |
| 5,941,893 A | 8/1999 | Saadat |
| 5,947,958 A | 9/1999 | Woodard et al. |

(56) References Cited

U.S. PATENT DOCUMENTS

| | | |
|---|---|---|
| 5,951,543 A | 9/1999 | Brauer |
| 5,951,581 A | 9/1999 | Saadat et al. |
| 5,970,982 A | 10/1999 | Perkins |
| 5,972,012 A | 10/1999 | Ream et al. |
| 5,980,515 A | 11/1999 | Tu |
| 5,980,545 A | 11/1999 | Pacala et al. |
| 5,989,243 A | 11/1999 | Goldenberg |
| 6,007,512 A | 12/1999 | Hooven |
| 6,010,476 A | 1/2000 | Saadat |
| 6,019,756 A | 2/2000 | Mueller et al. |
| 6,022,336 A | 2/2000 | Zadno-Azizi et al. |
| 6,027,450 A | 2/2000 | Brown et al. |
| 6,027,497 A | 2/2000 | Daniel et al. |
| 6,033,402 A | 3/2000 | Tu et al. |
| 6,036,685 A | 3/2000 | Mueller |
| 6,051,008 A | 4/2000 | Saadat et al. |
| 6,053,923 A * | 4/2000 | Veca ............... A61B 17/32002 606/79 |
| 6,066,131 A | 5/2000 | Mueller et al. |
| 6,080,175 A | 6/2000 | Hogendijk |
| 6,083,237 A | 7/2000 | Huitema et al. |
| 6,099,537 A | 8/2000 | Sugai et al. |
| 6,102,926 A | 8/2000 | Tartaglia et al. |
| 6,117,128 A | 9/2000 | Gregory |
| 6,120,520 A | 9/2000 | Saadat et al. |
| 6,123,718 A | 9/2000 | Tu et al. |
| 6,126,654 A | 10/2000 | Giba et al. |
| 6,136,005 A | 10/2000 | Goode et al. |
| 6,139,543 A | 10/2000 | Esch et al. |
| 6,152,909 A | 11/2000 | Bagaoisan et al. |
| 6,152,918 A | 11/2000 | Padilla et al. |
| 6,156,049 A | 12/2000 | Lovato et al. |
| 6,159,203 A | 12/2000 | Sinofsky |
| 6,159,225 A | 12/2000 | Makower |
| 6,162,214 A | 12/2000 | Mueller et al. |
| 6,165,188 A | 12/2000 | Saadat et al. |
| 6,167,315 A | 12/2000 | Coe et al. |
| 6,174,307 B1 | 1/2001 | Daniel et al. |
| 6,190,352 B1 | 2/2001 | Haarala et al. |
| 6,190,353 B1 | 2/2001 | Makower et al. |
| 6,193,650 B1 | 2/2001 | Ryan et al. |
| 6,203,537 B1 | 3/2001 | Adrian |
| 6,210,400 B1 | 4/2001 | Hebert et al. |
| 6,228,052 B1 | 5/2001 | Pohndorf |
| 6,228,076 B1 | 5/2001 | Winston et al. |
| 6,235,044 B1 | 5/2001 | Root et al. |
| 6,241,692 B1 | 6/2001 | Tu et al. |
| 6,245,011 B1 | 6/2001 | Dudda et al. |
| 6,251,121 B1 | 6/2001 | Saadat |
| 6,258,083 B1 | 7/2001 | Daniel et al. |
| 6,290,668 B1 | 9/2001 | Gregory et al. |
| 6,315,774 B1 | 11/2001 | Daniel et al. |
| 6,324,434 B2 | 11/2001 | Coe et al. |
| 6,368,318 B1 | 4/2002 | Visuri et al. |
| 6,395,002 B1 | 5/2002 | Ellman et al. |
| 6,398,773 B1 | 6/2002 | Bagaoisan et al. |
| 6,402,771 B1 | 6/2002 | Palmer et al. |
| 6,402,781 B1 | 6/2002 | Langberg et al. |
| 6,419,674 B1 | 7/2002 | Bowser et al. |
| 6,419,684 B1 | 7/2002 | Heisler et al. |
| 6,423,051 B1 | 7/2002 | Kaplan et al. |
| 6,428,539 B1 | 8/2002 | Baxter et al. |
| 6,428,556 B1 | 8/2002 | Chin |
| 6,432,119 B1 | 8/2002 | Saadat |
| 6,436,054 B1 | 8/2002 | Viola et al. |
| 6,436,114 B1 | 8/2002 | Novak et al. |
| 6,440,125 B1 | 8/2002 | Rentrop |
| 6,454,741 B1 | 9/2002 | Muni et al. |
| 6,454,758 B1 | 9/2002 | Thompson et al. |
| 6,461,349 B1 | 10/2002 | Elbrecht et al. |
| 6,478,777 B1 | 11/2002 | Honeck et al. |
| 6,485,413 B1 | 11/2002 | Boppart et al. |
| 6,485,485 B1 | 11/2002 | Winston et al. |
| 6,488,636 B2 | 12/2002 | Bryan et al. |
| 6,500,182 B2 | 12/2002 | Foster |
| 6,512,959 B1 | 1/2003 | Gomperz et al. |
| 6,527,752 B1 | 3/2003 | Bosley et al. |
| 6,537,314 B2 | 3/2003 | Langberg et al. |
| 6,554,779 B2 | 4/2003 | Viola et al. |
| 6,558,382 B2 | 5/2003 | Jahns et al. |
| 6,565,583 B1 | 5/2003 | Deaton et al. |
| 6,565,588 B1 | 5/2003 | Clement et al. |
| 6,569,082 B1 | 5/2003 | Chin |
| 6,575,997 B1 | 6/2003 | Palmer et al. |
| 6,592,607 B1 | 7/2003 | Palmer et al. |
| 6,595,982 B2 | 7/2003 | Sekino et al. |
| 6,599,296 B1 | 7/2003 | Gillick et al. |
| 6,602,241 B2 | 8/2003 | Makower et al. |
| 6,607,547 B1 | 8/2003 | Chin |
| 6,610,046 B1 | 8/2003 | Usami et al. |
| 6,610,066 B2 | 8/2003 | Dinger et al. |
| 6,613,013 B2 | 9/2003 | Haarala et al. |
| 6,620,153 B2 | 9/2003 | Mueller et al. |
| 6,620,160 B2 | 9/2003 | Lewis et al. |
| 6,620,180 B1 | 9/2003 | Bays et al. |
| 6,641,590 B1 | 11/2003 | Palmer et al. |
| 6,652,480 B1 | 11/2003 | Imran et al. |
| 6,652,548 B2 | 11/2003 | Evans et al. |
| 6,660,021 B1 | 12/2003 | Palmer et al. |
| 6,663,621 B1 | 12/2003 | Winston et al. |
| 6,663,626 B2 | 12/2003 | Truckai et al. |
| 6,669,685 B1 | 12/2003 | Rizoiu et al. |
| 6,673,090 B2 | 1/2004 | Root et al. |
| 6,687,548 B2 | 2/2004 | Goode |
| 6,702,813 B1 | 3/2004 | Baxter et al. |
| 6,706,018 B2 | 3/2004 | Westlund et al. |
| 6,706,052 B1 | 3/2004 | Chin |
| 6,706,065 B2 | 3/2004 | Langberg et al. |
| 6,709,456 B2 | 3/2004 | Langberg et al. |
| 6,712,773 B1 | 3/2004 | Viola |
| 6,712,826 B2 | 3/2004 | Lui |
| 6,772,014 B2 | 8/2004 | Coe et al. |
| 6,802,838 B2 | 10/2004 | Loeb et al. |
| 6,805,692 B2 | 10/2004 | Muni et al. |
| 6,810,882 B2 | 11/2004 | Langberg et al. |
| 6,818,001 B2 | 11/2004 | Wulfman et al. |
| 6,855,143 B2 | 2/2005 | Davison et al. |
| 6,858,027 B2 | 2/2005 | Redtenbacher et al. |
| 6,860,860 B2 | 3/2005 | Viola |
| 6,869,431 B2 | 3/2005 | Maguire et al. |
| 6,871,085 B2 | 3/2005 | Sommer |
| 6,884,240 B1 | 4/2005 | Dykes |
| 6,887,238 B2 | 5/2005 | Jahns et al. |
| 6,893,450 B2 | 5/2005 | Foster |
| 6,913,612 B2 | 7/2005 | Palmer et al. |
| 6,962,585 B2 | 11/2005 | Poleo et al. |
| 6,966,906 B2 | 11/2005 | Brown |
| 6,979,290 B2 | 12/2005 | Mourlas et al. |
| 6,979,319 B2 | 12/2005 | Manning et al. |
| 6,989,028 B2 | 1/2006 | Lashinski et al. |
| 6,999,809 B2 | 2/2006 | Currier et al. |
| 7,004,956 B2 | 2/2006 | Palmer et al. |
| 7,011,682 B2 | 3/2006 | Lashinski et al. |
| 7,029,467 B2 | 4/2006 | Currier et al. |
| 7,033,335 B2 | 4/2006 | Haarala et al. |
| 7,033,344 B2 | 4/2006 | Imran |
| 7,033,357 B2 | 4/2006 | Baxter et al. |
| 7,060,061 B2 | 6/2006 | Altshuler et al. |
| 7,063,693 B2 | 6/2006 | Guenst |
| 7,077,845 B2 * | 7/2006 | Hacker ............ A61B 17/32002 606/180 |
| 7,077,856 B2 | 7/2006 | Whitman |
| 7,092,765 B2 | 8/2006 | Geske et al. |
| 7,104,983 B2 | 9/2006 | Grasso et al. |
| 7,114,642 B2 | 10/2006 | Whitman |
| 7,117,039 B2 | 10/2006 | Manning et al. |
| 7,149,587 B2 | 12/2006 | Wardle et al. |
| 7,151,965 B2 | 12/2006 | Osypka |
| 7,189,207 B2 | 3/2007 | Viola |
| 7,191,015 B2 | 3/2007 | Lamson et al. |
| 7,192,430 B2 | 3/2007 | Truckai et al. |
| 7,204,824 B2 | 4/2007 | Moulis |
| 7,214,180 B2 | 5/2007 | Chin |
| 7,226,459 B2 | 6/2007 | Cesarini et al. |

(56) References Cited

U.S. PATENT DOCUMENTS

| | | |
|---|---|---|
| 7,238,179 B2 | 7/2007 | Brucker et al. |
| 7,238,180 B2 | 7/2007 | Mester et al. |
| 7,252,641 B2 | 8/2007 | Thompson et al. |
| 7,264,587 B2 | 9/2007 | Chin |
| 7,273,478 B2 | 9/2007 | Appling et al. |
| 7,276,052 B2 | 10/2007 | Kobayashi et al. |
| 7,288,096 B2 | 10/2007 | Chin |
| 7,296,577 B2 | 11/2007 | Lashinski et al. |
| 7,306,588 B2 | 12/2007 | Loeb et al. |
| 7,326,226 B2 | 2/2008 | Root et al. |
| 7,328,071 B1 | 2/2008 | Stehr et al. |
| 7,344,546 B2 | 3/2008 | Wulfman et al. |
| 7,357,794 B2 | 4/2008 | Makower et al. |
| 7,359,756 B2 | 4/2008 | Goode |
| 7,369,901 B1 | 5/2008 | Morgan et al. |
| 7,392,095 B2 | 6/2008 | Flynn et al. |
| 7,396,354 B2 | 7/2008 | Rychnovsky et al. |
| 7,398,781 B1 | 7/2008 | Chin |
| 7,449,010 B1 | 11/2008 | Hayase et al. |
| 7,462,167 B2 | 12/2008 | Kratz et al. |
| 7,485,127 B2 | 2/2009 | Nistal |
| 7,494,484 B2 | 2/2009 | Beck et al. |
| 7,507,252 B2 | 3/2009 | Lashinski et al. |
| 7,509,169 B2 | 3/2009 | Eigler et al. |
| 7,510,524 B2 | 3/2009 | Vayser et al. |
| 7,510,576 B2 | 3/2009 | Langberg et al. |
| 7,513,877 B2 | 4/2009 | Viola |
| 7,513,892 B1 | 4/2009 | Haarala et al. |
| 7,526,342 B2 | 4/2009 | Chin et al. |
| 7,537,602 B2 | 5/2009 | Whitman |
| 7,540,865 B2 | 6/2009 | Griffin et al. |
| 7,544,197 B2 | 6/2009 | Kelsch et al. |
| 7,559,941 B2 | 7/2009 | Zannis et al. |
| D600,792 S | 9/2009 | Eubanks et al. |
| 7,591,790 B2 | 9/2009 | Pflueger |
| 7,597,698 B2 | 10/2009 | Chin |
| 7,606,615 B2 | 10/2009 | Makower et al. |
| 7,611,474 B2 | 11/2009 | Hibner et al. |
| 7,637,904 B2 | 12/2009 | Wingler et al. |
| 7,645,286 B2 | 1/2010 | Catanese et al. |
| 7,648,466 B2 | 1/2010 | Stephens et al. |
| 7,651,503 B1 | 1/2010 | Coe et al. |
| 7,651,504 B2 | 1/2010 | Goode et al. |
| D610,259 S | 2/2010 | Way et al. |
| D611,146 S | 3/2010 | Way et al. |
| 7,674,272 B2 | 3/2010 | Torrance et al. |
| 7,695,485 B2 | 4/2010 | Whitman et al. |
| 7,695,512 B2 | 4/2010 | Lashinski et al. |
| 7,697,996 B2 | 4/2010 | Manning et al. |
| 7,713,231 B2 | 5/2010 | Wulfman et al. |
| 7,713,235 B2 | 5/2010 | Torrance et al. |
| 7,713,281 B2 | 5/2010 | Leeflang et al. |
| 7,722,549 B2 | 5/2010 | Nakao |
| 7,740,626 B2 | 6/2010 | Takayama et al. |
| 7,743,960 B2 | 6/2010 | Whitman et al. |
| D619,252 S | 7/2010 | Way et al. |
| D619,253 S | 7/2010 | Way et al. |
| 7,758,594 B2 | 7/2010 | Lamson et al. |
| 7,758,613 B2 | 7/2010 | Whitman |
| D621,939 S | 8/2010 | Way et al. |
| 7,766,923 B2 | 8/2010 | Catanese et al. |
| 7,780,682 B2 | 8/2010 | Catanese et al. |
| 7,780,694 B2 | 8/2010 | Palmer et al. |
| 7,794,411 B2 | 9/2010 | Ritchart et al. |
| 7,798,813 B1 | 9/2010 | Harrel |
| 7,801,624 B1 | 9/2010 | Flannery et al. |
| 7,803,151 B2 | 9/2010 | Whitman |
| 7,806,835 B2 | 10/2010 | Hibner et al. |
| 7,811,281 B1 | 10/2010 | Rentrop |
| 7,815,655 B2 | 10/2010 | Catanese et al. |
| 7,842,009 B2 | 11/2010 | Torrance et al. |
| 7,845,538 B2 | 12/2010 | Whitman |
| 7,858,038 B2 | 12/2010 | Andreyko et al. |
| 7,875,018 B2 | 1/2011 | Tockman et al. |
| 7,875,049 B2 | 1/2011 | Eversull et al. |
| 7,890,186 B2 | 2/2011 | Wardle et al. |
| 7,890,192 B1 | 2/2011 | Kelsch et al. |
| 7,896,879 B2 | 3/2011 | Solsberg et al. |
| 7,896,891 B2 | 3/2011 | Catanese et al. |
| 7,905,889 B2 | 3/2011 | Catanese et al. |
| 7,909,836 B2 | 3/2011 | McLean et al. |
| 7,914,464 B2 | 3/2011 | Burdorff et al. |
| 7,914,542 B2 | 3/2011 | Lamson et al. |
| D635,671 S | 4/2011 | Way et al. |
| 7,918,230 B2 | 4/2011 | Whitman et al. |
| 7,918,803 B2 | 4/2011 | Ritchart et al. |
| 7,930,040 B1 | 4/2011 | Kelsch et al. |
| 7,935,146 B2 | 5/2011 | Langberg et al. |
| 7,938,786 B2 | 5/2011 | Ritchie et al. |
| 7,942,830 B2 | 5/2011 | Solsberg et al. |
| 7,951,071 B2 | 5/2011 | Whitman et al. |
| 7,951,158 B2 | 5/2011 | Catanese et al. |
| 7,963,040 B2 | 6/2011 | Shan et al. |
| 7,963,433 B2 | 6/2011 | Whitman et al. |
| 7,974,710 B2 | 7/2011 | Seifert |
| 7,981,049 B2 | 7/2011 | Ritchie et al. |
| 7,981,050 B2 | 7/2011 | Ritchart et al. |
| 7,981,128 B2 | 7/2011 | To et al. |
| 7,988,726 B2 | 8/2011 | Langberg et al. |
| 7,991,258 B2 | 8/2011 | Temelkuran et al. |
| 7,992,758 B2 | 8/2011 | Whitman et al. |
| 7,993,350 B2 | 8/2011 | Ventura et al. |
| 7,993,351 B2 | 8/2011 | Worley et al. |
| 7,993,359 B1 | 8/2011 | Atwell et al. |
| 8,007,469 B2 | 8/2011 | Duffy |
| 8,007,488 B2 | 8/2011 | Ravenscroft |
| 8,007,503 B2 | 8/2011 | Catanese et al. |
| 8,007,506 B2 | 8/2011 | To et al. |
| 8,016,748 B2 | 9/2011 | Mourlas et al. |
| 8,016,844 B2 | 9/2011 | Privitera et al. |
| 8,016,855 B2 | 9/2011 | Whitman et al. |
| 8,016,858 B2 | 9/2011 | Whitman |
| 8,021,373 B2 | 9/2011 | Whitman et al. |
| 8,025,199 B2 | 9/2011 | Whitman et al. |
| 8,043,309 B2 | 10/2011 | Catanese et al. |
| RE42,959 E | 11/2011 | Saadat et al. |
| 8,052,616 B2 | 11/2011 | Andrisek et al. |
| 8,052,659 B2 | 11/2011 | Ravenscroft et al. |
| 8,056,786 B2 | 11/2011 | Whitman et al. |
| 8,056,791 B2 | 11/2011 | Whitman |
| 8,070,762 B2 | 12/2011 | Escudero et al. |
| 8,090,430 B2 | 1/2012 | Makower et al. |
| 8,097,012 B2 | 1/2012 | Kagarise |
| 8,100,920 B2 | 1/2012 | Gambale et al. |
| 8,118,208 B2 | 2/2012 | Whitman |
| 8,126,570 B2 | 2/2012 | Manning et al. |
| 8,128,577 B2 | 3/2012 | Viola |
| 8,128,636 B2 | 3/2012 | Lui et al. |
| 8,133,214 B2 | 3/2012 | Hayase et al. |
| 8,137,377 B2 | 3/2012 | Palmer et al. |
| 8,142,442 B2 | 3/2012 | Palmer et al. |
| 8,142,446 B2 | 3/2012 | Shan |
| RE43,300 E | 4/2012 | Saadat et al. |
| 8,157,815 B2 | 4/2012 | Catanese et al. |
| 8,186,559 B1 | 5/2012 | Whitman |
| 8,187,204 B2 | 5/2012 | Miller et al. |
| 8,187,268 B2 | 5/2012 | Godara et al. |
| 8,192,430 B2 | 6/2012 | Goode et al. |
| 8,202,229 B2 | 6/2012 | Miller et al. |
| 8,206,409 B2 | 6/2012 | Privitera et al. |
| 8,211,118 B2 | 7/2012 | Catanese et al. |
| 8,216,254 B2 | 7/2012 | McLean et al. |
| 8,235,916 B2 | 8/2012 | Whiting et al. |
| 8,236,016 B2 | 8/2012 | To et al. |
| 8,239,039 B2 | 8/2012 | Zarembo et al. |
| 8,241,272 B2 | 8/2012 | Arnold et al. |
| 8,251,916 B2 | 8/2012 | Speeg et al. |
| 8,252,015 B2 | 8/2012 | Leeflang et al. |
| 8,257,312 B2 | 9/2012 | Duffy |
| 8,272,554 B2 | 9/2012 | Whitman et al. |
| 8,273,078 B2 | 9/2012 | Muenker |
| 8,295,947 B2 | 10/2012 | Lamson et al. |
| 8,303,511 B2 | 11/2012 | Eigler et al. |
| 8,323,240 B2 | 12/2012 | Wulfman et al. |

(56) References Cited

U.S. PATENT DOCUMENTS

| | | |
|---|---|---|
| 8,326,437 B2 | 12/2012 | Cully et al. |
| 8,333,740 B2 | 12/2012 | Shippert |
| 8,333,776 B2 | 12/2012 | Cheng et al. |
| 8,337,516 B2 | 12/2012 | Escudero et al. |
| 8,343,167 B2 | 1/2013 | Henson |
| 8,343,187 B2 | 1/2013 | Lamson et al. |
| 8,353,899 B1 | 1/2013 | Wells et al. |
| 8,361,094 B2 | 1/2013 | To et al. |
| 8,364,280 B2 | 1/2013 | Marnfeldt et al. |
| 8,372,098 B2 | 2/2013 | Tran |
| 8,394,110 B2 | 3/2013 | Catanese et al. |
| 8,394,113 B2 | 3/2013 | Wei et al. |
| 8,425,535 B2 | 4/2013 | McLean et al. |
| 8,512,326 B2 * | 8/2013 | Shadduck .............. A61B 18/18 606/167 |
| 9,028,520 B2 * | 5/2015 | Taylor ..................... A61B 1/32 606/190 |
| 9,301,773 B2 * | 4/2016 | Olomutzki ....... A61B 17/32053 |
| 9,413,896 B2 | 8/2016 | Bowe et al. |
| 9,504,807 B2 | 11/2016 | Drasler et al. |
| 9,724,122 B2 | 8/2017 | Hendrick et al. |
| 9,730,756 B2 * | 8/2017 | Ben Oren ...... A61B 17/320016 |
| 9,763,692 B2 | 9/2017 | Bowe et al. |
| 9,949,753 B2 * | 4/2018 | Bowe ............... A61B 17/32075 |
| 2001/0005789 A1 | 6/2001 | Root et al. |
| 2001/0016717 A1 | 8/2001 | Haarala et al. |
| 2001/0025174 A1 | 9/2001 | Daniel et al. |
| 2001/0031981 A1 | 10/2001 | Evans et al. |
| 2001/0041899 A1 | 11/2001 | Foster |
| 2002/0002372 A1 | 1/2002 | Jahns et al. |
| 2002/0007190 A1 * | 1/2002 | Wulfman ....... A61B 17/320725 606/167 |
| 2002/0007204 A1 | 1/2002 | Goode |
| 2002/0010475 A1 | 1/2002 | Lui |
| 2002/0010487 A1 | 1/2002 | Evans et al. |
| 2002/0016628 A1 | 2/2002 | Langberg et al. |
| 2002/0026127 A1 | 2/2002 | Balbierz et al. |
| 2002/0042610 A1 | 4/2002 | Sliwa et al. |
| 2002/0045811 A1 | 4/2002 | Kittrell et al. |
| 2002/0065543 A1 | 5/2002 | Gomperz et al. |
| 2002/0068954 A1 | 6/2002 | Foster |
| 2002/0077593 A1 | 6/2002 | Perkins et al. |
| 2002/0087151 A1 | 7/2002 | Mody et al. |
| 2002/0103477 A1 | 8/2002 | Grasso et al. |
| 2002/0103532 A1 | 8/2002 | Langberg et al. |
| 2002/0103533 A1 | 8/2002 | Langberg et al. |
| 2002/0123785 A1 | 9/2002 | Zhang et al. |
| 2002/0151961 A1 | 10/2002 | Lashinski et al. |
| 2002/0156346 A1 | 10/2002 | Kamrava et al. |
| 2002/0183735 A1 | 12/2002 | Edwards et al. |
| 2002/0188278 A1 | 12/2002 | Tockman et al. |
| 2003/0009146 A1 | 1/2003 | Muni et al. |
| 2003/0009157 A1 | 1/2003 | Levine et al. |
| 2003/0050630 A1 | 3/2003 | Mody et al. |
| 2003/0050631 A1 | 3/2003 | Mody et al. |
| 2003/0055444 A1 | 3/2003 | Evans et al. |
| 2003/0055445 A1 | 3/2003 | Evans et al. |
| 2003/0065312 A1 | 4/2003 | Owa et al. |
| 2003/0065316 A1 | 4/2003 | Levine et al. |
| 2003/0069575 A1 | 4/2003 | Chin et al. |
| 2003/0073985 A1 | 4/2003 | Mueller et al. |
| 2003/0078562 A1 | 4/2003 | Makower et al. |
| 2003/0092995 A1 | 5/2003 | Thompson |
| 2003/0105451 A1 | 6/2003 | Westlund et al. |
| 2003/0125619 A1 | 7/2003 | Manning et al. |
| 2003/0144594 A1 | 7/2003 | Gellman |
| 2003/0167056 A1 | 9/2003 | Jahns et al. |
| 2003/0181935 A1 | 9/2003 | Gardeski et al. |
| 2003/0187460 A1 | 10/2003 | Chin et al. |
| 2003/0187461 A1 | 10/2003 | Chin |
| 2003/0199921 A1 | 10/2003 | Palmer et al. |
| 2003/0204202 A1 | 10/2003 | Palmer et al. |
| 2003/0208209 A1 | 11/2003 | Gambale et al. |
| 2003/0229323 A1 | 12/2003 | Haarala et al. |
| 2003/0229353 A1 | 12/2003 | Cragg |
| 2004/0006358 A1 | 1/2004 | Wulfman et al. |
| 2004/0010248 A1 | 1/2004 | Appling et al. |
| 2004/0015193 A1 | 1/2004 | Lamson et al. |
| 2004/0019359 A1 | 1/2004 | Worley et al. |
| 2004/0049208 A1 | 3/2004 | Hill et al. |
| 2004/0054368 A1 | 3/2004 | Truckai et al. |
| 2004/0054388 A1 | 3/2004 | Osypka |
| 2004/0059348 A1 | 3/2004 | Geske et al. |
| 2004/0059404 A1 | 3/2004 | Bjorklund et al. |
| 2004/0064024 A1 | 4/2004 | Sommer |
| 2004/0068256 A1 | 4/2004 | Rizoiu et al. |
| 2004/0068288 A1 | 4/2004 | Palmer et al. |
| 2004/0093016 A1 | 5/2004 | Root et al. |
| 2004/0097788 A1 | 5/2004 | Mourlas et al. |
| 2004/0102804 A1 | 5/2004 | Chin |
| 2004/0102841 A1 | 5/2004 | Langberg et al. |
| 2004/0111101 A1 | 6/2004 | Chin |
| 2004/0116939 A1 | 6/2004 | Goode |
| 2004/0116992 A1 | 6/2004 | Wardle et al. |
| 2004/0133220 A1 | 7/2004 | Lashinski et al. |
| 2004/0138528 A1 | 7/2004 | Richter et al. |
| 2004/0138562 A1 | 7/2004 | Makower et al. |
| 2004/0138744 A1 | 7/2004 | Lashinski et al. |
| 2004/0143284 A1 | 7/2004 | Chin |
| 2004/0147911 A1 | 7/2004 | Sinofsky |
| 2004/0147912 A1 | 7/2004 | Sinofsky |
| 2004/0147913 A1 | 7/2004 | Sinofsky |
| 2004/0153096 A1 | 8/2004 | Goode et al. |
| 2004/0153098 A1 | 8/2004 | Chin et al. |
| 2004/0153146 A1 | 8/2004 | Lashinski et al. |
| 2004/0158236 A1 | 8/2004 | Thyzel |
| 2004/0172116 A1 | 9/2004 | Seifert et al. |
| 2004/0176840 A1 | 9/2004 | Langberg et al. |
| 2004/0181249 A1 | 9/2004 | Torrance et al. |
| 2004/0216748 A1 | 11/2004 | Chin |
| 2004/0220519 A1 | 11/2004 | Wulfman et al. |
| 2004/0225280 A1 | 11/2004 | Harrigan |
| 2004/0230212 A1 | 11/2004 | Wulfman |
| 2004/0230213 A1 | 11/2004 | Wulfman et al. |
| 2004/0235611 A1 | 11/2004 | Nistal |
| 2004/0236312 A1 | 11/2004 | Nistal et al. |
| 2004/0236397 A1 | 11/2004 | Coe et al. |
| 2004/0243123 A1 | 12/2004 | Grasso et al. |
| 2004/0243162 A1 | 12/2004 | Wulfman et al. |
| 2004/0254534 A1 | 12/2004 | Bjorkman et al. |
| 2004/0260322 A1 | 12/2004 | Rudko et al. |
| 2004/0267276 A1 | 12/2004 | Camino et al. |
| 2004/0267304 A1 | 12/2004 | Zannis et al. |
| 2005/0004644 A1 | 1/2005 | Kelsch et al. |
| 2005/0025798 A1 | 2/2005 | Moulis |
| 2005/0027199 A1 | 2/2005 | Clarke |
| 2005/0027337 A1 | 2/2005 | Rudko et al. |
| 2005/0038419 A9 | 2/2005 | Arnold et al. |
| 2005/0060030 A1 | 3/2005 | Lashinski et al. |
| 2005/0065561 A1 | 3/2005 | Manning et al. |
| 2005/0090748 A1 | 4/2005 | Makower et al. |
| 2005/0096643 A1 | 5/2005 | Brucker et al. |
| 2005/0096740 A1 | 5/2005 | Langberg et al. |
| 2005/0131399 A1 | 6/2005 | Loeb et al. |
| 2005/0149104 A1 | 7/2005 | Leeflang et al. |
| 2005/0149105 A1 | 7/2005 | Leeflang et al. |
| 2005/0165288 A1 | 7/2005 | Rioux et al. |
| 2005/0197623 A1 | 9/2005 | Leeflang et al. |
| 2005/0222607 A1 | 10/2005 | Palmer et al. |
| 2005/0228402 A1 | 10/2005 | Hofmann |
| 2005/0228452 A1 | 10/2005 | Mourlas et al. |
| 2005/0251116 A1 | 11/2005 | Steinke et al. |
| 2005/0259942 A1 | 11/2005 | Temelkuran et al. |
| 2005/0273090 A1 | 12/2005 | Nieman et al. |
| 2005/0283143 A1 | 12/2005 | Rizoiu |
| 2005/0288596 A1 | 12/2005 | Eigler et al. |
| 2005/0288604 A1 | 12/2005 | Eigler et al. |
| 2005/0288654 A1 | 12/2005 | Nieman et al. |
| 2005/0288722 A1 | 12/2005 | Eigler et al. |
| 2006/0004317 A1 | 1/2006 | Mauge et al. |
| 2006/0052660 A1 | 3/2006 | Chin |
| 2006/0084839 A1 | 4/2006 | Mourlas et al. |
| 2006/0100663 A1 | 5/2006 | Palmer et al. |
| 2006/0116746 A1 | 6/2006 | Chin |

(56) References Cited

U.S. PATENT DOCUMENTS

| | | |
|---|---|---|
| 2006/0116757 A1 | 6/2006 | Lashinski et al. |
| 2006/0167417 A1 | 7/2006 | Kratz et al. |
| 2006/0173440 A1 | 8/2006 | Lamson et al. |
| 2006/0217755 A1 | 9/2006 | Eversull et al. |
| 2006/0229490 A1 | 10/2006 | Chin |
| 2006/0235431 A1 | 10/2006 | Goode et al. |
| 2006/0247751 A1 | 11/2006 | Seifert |
| 2006/0253179 A1 | 11/2006 | Goode et al. |
| 2006/0265042 A1 | 11/2006 | Catanese et al. |
| 2006/0276871 A1 | 12/2006 | Lamson et al. |
| 2006/0287574 A1 | 12/2006 | Chin |
| 2007/0015964 A1 | 1/2007 | Eversull et al. |
| 2007/0016130 A1 | 1/2007 | Leeflang et al. |
| 2007/0021812 A1 | 1/2007 | Manning et al. |
| 2007/0049929 A1 | 3/2007 | Catanese et al. |
| 2007/0050003 A1 | 3/2007 | Zarembo et al. |
| 2007/0078500 A1 | 4/2007 | Ryan et al. |
| 2007/0083217 A1 | 4/2007 | Eversull et al. |
| 2007/0100410 A1 | 5/2007 | Lamson et al. |
| 2007/0106328 A1 | 5/2007 | Wardle et al. |
| 2007/0129710 A1 | 6/2007 | Rudko et al. |
| 2007/0142846 A1 | 6/2007 | Catanese et al. |
| 2007/0197861 A1 | 8/2007 | Reiley et al. |
| 2007/0198020 A1 | 8/2007 | Reiley et al. |
| 2007/0232981 A1 | 10/2007 | Ravenscroft et al. |
| 2007/0276412 A1 | 11/2007 | Catanese et al. |
| 2007/0293853 A1 | 12/2007 | Truckai et al. |
| 2008/0004643 A1 | 1/2008 | To et al. |
| 2008/0004644 A1 | 1/2008 | To et al. |
| 2008/0004645 A1 | 1/2008 | To et al. |
| 2008/0004646 A1 | 1/2008 | To et al. |
| 2008/0004647 A1 | 1/2008 | To et al. |
| 2008/0015625 A1 | 1/2008 | Ventura et al. |
| 2008/0021484 A1 | 1/2008 | Catanese et al. |
| 2008/0021485 A1 | 1/2008 | Catanese et al. |
| 2008/0033232 A1 | 2/2008 | Catanese et al. |
| 2008/0033456 A1 | 2/2008 | Catanese et al. |
| 2008/0033458 A1 | 2/2008 | McLean et al. |
| 2008/0033488 A1 | 2/2008 | Catanese et al. |
| 2008/0039833 A1 | 2/2008 | Catanese et al. |
| 2008/0039872 A1 | 2/2008 | Catanese et al. |
| 2008/0039874 A1 | 2/2008 | Catanese et al. |
| 2008/0039875 A1 | 2/2008 | Catanese et al. |
| 2008/0039876 A1 | 2/2008 | Catanese et al. |
| 2008/0039889 A1 | 2/2008 | Lamson et al. |
| 2008/0039893 A1 | 2/2008 | McLean et al. |
| 2008/0039894 A1 | 2/2008 | Catanese et al. |
| 2008/0045986 A1 | 2/2008 | To et al. |
| 2008/0051756 A1 | 2/2008 | Makower et al. |
| 2008/0058759 A1 | 3/2008 | Makower et al. |
| 2008/0071341 A1 | 3/2008 | Goode et al. |
| 2008/0071342 A1 | 3/2008 | Goode et al. |
| 2008/0097378 A1 | 4/2008 | Zuckerman |
| 2008/0097426 A1 | 4/2008 | Root et al. |
| 2008/0103439 A1 | 5/2008 | Torrance et al. |
| 2008/0103446 A1 | 5/2008 | Torrance et al. |
| 2008/0103516 A1 | 5/2008 | Wulfman et al. |
| 2008/0125634 A1 | 5/2008 | Ryan et al. |
| 2008/0125748 A1 | 5/2008 | Patel |
| 2008/0147061 A1 | 6/2008 | Goode et al. |
| 2008/0154293 A1 | 6/2008 | Taylor |
| 2008/0154296 A1 | 6/2008 | Taylor et al. |
| 2008/0183163 A1 | 7/2008 | Lampropoulos et al. |
| 2008/0194969 A1 | 8/2008 | Werahera et al. |
| 2008/0208105 A1 | 8/2008 | Zelickson et al. |
| 2008/0221560 A1 | 9/2008 | Arai et al. |
| 2008/0228208 A1 | 9/2008 | Wulfman et al. |
| 2008/0249516 A1 | 10/2008 | Muenker |
| 2008/0262516 A1 | 10/2008 | Gambale et al. |
| 2008/0275497 A1 | 11/2008 | Palmer et al. |
| 2008/0275498 A1 | 11/2008 | Palmer et al. |
| 2008/0281308 A1 | 11/2008 | Neuberger et al. |
| 2008/0287888 A1 | 11/2008 | Ravenscroft |
| 2008/0306333 A1 | 12/2008 | Chin |
| 2009/0012510 A1 | 1/2009 | Bertolero et al. |
| 2009/0018523 A1 | 1/2009 | Lamson et al. |
| 2009/0018553 A1 | 1/2009 | McLean et al. |
| 2009/0034927 A1 | 2/2009 | Temelkuran et al. |
| 2009/0036871 A1 | 2/2009 | Hayase et al. |
| 2009/0054918 A1 | 2/2009 | Henson |
| 2009/0060977 A1 | 3/2009 | Lamson et al. |
| 2009/0071012 A1 | 3/2009 | Shan et al. |
| 2009/0076522 A1 | 3/2009 | Shan |
| 2009/0131907 A1 | 5/2009 | Chin et al. |
| 2009/0157045 A1 | 6/2009 | Haarala et al. |
| 2009/0182313 A1 | 7/2009 | Auld |
| 2009/0187196 A1 | 7/2009 | Vetter |
| 2009/0192439 A1 | 7/2009 | Lamson et al. |
| 2009/0198098 A1 | 8/2009 | Okada et al. |
| 2009/0204128 A1 | 8/2009 | Lamson et al. |
| 2009/0221994 A1 | 9/2009 | Neuberger et al. |
| 2009/0222025 A1 | 9/2009 | Catanese et al. |
| 2009/0227999 A1 | 9/2009 | Willis et al. |
| 2009/0234378 A1 | 9/2009 | Escudero et al. |
| 2009/0319015 A1 | 12/2009 | Horn-Wyffels |
| 2010/0004606 A1 | 1/2010 | Hansen et al. |
| 2010/0016836 A1 | 1/2010 | Makower et al. |
| 2010/0030154 A1 | 2/2010 | Duffy |
| 2010/0030161 A1 | 2/2010 | Duffy |
| 2010/0030262 A1 | 2/2010 | McLean et al. |
| 2010/0030263 A1 | 2/2010 | Cheng et al. |
| 2010/0049225 A1 | 2/2010 | To et al. |
| 2010/0063488 A1 | 3/2010 | Fischer et al. |
| 2010/0125253 A1 | 5/2010 | Olson et al. |
| 2010/0137873 A1 | 6/2010 | Grady et al. |
| 2010/0160952 A1 | 6/2010 | Leeflang et al. |
| 2010/0191165 A1 | 7/2010 | Appling et al. |
| 2010/0198194 A1 | 8/2010 | Manning et al. |
| 2010/0198229 A1 | 8/2010 | Olomutzki et al. |
| 2010/0217277 A1 | 8/2010 | Truong |
| 2010/0222737 A1 | 9/2010 | Arnold et al. |
| 2010/0222787 A1 | 9/2010 | Goode et al. |
| 2010/0240951 A1 | 9/2010 | Catanese et al. |
| 2010/0256616 A1 | 10/2010 | Katoh et al. |
| 2010/0268175 A1 | 10/2010 | Lunsford et al. |
| 2010/0280496 A1 | 11/2010 | Shippert |
| 2010/0324472 A1 | 12/2010 | Wulfman |
| 2010/0331793 A1 | 12/2010 | Tulleken |
| 2011/0004238 A1 | 1/2011 | Palmer et al. |
| 2011/0009957 A1 | 1/2011 | Langberg et al. |
| 2011/0022057 A1 | 1/2011 | Eigler et al. |
| 2011/0028959 A1 | 2/2011 | Chasan |
| 2011/0034790 A1 | 2/2011 | Mourlas et al. |
| 2011/0040238 A1 | 2/2011 | Wulfman et al. |
| 2011/0040312 A1 | 2/2011 | Lamson et al. |
| 2011/0040315 A1 | 2/2011 | To et al. |
| 2011/0040326 A1 | 2/2011 | Wei et al. |
| 2011/0046648 A1 | 2/2011 | Johnston et al. |
| 2011/0054493 A1 | 3/2011 | McLean et al. |
| 2011/0060349 A1 | 3/2011 | Cheng et al. |
| 2011/0071440 A1 | 3/2011 | Torrance et al. |
| 2011/0105947 A1 | 5/2011 | Fritscher-Ravens et al. |
| 2011/0106004 A1 | 5/2011 | Eubanks et al. |
| 2011/0106099 A1 | 5/2011 | Duffy et al. |
| 2011/0112548 A1 | 5/2011 | Fifer et al. |
| 2011/0112562 A1 | 5/2011 | Torrance |
| 2011/0112563 A1 | 5/2011 | To et al. |
| 2011/0112564 A1 | 5/2011 | Wolf |
| 2011/0118660 A1 | 5/2011 | Torrance et al. |
| 2011/0144423 A1 | 6/2011 | Tong et al. |
| 2011/0144425 A1 | 6/2011 | Catanese et al. |
| 2011/0151463 A1 | 6/2011 | Wulfman |
| 2011/0152607 A1 | 6/2011 | Catanese et al. |
| 2011/0152906 A1 | 6/2011 | Escudero et al. |
| 2011/0152907 A1 | 6/2011 | Escudero et al. |
| 2011/0160747 A1 | 6/2011 | McLean et al. |
| 2011/0160748 A1 | 6/2011 | Catanese et al. |
| 2011/0166564 A1 | 7/2011 | Merrick et al. |
| 2011/0178543 A1 | 7/2011 | Chin et al. |
| 2011/0190758 A1 | 8/2011 | Lamson et al. |
| 2011/0196298 A1 | 8/2011 | Anderson et al. |
| 2011/0196355 A1 | 8/2011 | Mitchell et al. |
| 2011/0196357 A1 | 8/2011 | Srinivasan |
| 2011/0208207 A1 | 8/2011 | Bowe et al. |

(56) References Cited

U.S. PATENT DOCUMENTS

| | | |
|---|---|---|
| 2011/0218528 A1 | 9/2011 | Ogata et al. |
| 2011/0238078 A1 | 9/2011 | Goode et al. |
| 2011/0238102 A1 | 9/2011 | Gutfinger et al. |
| 2011/0245751 A1 | 10/2011 | Hofmann |
| 2011/0257592 A1 | 10/2011 | Ventura et al. |
| 2011/0270169 A1 | 11/2011 | Gardeski et al. |
| 2011/0270170 A1 | 11/2011 | Gardeski et al. |
| 2011/0270289 A1 | 11/2011 | To et al. |
| 2011/0300010 A1 | 12/2011 | Jarnagin et al. |
| 2011/0301417 A1 | 12/2011 | Mourlas et al. |
| 2011/0301626 A1 | 12/2011 | To et al. |
| 2012/0035590 A1 | 2/2012 | Whiting et al. |
| 2012/0041422 A1 | 2/2012 | Whiting et al. |
| 2012/0053564 A1 | 3/2012 | Ravenscroft |
| 2012/0065466 A1 | 3/2012 | Slater |
| 2012/0065659 A1 | 3/2012 | To |
| 2012/0083810 A1 | 4/2012 | Escudero et al. |
| 2012/0083826 A1 | 4/2012 | Chao et al. |
| 2012/0095447 A1 | 4/2012 | Fojtik |
| 2012/0095479 A1 | 4/2012 | Bowe et al. |
| 2012/0097174 A1 | 4/2012 | Spotnitz et al. |
| 2012/0123411 A1 | 5/2012 | Ibrahim et al. |
| 2012/0136341 A1 | 5/2012 | Appling et al. |
| 2012/0165827 A1 | 6/2012 | Khairkhahan et al. |
| 2012/0165861 A1 | 6/2012 | Palmer et al. |
| 2012/0191015 A1 | 7/2012 | Zannis et al. |
| 2012/0209173 A1 | 8/2012 | Hayase et al. |
| 2012/0215305 A1 | 8/2012 | Le et al. |
| 2012/0239008 A1 | 9/2012 | Fojtik |
| 2012/0245600 A1 | 9/2012 | McLean et al. |
| 2012/0253229 A1 | 10/2012 | Cage |
| 2012/0265183 A1 | 10/2012 | Tulleken et al. |
| 2012/0323252 A1 | 12/2012 | Booker |
| 2012/0323253 A1 | 12/2012 | Garai et al. |
| 2012/0330292 A1 | 12/2012 | Shadduck et al. |
| 2013/0006228 A1 | 1/2013 | Johnson et al. |
| 2013/0035676 A1 | 2/2013 | Mitchell et al. |
| 2013/0085486 A1 | 4/2013 | Boutoussov et al. |
| 2013/0096582 A1 | 4/2013 | Cheng et al. |
| 2013/0103047 A1 | 4/2013 | Steingisser et al. |
| 2014/0031800 A1 | 1/2014 | Ben Oren et al. |
| 2014/0081252 A1 | 3/2014 | Bowe et al. |
| 2014/0081289 A1 | 3/2014 | Fiser |
| 2014/0081303 A1 | 3/2014 | Bowe et al. |
| 2014/0081304 A1* | 3/2014 | Bowe ............... A61N 1/057 606/170 |
| 2014/0081306 A1 | 3/2014 | Bowe et al. |
| 2014/0081367 A1 | 3/2014 | Hendrick et al. |
| 2014/0275982 A1 | 9/2014 | Hendrick et al. |
| 2014/0276682 A1 | 9/2014 | Hendrick et al. |
| 2014/0276683 A1 | 9/2014 | Hendrick et al. |
| 2014/0276694 A1 | 9/2014 | Hendrick et al. |
| 2014/0276695 A1 | 9/2014 | Burton |
| 2014/0276696 A1 | 9/2014 | Schneider |
| 2014/0276920 A1 | 9/2014 | Hendrick et al. |
| 2014/0277037 A1 | 9/2014 | Grace et al. |
| 2014/0296897 A1 | 10/2014 | Sotak et al. |
| 2016/0022303 A1 | 1/2016 | Fiser |
| 2016/0338727 A1* | 11/2016 | Bowe ............... A61N 1/057 |
| 2017/0325835 A1 | 11/2017 | Bowe et al. |
| 2017/0340346 A1 | 11/2017 | Hendrick et al. |

FOREIGN PATENT DOCUMENTS

| | | |
|---|---|---|
| JP | 2004516073 A | 6/2004 |
| WO | 1991006271 A | 5/1991 |
| WO | 1991017711 A1 | 11/1991 |
| WO | 1993018818 A1 | 9/1993 |
| WO | 1995033513 A1 | 12/1995 |
| WO | 1999007295 A1 | 2/1999 |
| WO | 1999049937 A1 | 10/1999 |
| WO | 1999058066 A1 | 11/1999 |
| WO | 2001076680 A1 | 10/2001 |
| WO | 2002049690 A9 | 5/2003 |
| WO | 2004049956 A2 | 6/2004 |
| WO | 2004080345 A2 | 9/2004 |
| WO | 2004080507 A2 | 9/2004 |
| WO | 2006007410 A2 | 1/2006 |
| WO | 2008005888 A2 | 1/2008 |
| WO | 2008005891 A2 | 1/2008 |
| WO | 2008042987 A2 | 4/2008 |
| WO | 2009005779 A1 | 1/2009 |
| WO | 2009054968 A1 | 4/2009 |
| WO | 2009065082 A1 | 5/2009 |
| WO | 2009126309 A2 | 10/2009 |
| WO | 2011003113 A1 | 1/2011 |
| WO | 2011084863 A2 | 7/2011 |
| WO | 2011133941 A2 | 10/2011 |
| WO | 2011162595 A1 | 12/2011 |
| WO | 2012009697 A4 | 4/2012 |
| WO | 2012098335 A1 | 7/2012 |
| WO | 2012114333 A1 | 8/2012 |
| WO | 2012177117 A1 | 12/2012 |
| WO | 2013036588 A1 | 3/2013 |

OTHER PUBLICATIONS

Department of Health and Ageing in Australian Government, "Horizon Scanning Technology Prioritising: Laser Extraction Systems." 2010. 15 pages.
Extended European Search Report for European Application No. 07255018.9, dated Nov. 12, 2010, 7 pages.
Extended European Search Report issued in EP application 13837908, dated May 5, 2016, 6 pages.
Extended European Search Report issued in EP Application No. 13836886.5, dated Apr. 7, 2016, 6 pages.
Final Action for U.S. Appl. No. 11/615,005, dated Nov. 9, 2009, 10 pages.
Final Action for U.S. Appl. No. 11/615,005, dated Nov. 21, 2013, 20 pages.
Final Action for U.S. Appl. No. 11/615,006 dated Oct. 26, 2009, 9 pages.
Intent to Grant for European Patent Application No. 07255018.9, dated Nov. 29, 2012, 7 pages.
International Preliminary Examination Report issued in PCT/US2013/059448, completed Mar. 26, 2015, 9 pages.
International Search Report and Written Opinion for International Patent Application No. PCT/US2013/059434, dated Dec. 13, 2013, 14 pages.
International Search Report and Written Opinion issued in PCT/US2013/059448, dated Dec. 16, 2013, 12 pages.
Kennergren et al. "Laser-Assisted Lead Extraction: the European Experience." Europace. 2007, vol. 9, No. 8. 6 pages.
Notice of Allowance for European Patent Application No. 07255018.9, dated Jul. 26, 2012, 47 pages.
Notice of Allowance for Japan Patent Application No. 2007-333273, dated Jan. 16, 2014, 3 pages.
Official Action for European Application No. 07255019.7, dated Jul. 21, 2010 4 pages.
Official Action for European Patent Application No. 07255018.9, dated Jul. 19, 2011, 3 pages.
Official Action for U.S. Appl. No. 11/615,005, dated Apr. 16, 2009, 13 pages.
Official Action for U.S. Appl. No. 11/615,005, dated Feb. 11, 2011, 12 pages.
Official Action for U.S. Appl. No. 11/615,005, dated Jul. 21, 2010, 10 pages.
Official Action for U.S. Appl. No. 11/615,005, dated Mar. 14, 2013, 16 pages.
Official Action for U.S. Appl. No. 13/800,728, dated Jan. 16, 2014, 14 pages.
Official Action for U.S. Appl. No. 11/615,006 dated Apr. 24, 2009, 7 pages.
Official Action for U.S. Appl. No. 11/615,006 dated Feb. 17, 2010, 8 pages.
Official Action for U.S. Appl. No. 11/615,006 dated Jul. 20, 2010, 9 pages.

(56) References Cited

OTHER PUBLICATIONS

Official Action for U.S. Appl. No. 11/615,006 dated Mar. 14, 2013, 16 pages.
Official Action for U.S. Appl. No. 11/615,006 dated Nov. 22, 2013, 16 pages.
Official Action with English translation for Japan Patent Application No. 2007-333173, dated Apr. 30, 2013, 5 pages.
Official Action with English translation for Japan Patent Application No. 2007-333173, dated Aug. 13, 2012, 7 pages.
Papaioannou, T., et. al. Excimer Laser (308 nm) Recanalisation of In-Stent Restenosis: Thermal Considerations, Lasers Med Sci., 16(2):90-100, 2001. [Abstract Only].
St. Luke's Roosevelt Hospital Center. Laser Lead Extraction. Arrhythmia News, 11(2), 3 pages, 2006.
Wikoff, Bruce et al. "Pacemaker Lead Extraction with the Laser Sheath: Results of the Pacing Lead Extraction with the Excimer Sheath (PLEXES) Trial." Journal of the American College of Cardiology, 1999. vol. 33, No. 6. 8 pages.

\* cited by examiner

TISSUE SLITTING METHODS AND SYSTEMS

CROSS REFERENCE TO RELATED APPLICATIONS

The present application is divisional of prior U.S. application Ser. No. 13/828,310, filed Mar. 14, 2013, entitled "TISSUE SLITTING METHODS AND SYSTEMS," now U.S. Pat. No. 9,413,896 which claims the benefit of and priority, under 35 U.S.C. § 119(e), to U.S. Provisional Application Ser. No. 61/701,521, filed Sep. 14, 2012, entitled "TISSUE SEPARATING METHODS AND SYSTEMS," which are hereby incorporated herein by reference in their entirety for all that they teach and for all purposes.

This application is also related to U.S. patent application Ser. No. 13/828,231, filed on Mar. 14, 2013, entitled, "Tissue Slitting Methods and Systems"; Ser. No. 13/828,383, filed on Mar. 14, 2013, entitled, "Tissue Slitting Methods and Systems" Ser. No. 13/828,441, filed on Mar. 14, 2013, entitled, "Tissue Slitting Methods and Systems"; Ser. No. 13/828,638, filed on Mar. 14, 2013, entitled, "Lead Removal Sleeve" and Ser. No. 13/828,536, filed on Mar. 14, 2013, entitled, "Expandable Lead Jacket". The entire disclosures of the applications listed above are hereby incorporated herein by reference, in their entirety, for all that they teach and for all purposes.

FIELD OF THE DISCLOSURE

The present disclosure relates generally to devices, methods and systems for separating tissue in a patient and more specifically, to techniques for separating tissue attached to leads in a patient.

BACKGROUND

Cardiac pacing systems typically include a pacemaker and one or more leads, which are placed inside the body of a patient. The pacemaker includes a power source and circuitry configured to send tinted electrical pulses to the lead. The lead carries the electrical pulse to the heart to initiate a heartbeat, and transmits information about the heart's electrical activity to the pacemaker. The lead can include a fixation mechanism that holds the lead to the cardiac tissue. In some cases, a lead is inserted through a vein or artery (collectively vasculature) and guided to the heart where it is attached. In other instances, a lead is attached to the outside of the heart. During its time in the body, tissue can attach to the lead in the form of lesions, adhesions or scar tissue, or tissue can encase a lead. In addition, the lead and/or tissue can become attached to the vasculature wall. At times, leads may be removed from patients for numerous reasons, including but not limited to, infections, lead age, and lead malfunction. Accordingly, removal or extraction of the lead may present associated complications.

Current lead extraction techniques include mechanical traction, mechanical devices, and laser devices. Mechanical traction can be accomplished by inserting a locking stylet into the hollow portion of the lead and then pulling the lead to remove it. An example of such a lead locking device is described and illustrated in U.S. Pat. No. 6,167,315 to Coe et al., which is hereby incorporated herein by reference in its entirety for all that it teaches and for all purposes. In some cases, dilating telescopic sheaths may also be used to strip away the scar tissue adhering the lead to the body. Examples of a such devices and methods used to extract leads is described and illustrated in United States Patent Publication No. 2008/0154293 to Taylor, which is hereby incorporated herein by reference in its entirety for all that it teaches and tor all purposes.

Dilation techniques typically involve pushing tissue away from the lead when the sheath is pushed longitudinally along the lead. However, this pushing technique may be difficult to implement, particularly when the lead has a tortuous path or curvature because the requisite longitudinal forces to extract the tissue from the lead in under these circumstances increase. The longitudinal forces also may require heavy counter forces on the lead, which may result in lead breakage.

Some mechanical sheaths have proposed trigger mechanisms for extending a blade from a sheath. At least some of these devices, however, involve complicated activation mechanisms and may not be well suited for negotiating the tortuous paths that exist in certain vascular or physiological environments.

Laser devices typically employ laser energy to cut the scar tissue away from the lead thus allowing for removal. Examples of such laser devices and systems are described and illustrated in U.S. Pat. Nos. 5,383,199 and 5,824,026 and 5,916,210 and 6,228,076 and 6,290,668 all of which are hereby incorporated herein by reference in their entirety for all that they teach and for all purposes.

Further complicating lead removal is the fact that in some cases, the leads may be located in, and/or attached to, the body of a patient, in a structurally-weak portion of the vasculature. For instance, typical leads in a human may pass through the innominate vein, past the superior vena cava ("SVC"), and into the right atrium of the heart. A majority of tissue growth can occur along the SVC and other locations along the innominate vein where the leads make contact with the vein walls. However, tissue growth can also occur at locations within a patient where the leads make contact with arterials or other areas of the vasculature. Certain veins and arteries, and certain areas of vein and arterial walls, can be thin which can make lead removal a complicated and delicate process.

SUMMARY

A traditional approach to removing tissue from implanted leads is based on the presumption that the tissue growths are adhered directly to the surfaces of the implanted leads. As such, methods and systems have been designed to dislocate the connection between the tissue attached to the implanted device and the body of a patient. Although some tissue may remain on the lead, current methods focus on removing most of the tissue surrounding a circumference of the lead. In other words, while tissue may remain attached around the lead, current systems essentially core around this tissue surrounding the circumference of a lead to free the lead along with a section of the cored tissue to create slack for removing the lead from a patient.

Surprisingly and unexpectedly, it has been discovered that tissue growth may not adhere directly to the implanted lead but actually form a substantially cylindrical "tube" around the implanted substantially cylindrical lead at a given contact area. Contrary to conventional wisdom, the tissue growth typically does not physically adhere to the lead. For example, this tissue growth, once formed completely around a lead, forms a tubular-shaped member that essentially holds the lead and resists lead removal. The tubular-shaped section of formed tissue around an implanted device may impart a combination of connection forces/modes that prevent the removal of the device from a patient. For example, the tubular-shaped section of formed tissue, or tissue growth, may constrict, capture, and/or surround implanted leads. In some cases, the tissue growth may constrict a lead, especially if a force is applied to one end of the lead during a removal operation. In other cases, the tissue growth may capture the lead and prevent removal, by, among other things, being attached to the patient and the lead simultaneously. Additionally or alternatively, the tissue growth, during attempted lead removal, may at least partially adhere to the lead in one or more sections while completely forming around the lead.

Based upon the surprising and unexpected discovery that tissue growth may not be directly adhered to the implanted lead, alternative devices and methods may be used to extract an object from such tissue. In other words, methods and devices are disclosed herein, that are capable of exploiting the growth nature of the tissue around a lead to efficiently extract the lead from tissue that acts to hold the lead with some type of force. The tissue growth may form around the lead such that the lead Is contained from free movement within a patient. For instance, the tissue growth may impart a clamping, or constrictive, force around the circumference of the lead that can prevent movement of the lead within this constrictive tissue growth. Due to the taught and constrictive nature of the tissue around the lead, the lead may be able to be removed without mechanically removing or laser ablating the entire tissue region surrounding the lead in a 360 degree, or circumferential, fashion. Rather, initiating a cut and/or slit of the tissue along a longitudinal axis of the lead may allow a surgeon to easily separate the lead from the tissue via the slit. For example, once the tissue is initially slit, a surgeon may be able to extract the lead from the tissue, by pulling the lead with the use of a lead locking, or similar, device. This lead extraction may be made possible by the initial slit reducing the restrictive forces caused by tissue growth in a given area. Lead extraction may also be effected by moving the lead against the initial slit created to tear through the tissue growth.

The tissue growth may need to be slit or cut along an entire length of tissue growth such that the tissue growth is no longer capable of imparting clamping, or constrictive, forces around the lead. Once the tissue growth Is slit along its length, removal of the lead from the section of tissue growth can be achieved using various lead removal techniques, including but not limited to, traction/counter-traction applied to the lead and growth, lead locking devices, snares, sheath insertion, moving the lead against the slit portion of the tissue, and the like.

Accordingly, there is a need for a device, method and/or system such as a device that includes a tissue slitting or cutting edge that facilitates slitting a length of formed tissue surrounding a lead, and optionally a method and system capable of removing the lead from the formed tissue that captures at least a portion of an implanted lead.

In an embodiment, a tissue slitting apparatus is provided comprising: a shaft, wherein the shaft is flexible, the shaft having a proximal and a distal end, and wherein the shaft includes an inner lumen running from the proximal to the distal end to receive at least one of an implanted object and mechanical traction device; and a tissue abrading device disposed adjacent to the distal end of the shaft, wherein the tissue abrading device is configured to wear a separation in a tissue growth along a side and a length of the tissue growth, and wherein the tissue slitting apparatus separates a first, but not a second, portion of the tissue growth around a circumference of the implanted object.

In another embodiment, a method is provided comprising: separating only a portion of a tissue growth at least substantially surrounding an implanted object in a patient; and thereafter removing the implanted object from the tissue growth. In one embodiment, the separating and thereafter removing steps may comprise the sub-steps: attaching a mechanical traction device to the implanted object; inserting the mechanical traction device into a tissue slitting apparatus, the tissue slitting apparatus further comprising: a flexible shaft, wherein the flexible shaft has a proximal and a distal end; an internal lumen, wherein the internal lumen is configured to allow at least one of an implanted object and mechanical traction device to pass therethrough; and a tissue abrading device operatively connected to the distal end of the flexible shaft, wherein the tissue abrading device is configured to wear a separation in the tissue growth along a side and a length of the tissue growth, and wherein the tissue slitting apparatus separates a first, but not a second, portion of the tissue growth around a circumference of the implanted object; applying a mechanical traction force to the mechanical traction device; indexing the tissue slitting apparatus to an engagement area of the tissue growth in contact with the implanted object; moving the tissue abrading device into the tissue growth; and actuating the tissue abrading device, such that the tissue growth is separated from the implanted object at least at the engagement area with the tissue abrading device.

In yet another embodiment, a system to remove tissue from a vascular lumen is provided, the system comprising: a lead locking device for locking onto a lead within the vascular lumen; a flexible shaft comprising: a proximal end; a distal end comprising at least one abrasive surface capable of wearing through tissue; and an internal lumen configured to allow at least one lead to pass therethrough, wherein the lead locking device holds the lead while the at least one abrasive surface wears through a section of tissue surrounding at least a portion of the lead.

The method can include the steps of cutting only a portion of a tissue growth at least substantially surrounding an implanted object in a patient and thereafter removing the implanted object, in embodiments disclosed herein, the tissue growth may be subjected to a slitting action about a partial (i.e., not complete) periphery of an internal diameter of the tissue growth. In some embodiments, the tissue growth portion cut can be no more than about 50% of a perimeter of the tissue growth adjacent to and surrounding, substantially or completely, the implanted object at any point along an encased length of the implanted object.

The tissue slitting edge may include sharpened area, point, or blade, in a static fixed and/or dynamically deployable configuration. Additionally or alternatively, the tissue slitting edge may utilize grinding mechanisms to cause a slit in the formed tissue. Additionally or alternatively, the tissue slitting edge may utilize emitted energy, such as light, thermal energy, electromagnetic energy, and/or high-pressure fluid emission to cause a slit in the formed tissue. The tissue slitting edge can be an energy device, such as a power sheath, which typically applies a form of energy at the sheath tip to cut the scar tissue away from the lead thus allowing for removal. As the sheath is pushed over the lead and comes to an area of attachment, the operator can turn on the sheath's energy source to heat or vaporize scar tissue, forming the desired slit. One of these specialized sheaths uses electrocautery, similar to what is used to cut through tissue in surgery. Another sheath has one or more tiny lasers at its tip or edge. When activated, the lasers vaporize water molecules in scar tissue within 1 mm, forming the desired slit or cut. Additionally or alternatively, dilating telescopic sheaths or inflatable balloons having a longitudinally positioned tissue slitting edge can be expanded, thereby deploying the tissue slitting edge to form the desired slit.

Accordingly, slitting devices (e.g., in the form of knife-edges, blades, planers, lasers and other electromagnetic radiation emitters, high-pressure fluid, grinders, sanders, drills, RF devices, ultrasonic devices, and the like) can be configured in various combinations and methods by which formed tissue can be removed from an implanted lead subjected to any combination of connection modes via the formed tissue.

Removal of the formed tissue, or tissue growth, from a lead may be effected by creating a slit, or cut, along a length of the tissue growth. By slitting the formed tissue along an axial portion, or length, of the tissue connected to the surgically implanted device or surgical implant, it is anticipated that the connection to the implanted lead will be severely weakened. In many cases, the tissue slitting device may allow the implanted lead to essentially peel away from the tissue previously surrounding the implanted lead, thereby releasing it from containment. These and other needs are addressed by the various aspects, embodiments, and/or configurations of the present disclosure. Also, while the disclosure is presented in terms of exemplary embodiments, it should be appreciated that individual aspects of the disclosure can be separately claimed.

The tissue slitting device includes a flexible shaft having a proximal end, a distal end, and an internal lumen having an internal diameter configured to allow a lead, lead locking device, and/or other implanted device to pass through it. The device may also include a tissue slitting tip operatively coupled with the distal end of the flexible shaft. As can be appreciated, the slitting of formed tissue can be performed by at least one of cutting, drilling, slicing, stripping, chopping, sanding, grinding, planing, abrasion, high-pressure fluid, laser ablation, and combinations thereof. It is anticipated that the tissue slitting device may be oriented within a patient via use of the flexible shaft and monitor, or a catheter-based system. In some cases, the tissue slitting device may be positioned toward the center of the vasculature, and/or proximal to a non-traumatic leading edge, such that any sharp, or working, edge is caused to contact tissue growth and not contact the vasculature.

Among other things, the slitting section of the tissue slitting device may be biased against a lead/object via spring force. Additionally or alternatively, the tissue slitting device may include a flexible portion configured to allow the tissue slitting device to move as directed within a patient.

The phrases "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together. When each one of A, B, and C in the above expressions refers to an element, such as X, Y, and Z, or class of elements, such as $X_1$-$X_n$, $Y_1$-$Y_m$, and $Z_1$-$Z_o$, the phrase is intended to refer to a single element selected from X, Y, and Z, a combination of elements selected from the same class (e.g., $X_1$ and $X_2$) as well as a combination of elements selected from two or more classes (e.g., $Y_1$ and $Z_o$).

The term "a" or "an" entity refers to one or more of that entity. As such, the terms "a" (or "an"), "one or more" and "at least one" can be used interchangeably herein. It is also to be noted that the terms "comprising", "including", and "having" can be used interchangeably.

"Electromagnetic radiation" (EM radiation or EMR) is a form of energy emitted and/or absorbed by charged particles, which exhibits wave-like behavior as it travels through space. EMR has both electric and magnetic field components, which stand in a fixed ratio of intensity to each other, and which oscillate in phase perpendicular to each other and perpendicular to the direction of energy and wave propagation. EM radiation is commonly classified by wavelength into radio, microwave, infrared, the visible spectrum perceived as visible light, ultraviolet, X-rays, and gamma rays. "Radiation" includes both EM radiation and static electric and magnetic and near fields.

A "lead" is a conductive structure, typically an electrically insulated coiled wire. The electrically conductive material can be any conductive material, with metals and intermetallic alloys common. The outer sheath of insulative material is biocompatible and biostable (e.g., non-dissolving in the body ) and generally includes organic materials such as polyurethane and polyimide. Lead types include, by way of non-limiting example, epicardial and endocardial leads. Leads are commonly implanted into a body percutaneously or surgically.

A "surgical implant" is a medical device manufactured to replace a missing biological structure, support, stimulate, or treat a damaged biological structure, or enhance, stimulate, or treat an existing biological structure. Medical implants are man-made devices, in contrast to a transplant, which is a transplanted biomedical tissue. In some cases implants contain electronics, including, without limitation, artificial pacemaker, defibrillator, electrodes, and cochlear implants. Some implants are bioactive, including, without limitation, subcutaneous drug delivery devices in the form of implantable pills or drug-eluting stents.

The term "means" as used herein shall be given its broadest possible interpretation in accordance with 35 U.S.C., Section 112, Paragraph 6. Accordingly, a claim incorporating the term "means" shall cover all structures, materials, or acts set forth herein, and all of the equivalents thereof. Further, the structures, materials or acts and the equivalents thereof shall include all those described in the summary of the invention, brief description of the drawings, detailed description, abstract, and claims themselves.

It should be understood that every maximum numerical limitation given throughout this disclosure is deemed to include each and every lower numerical limitation as an alternative, as if such lower numerical limitations were expressly written herein. Every minimum numerical limitation given throughout this disclosure is deemed to include each and every higher numerical limitation as an alternative, as if such higher numerical limitations were expressly written herein. Every numerical range given throughout this disclosure is deemed to include each and every narrower numerical range that falls within such broader numerical range, as if such narrower numerical ranges were all expressly written herein.

The preceding is a simplified summary of the disclosure to provide an understanding of some aspects of the disclosure. This summary is neither an extensive nor exhaustive overview of the disclosure and its various aspects, embodiments, and configurations. It is intended neither to identify key or critical elements of the disclosure nor to delineate the scope of the disclosure but to present selected concepts of the disclosure in a simplified form as an introduction to the more detailed description presented below. As will be appreciated, other aspects, embodiments, and configurations of the disclosure are possible utilizing, alone or in combination, one or more of the features set forth above or described in detail below.

BRIEF DESCRIPTION OF THE DRAWINGS

The accompanying drawings are incorporated into and form a part of the specification to illustrate several examples of the present disclosure. These drawings, together with the description, explain the principles of the disclosure. The drawings simply illustrate preferred and alternative examples of how the disclosure can be made and used and are not to be construed as limiting the disclosure to only the illustrated and described examples. Further features and advantages will become apparent from the following, more detailed, description of the various aspects, embodiments, and configurations of the disclosure, as illustrated by the drawings referenced below.

It should be understood that the drawings are not necessarily to scale. In certain instances, details that are not necessary for an understanding of the disclosure or that render other details difficult to perceive may have been omitted. It should be understood, of course, that the disclosure is not necessarily limited to the particular embodiments illustrated herein.

DETAILED DESCRIPTION

Before any embodiments of the disclosure are explained in detail, it is to be understood that the disclosure is not limited in its application to the details of construction and the arrangement of components set forth in the following description or illustrated in the following drawings. The disclosure is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

Embodiments of the present disclosure are directed to tissue slitting or cutting devices and methods of using tissue slitting devices to remove an implanted lead from within the vascular system of a patient. Among other things, the method of removing an implanted lead from formed tissue may include causing at least a partial separation of tissue that lies along an axial length of the implanted lead. In some embodiments, the tissue may be slit or cut along an entire length of the tissue growth to enable removal of the implanted lead. In other embodiments, the tissue may be slit or cut along a section of the tissue growth to allow an implanted lead to be removed from a patient.

While the phrases "tissue slitting edge" or "tissue cutting edge" are used in this disclosure, it is not limited to a blade or other cutting surface. These phrases are further intended to encompass any modality for slitting or cutting tissue, including the various modalities discussed herein. Nonlimiting examples include not only a sharpened area, point, or blade but also an abrasive or cutting wire or fiber, atherotomes (microsurgical blades) mounted on an inflatable (cutting) balloon, a grinder, high intensity light such as produced by a laser, thermal or infrared energy, electromagnetic energy, and/or high-pressure fluid.

Figure 1:
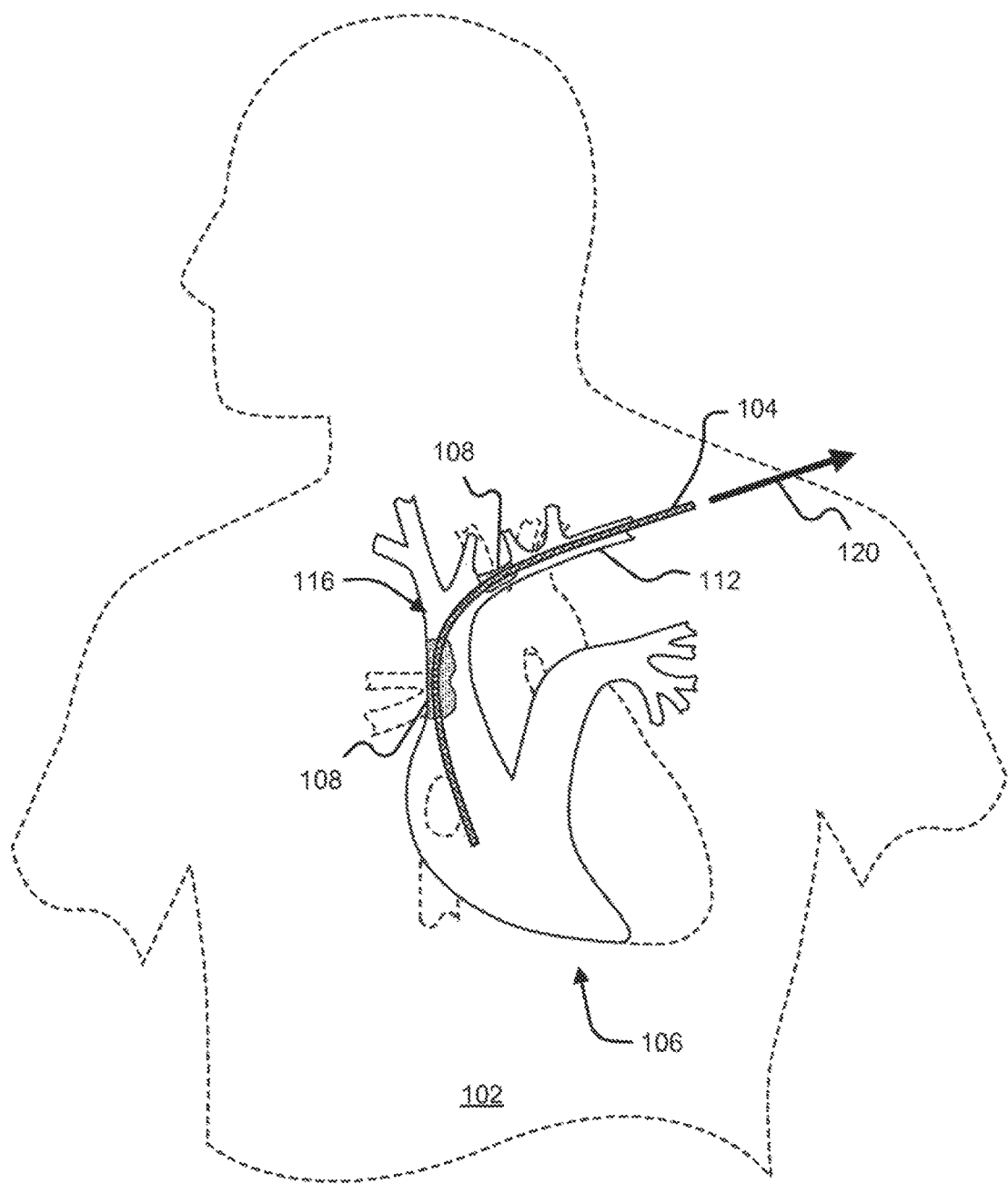
FIG. 1 shows an exemplary patient vasculature in section with implanted lead and multiple locations of tissue growth in accordance with some embodiments of the present disclosure.

FIG. 1 depicts an exemplary patient 102 with an implanted lead 104 running along the left innonimate vein 112 past the superior vena cava ("SVC") and connected into, or about, the right ventricle of the heart 106. Along the length of the lead 104 at least one formed tissue growth 108 is shown where the tissue 108 may completely surround a section of the lead 104. In a typical lead 104 explain procedure, the one or more of the tissue growths 108 may act to contain the lead 104. For example, the tissue 108 may impart one or more forces (e.g., constrictive, shear, compression, and the like) on the lead KM that may act to prevent successful removal of the lead 104 when subjected to a traction force 120.

Figure 2A:
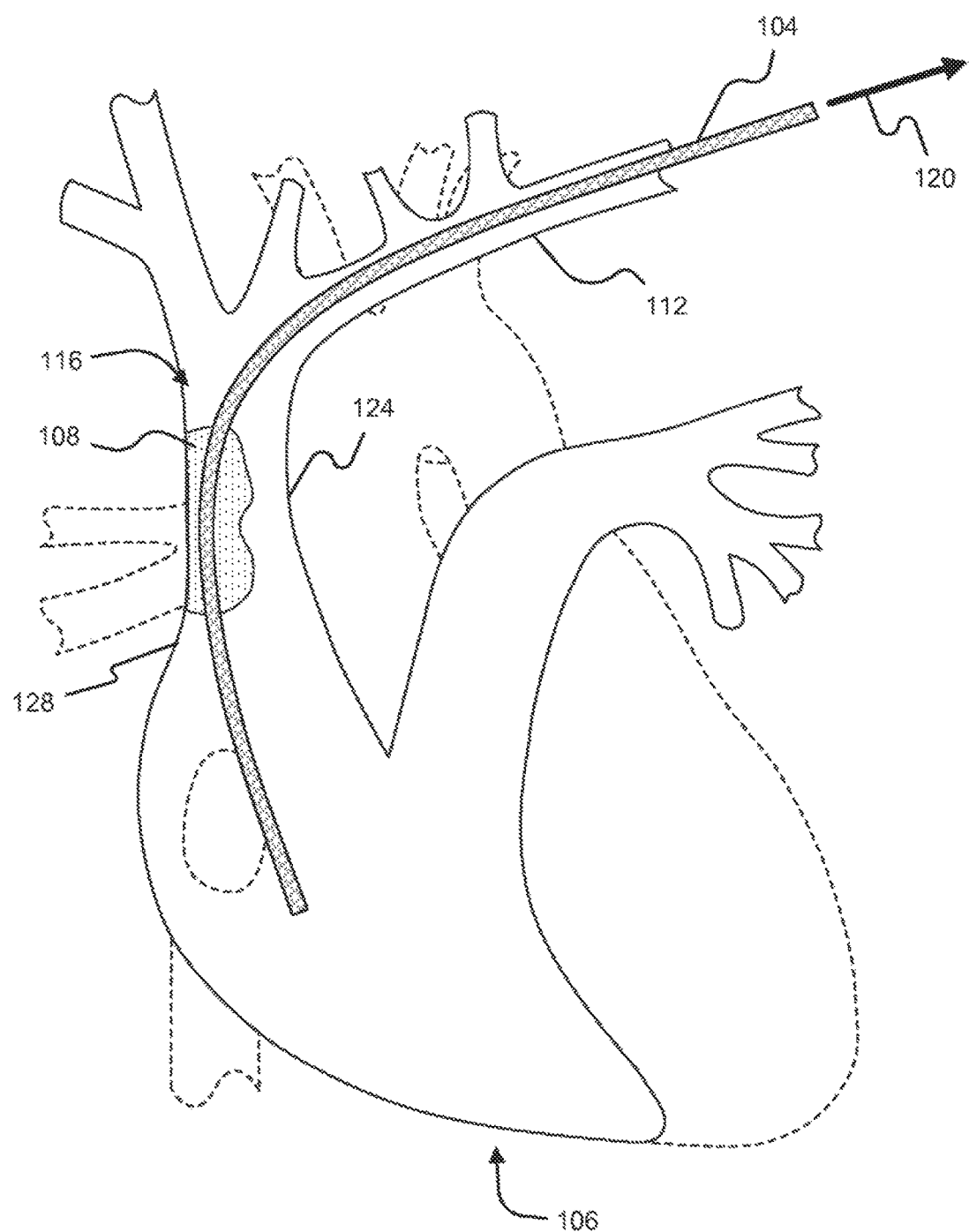
FIG. 2A shows a detail section view of a patient vasculature and implanted lead subjected to a traction force in a first path in accordance with some embodiments of the present disclosure.
Figure 2B:
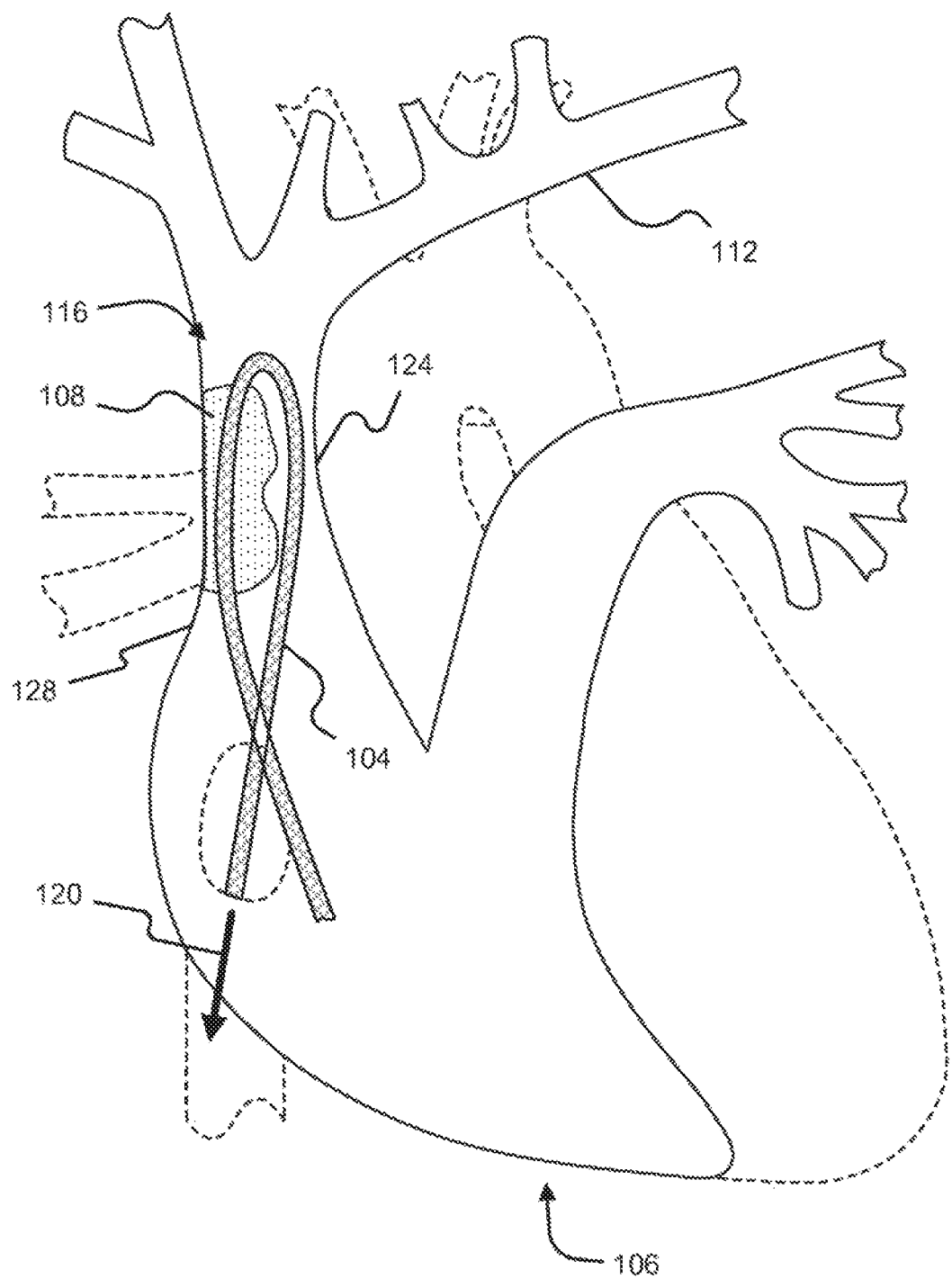
FIG. 2B shows a detail section view of a patient vasculature and implanted lead subjected to a traction force in second path in accordance with some embodiments of the present disclosure.
Figure 2C:
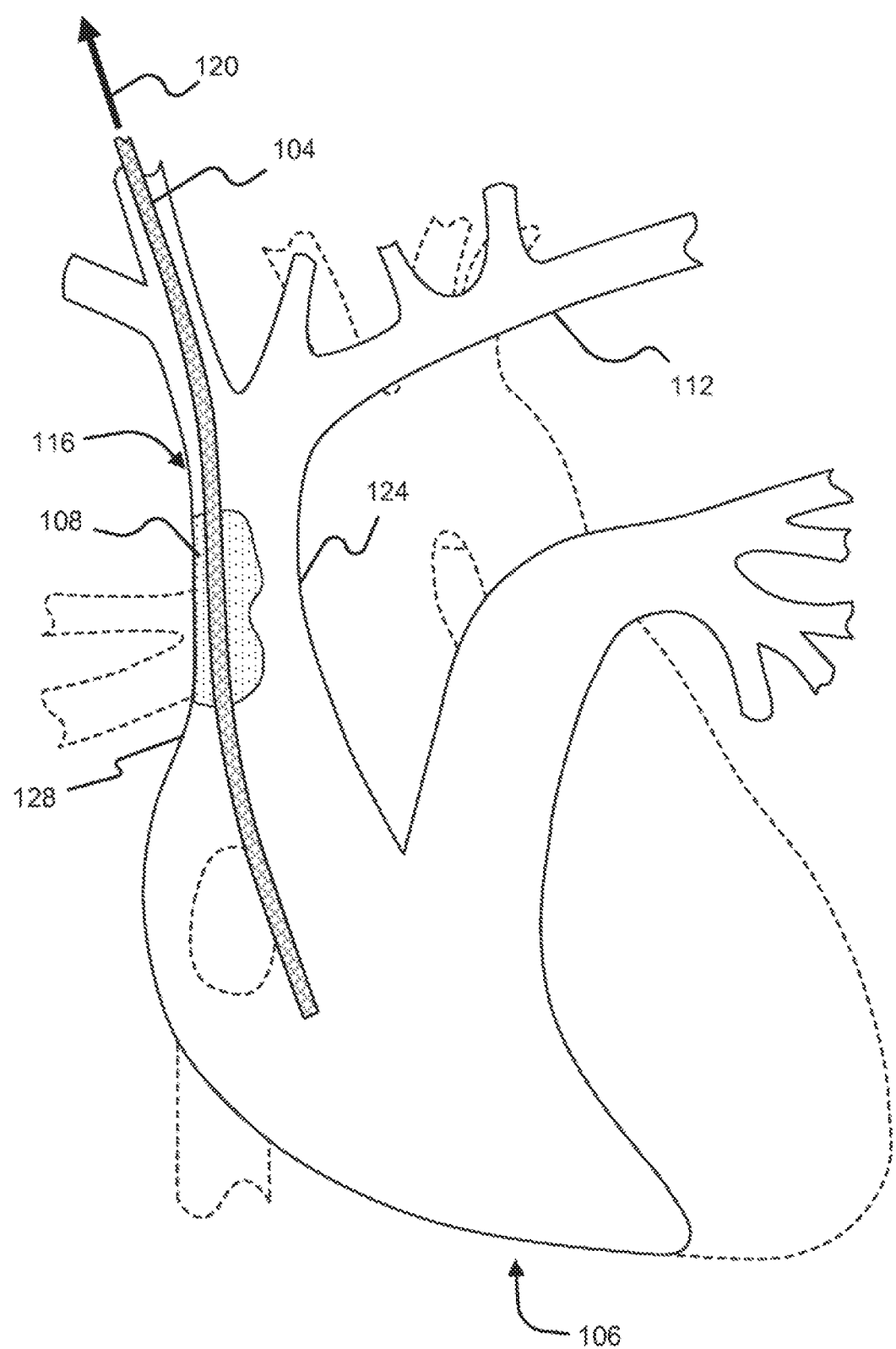
FIG. 2C shows a detail section view of a patient vasculature and implanted lead subjected to a traction force in third path in accordance with some embodiments of the present disclosure.

FIGS. 2A-C show examples of an implanted lead 104 subjected to a traction force via different paths in a patient 102 vasculature. Accordingly, the methods and/or devices disclosed in conjunction with any of the FIGS. 2A-C may equally apply to all instances disclosed.

FIG. 2A shows a detail view of a heart 106 having an implanted lead 104 subjected to a traction force 120 in a first path in accordance with embodiments of the present disclosure. In some embodiments, a lead 104 explant procedure may involve removing the lead from a patient 102 via one or more paths. For example, a lead-locking, or other traction, device may be engaged with the lead 104 and then used to pull the lead 104 from a patient. However, in some cases the lead 104 may be contained by a formed tissue growth 108 that resists the traction force 120 applied to the lead 104. As can be appreciated, subjecting the lead 104 to excessive traction forces 120 may cause a tear inside the patient 102 where the tissue is attached to the vasculature. In one example, a tissue growth 108 may form along a critical area of the vasculature, such as the SVC curve 116, of a patient. If this critical area is torn during a lead 104 explant procedure, the result can be fatal to the patient 102.

Complicating the lead 104 removal process is the fact that the tissue growth 108 surrounding a lead 104 may attach to a vessel in a curved portion of the vasculature. Removal of the lead 104 from such a curved portion of vasculature can present a challenge when introducing tissue removal devices alone or in conjunction with traction devices. In some cases, the tissue removal devices include sharp edges, aggressive tips, or imprecise actuation mechanisms that can puncture the thin walls of a patient 102 vasculature. It is an aspect of the present disclosure to orient a tissue slitting working end adjacent to the unconnected, or tissue free, side 124 of a vessel wall. This orientation can prevent puncture and/or damage occurring to the vasculature at the tissue connected side 128 of the vessel wall.

Referring now to FIG. 2B a detail section view of a patient vasculature and implanted lead 104 subjected to a traction force 120 in second path in accordance with some embodiments of the present disclosure is shown. In some instances, at least one end of the lead 104 may be directed inside a patient 102 for removal via a path within the vasculature. Direction of the lead 104 may be effected via a snaring tool, lead-locking device, traction device, combinations thereof, and the like. As shown in FIG. 2B, the lead 104 is directed toward the general direction of a patient's femoral artery via the inferior vena cava. The lead 104 may be directed in the manner shown to provide additional tearing forces on the tissue growth 108 by the lead 104 being subjected to a traction force 120. In one embodiment, the tissue growth 108 may be at least partially slit and the tearing forces created by pulling the lead 104 along the traction force 120 line cause the lead 104 to separate from the tissue growth 108. In other embodiments, a tissue slitting device may be run along the lead 104 to the tissue growth 108 via the femoral artery.

In some embodiments, the lead 104 may be captured and pulled such that the pull force causes the lead 104 to turn inside a patient 102. This mode of capture and pulling may cause a bending at a first connection point between the tissue growth 108 and the lead 104. When the tissue slitting device is engaged with the tissue growth 108, the assistive bending force provided by the traction force 120 can aid in slitting the tissue growth 108. For instance, the bending force may cause a stretching of the tissue growth 108 where the lead engages with the tissue growth 108. This stretching of tissue may assist in the slitting operation by causing tension on the fibers of the tissue growth 108 that, when slit, pull away from the tissue slitting device engagement area. As can be expected, the slitting operation may be performed in any area within a patient that is capable of receiving a tissue slitting device.

FIG. 2C shows a detail section view of a patient vasculature and implanted lead 104 subjected to a traction force 120 in third path in accordance with some embodiments of the present disclosure. Similar to FIGS. 2A and 2B, the lead 104 may be directed along a path in the patient vasculature. In this ease, the lead 104 may be directed toward the general direction of a patient's jugular vein.

As can be appreciated, the path chosen for removal of a lead 104 from a patient 102 may depend on one or more of the orientation of the lead 104 within a patient 102, the state of the at least one tissue growth 108, the lead removal device used, and the tissue slitting device used. In some cases, the lead 104 (e.g., pacing, defibrillator, etc.), or other object, may have moved after implantation. In these scenarios, the lead 104 may have to be captured via some other method. In some embodiments, a capturing tool equipped with a lasso, snare, or other lead grasping element may need to be inserted into the patient 102. As can be expected, the capturing tool may be inserted into the patient 102 via any number of the veins and/or arteries that are interconnected to the lead 104 location in the vasculature. For example, the lead 104 may be grasped via a capturing tool that has been inserted through a patient's femoral artery and led to the point of the vasculature where the lead's 104 free end may be located.

In some embodiments, rather than attach a separate mechanical traction device, the capturing tool may be used to provide traction force 120 during the tissue slitting operation. In accordance with embodiments of the present disclosure, the lead may be grasped via a capturing tool, or lead-locking device, and/or removed via some other pathway in the vasculature. In other words, the lead may be accessed via one or more veins, arteries, chambers, biological channels, and/or other sections of the vasculature of a patient 102.

Figure 3:
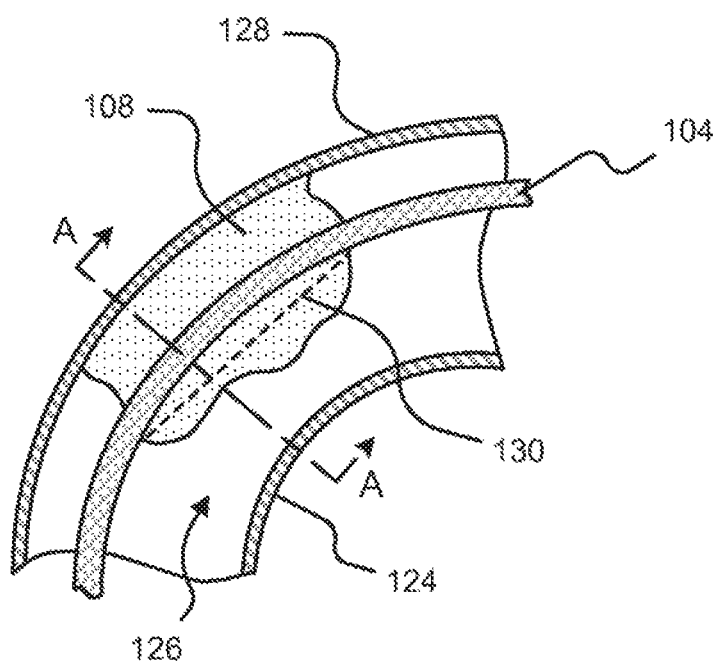
FIG. 3 shows a section view of a curved area of vasculature with tissue growth formed around an implanted lead in accordance with embodiments of the present disclosure.

FIG. 3 shows a section view of a curved area of vasculature with tissue growth 108 formed around an implanted lead 104 in accordance with embodiments of the present disclosure. The tissue growth 108 may completely surround a section of the lead 104 and even be attached to a vessel wall at a tissue connected side 128 of the vasculature. In some cases, the tissue growth 108 may not be adhered to at least one free side 124 of a vessel, such that a vessel opening 126 exists where bodily fluid may pass through the vessel unobstructed. Surprisingly and unexpectedly, it has been discovered that the tissue growth 108, before attempted lead extraction, is commonly at least substantially free of and even more commonly completely free of attachment to the lead 104.

Figure 4:
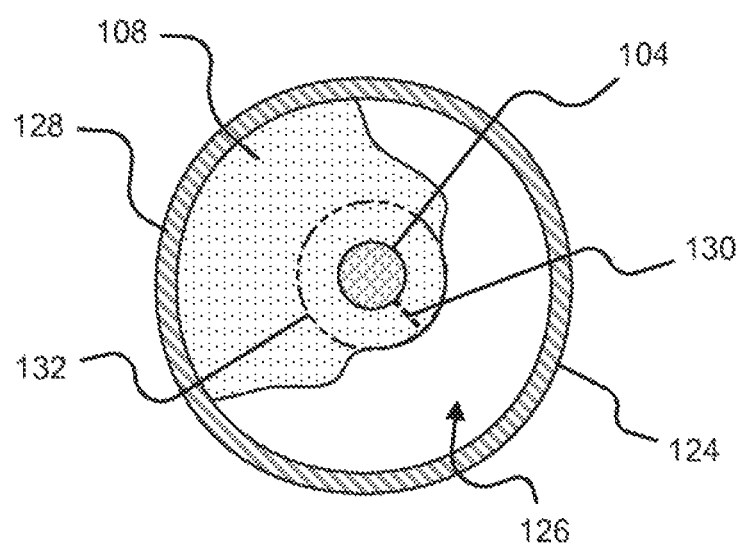
FIG. 4 shows a cross-sectional view of the curved area of vasculature of FIG. 3 taken along line A-A.

FIG. 4 shows a cross-sectional view of the curved area of vasculature of FIG. 3 taken along line A-A. In some embodiments, reference may be made to the tissue growth 108 forming a tube 132 (or cylindrical or sock-like structure) around the implanted lead 104. Previous methods have been disclosed that are directed to separating the tissue around the lead 104 in the area defined by the tube 132. It is an aspect of the present disclosure to provide one or more methods and devices to effectively separate the tissue growth 108 along a length of the lead to release the lead 104 from the containing forces of the tissue growth 108. In some embodiments, the tissue growth 108 may be slit at a portion of the tissue growth 108 where the thickness of tissue is minimal between the lead 104 and the open area 126 of the vessel.

Figure 5A:
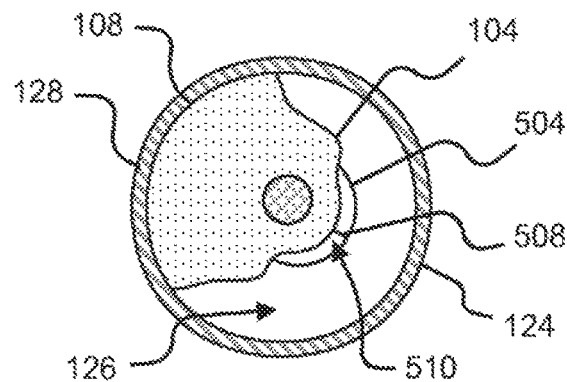
FIG. 5A shows a cross-sectional view of an area of vasculature with a tissue slitting device introduced in accordance with embodiments of the present disclosure.
Figure 5B:
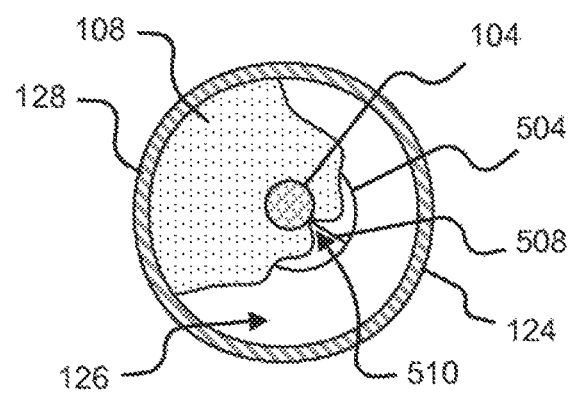
FIG. 5B shows a cross-sectional view of an area of vasculature with a tissue slitting device engaging formed tissue in accordance with embodiments of the present disclosure.
Figure 5C:
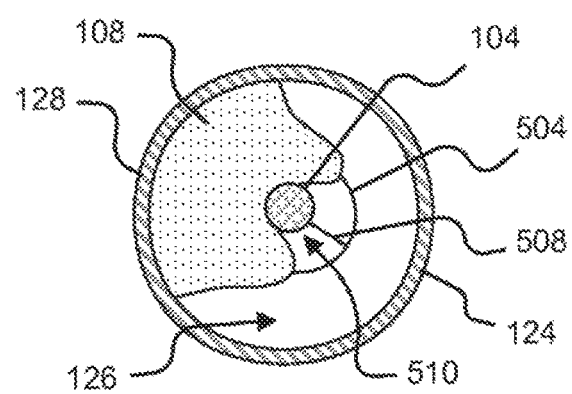
FIG. 5C shows a cross-sectional view of an area of vasculature with a tissue slitting device slitting formed tissue in accordance with embodiments of the present disclosure.

In embodiments disclosed herein, the tissue growth 108 may be subjected to a slitting action about a partial (i.e., not complete) periphery of an internal diameter of the tissue growth 108. Stated another way, at any selected point along the tissue growth 108 or tube 132 the amount of the adjacent tissue cut or slit 130 to free the lead 104 is commonly no more than about 50%, more commonly no more than about 25%, more commonly no more than about 10%, and even more commonly no more than about 5% of the diameter of the tissue growth 108 or tube 132. The length of the cut or slit 130 in the tissue growth 108 or tube 132 is commonly at least about 50%. more commonly at least about 75%, more commonly at least about 90%, and even more commonly at least about 95% of the total length of the portion of the lead 104 surrounded by the tissue growth 108 or tube 132 along an actual and projected line of the cut or slit FIGS. 5A-C show a cross-section of a vessel where a tissue slitting device 504 is progressively engaged with a tissue growth 108. As shown, the tissue slitting device causes a section of the tissue growth 108 to separate from a portion of the lead 104 allowing the forces containing the lead 104 to be severely weakened and/or eliminated.

Referring to FIG. 5A a cross-sectional view of an area of vasculature with a tissue slitting device 504 introduced therein in accordance with embodiments of the present disclosure is shown. The tissue slitting device 504 includes a tissue slitting tip 508 that is configured to separate tissue growth 108. In one embodiment, the tissue slitting tip 508 may be oriented such that a slitting operation is performed on the thinnest section of tissue growth 108 between the lead 104 and the open a tea 126 of the vessel. Orientation of the tissue slitting device 504 may be achieved in operation via a fluoroscopy and/or other monitoring devices and the use of one or more radiopaque markers on the tissue slitting device 504. Once the tissue slitting device 504 is oriented, the tissue slitting device 504 may contact the tissue growth 108 at an engagement area 510.

In any of the embodiments disclosed herein, the tissue slitting device may include an imaging system configured to provide an image from within the vasculature of a patient 102. It is anticipated that the imaging system may be disposed adjacent to the distal tip of the tissue slitting device. Examples of such imaging systems may include, but are in no way limited to, technology incorporating Intravascular Ultrasound ("IVUS"), Optical Coherence Tomography ("OCT"), radio imaging, magnetic tracking, three-dimensional ("3D") imaging, and other technologies that may be used to obtain an image within a patient.

FIG. 5B shows a cross-sectional view of an area of vasculature with a tissue slitting device 504 engaging formed tissue 108 in accordance with embodiments of the present disclosure. As the tissue slitting device 504 engages the tissue growth 108 the tissue slitting device 504, may slit the tissue growth 108 by splitting, cutting, tearing, grinding, sanding, ablating, and/or otherwise causing a separation of tissue at the engagement area 510.

FIG. 5C shows a cross-sectional view of an area of vasculature with a tissue slitting device 504 slitting formed tissue 108 in accordance with embodiments of the present disclosure. As shown in FIG. 5C, the tissue growth 108 is separated along a section of the lead 104 about the engagement area 510. In some embodiments, the tissue slitting device may be subsequently removed from the tissue growth 108 by moving the lead 104 in the direction of the separated tissue.

FIGS. 6A-D show a section view of a curved area of vasculature where an embodiment of a tissue slitting device 604 is progressively engaged with a tissue growth 108. As shown, the tissue slitting device 604 causes a section of the tissue growth 108 to separate from a portion of the lead 104 allowing the forces containing the lead 104 to be severely weakened and/or eliminated.

Figure 6A:
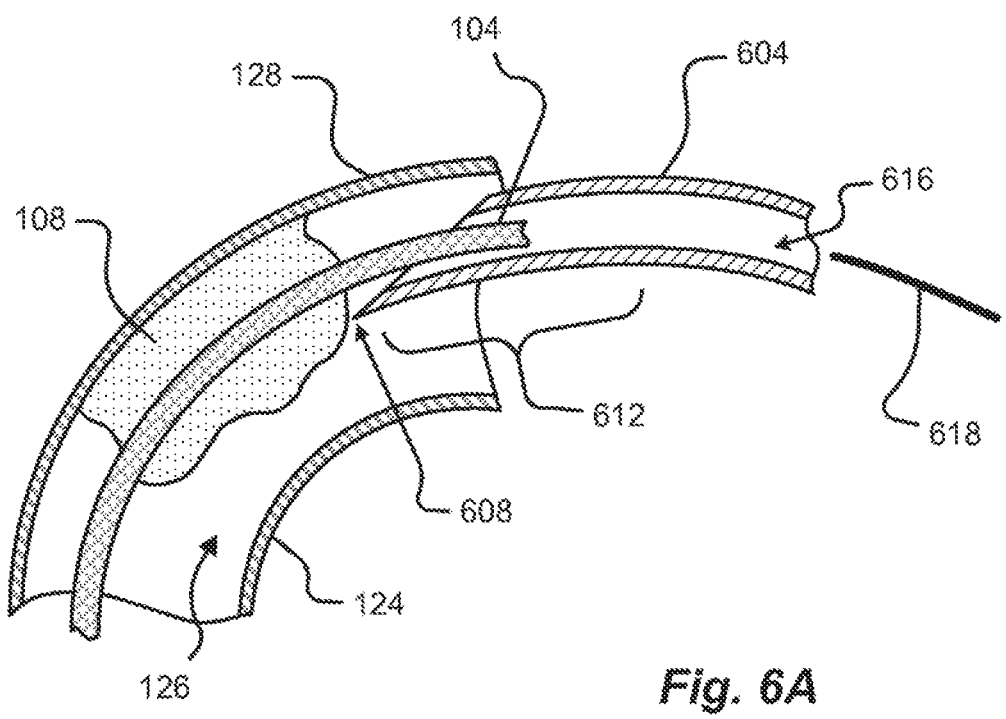
FIG. 6A shows a section view of a curved area of vasculature with a tissue slitting device first introduced in accordance with embodiments of the present disclosure.

FIG. 6A shows a section view of a curved area of vasculature with a tissue slitting device 604 first introduced in accordance with embodiments of the present disclosure. The tissue slitting device 604 is indexed into position via a directional force 618 adjacent to the tissue growth 108. The directional force 618 may be applied to the tissue slitting device 604 via one or more mechanical actuators, electrical actuators, manual positioning, and combinations thereof.

In some embodiments, the tissue slitting device 604 includes a flexible shaft having a proximal end, a distal end 612, and an internal lumen 616 having an internal diameter configured to allow a lead, lead locking device, and/or other implanted device to pass through it. The device may also include a tissue slitting tip 608 operatively attached to the distal end 612 of the flexible shaft. As can be appreciated, the slitting of formed tissue can be performed by at least one of cutting, drilling, slicing, stripping, chopping, sanding, grinding, planing, abrasion, high-pressure fluid, laser ablation, and combinations thereof. It is anticipated that the tissue slitting device 604 may be oriented within a patient via use of the flexible shaft and monitor, or a catheter-based system. In some cases, the tissue slitting device 604 may be positioned toward the center of the vasculature, and/or proximal to a non-traumatic leading edge, such that any sharp, or working, edge is caused to contact tissue growth 108 and not contact the vasculature (e.g., the tissue connected side 128 wall and the free side 124 wall of a vessel).

Additionally or alternatively, the tissue slitting tip 608 and effective slitting section of the tissue slitting device 604 may be biased against a lead 104 via spring force. In some embodiments, the tissue slitting device 604 may include a flexible portion configured to allow the tissue slitting device 604 to move as directed within a patient.

Figure 6B:
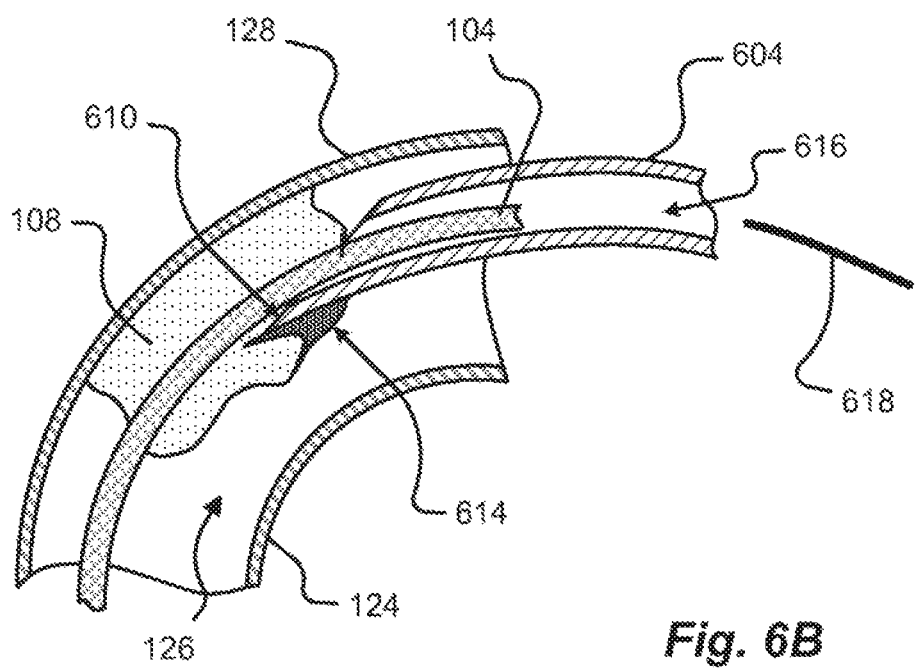
FIG. 6B shows a section view of a curved area of vasculature with a tissue slitting device in a first slitting position in accordance with embodiments of the present disclosure.

FIG. 6B shows a section view of a curved area of vasculature with a tissue slitting device 604 in a first slitting position in accordance with embodiments of the present disclosure. As the tissue slitting device 604 is directed into the tissue growth 108, the tissue slitting tip 608 causes the tissue growth 108 to separate along the engagement area 610. The separated tissue 614 allows the tissue slitting device 604 to be further engaged with the tissue growth 108. Additionally or alternatively, the separated tissue 604, by releasing forces containing the lead, can allow the lead 104 to be moved about the area of the tissue slitting tip 608.

Figure 6C:
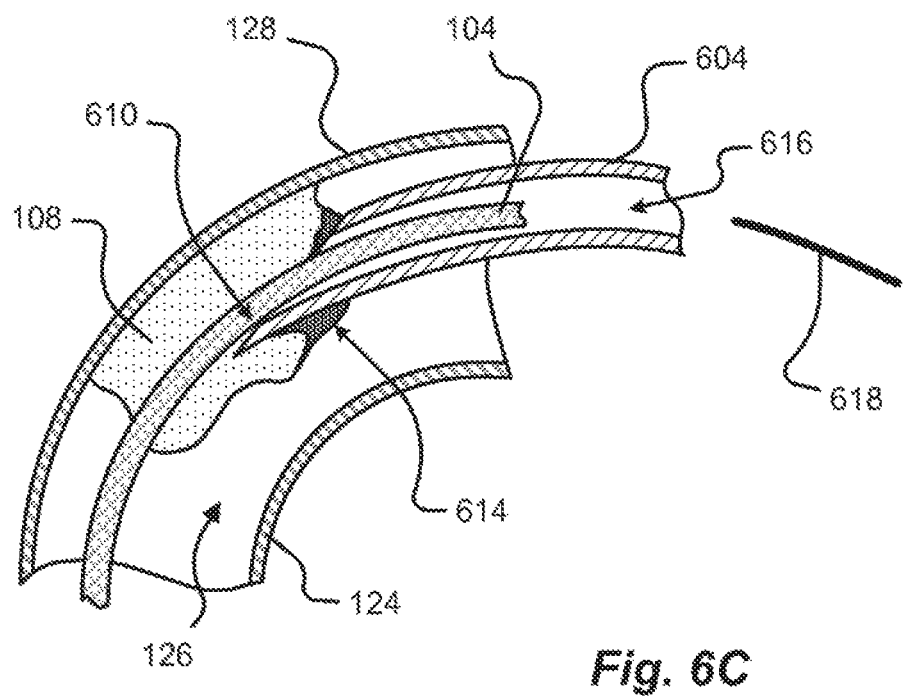
FIG. 6C shows a section view of a curved area of vasculature with a tissue slitting device in a second slitting position in accordance with embodiments of the present disclosure.

FIG. 6C shows a section of a curved area of vasculature with the tissue slitting device 604 in a second slitting position in accordance with embodiments of the present disclosure. As the tissue slitting device 604 is indexed in a direction 618 into the tissue growth 108 the tissue slitting device 604 separates tissue along an axial length of at least one side of the lead 104. In some embodiments, the lead 104 may be subjected to a traction force 120 that may be opposite to the index direction 618 of the tissue slitting device 604. This applied traction force 120 may assist in pulling the lead 104 away from the tissue growth 108 as the lead 104 is separated from containing tissue growth 108.

Figure 6D:
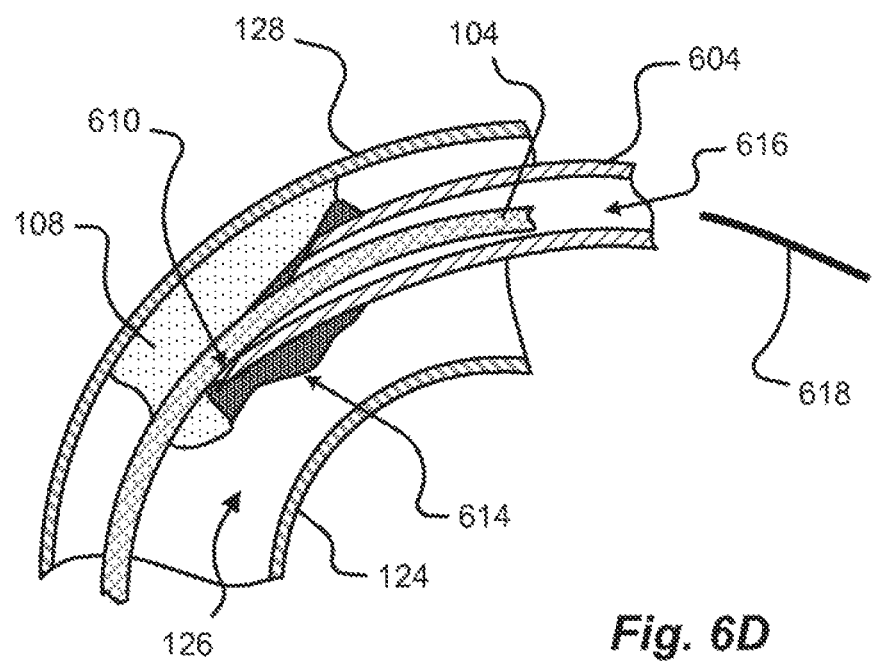
FIG. 6D shows a section view of a curved area of vasculature with a tissue slitting device in a third slitting position in accordance with embodiments of the present disclosure.

FIG. 6D shows a section view of a curved area of vasculature with a tissue slitting device 604 in a third slitting position in accordance with embodiments of the present disclosure. In general, the tissue slitting device 604 is indexed further into the tissue growth 108 such that the tissue growth 108 is almost completely separated from the lead 104 along a length of the tissue growth 108. In some embodiments, slitting at least a portion of the tissue growth 108 may allow the lead 104 to be removed in an explant procedure. For instance, the lead 104 may be subjected to a traction force 120 to pull the lead 104 away from any remaining the tissue growth 108. Additionally or alternatively, the lead 104 may be pulled against the remaining tissue growth 108 that surrounds the lead 104. In other embodiments, the tissue slitting device 604 may be indexed along the entire length of the tissue growth 108 to completely separate the tissue growth 108 from encapsulating, or surrounding, the lead 104.

Cutting Embodiments

Figure 9A:
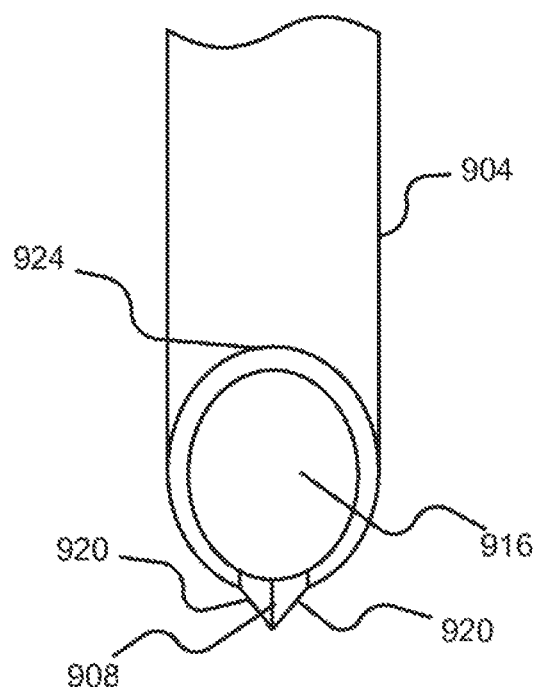
FIG. 9A shows a plan view of a tissue slitting device in accordance with embodiments of the present disclosure.
Figure 9B:
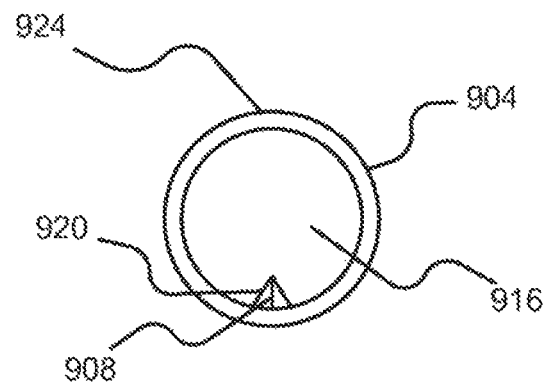
FIG. 9B shows an end view of a tissue slitting device in accordance with embodiments of the present disclosure.
Figure 10:
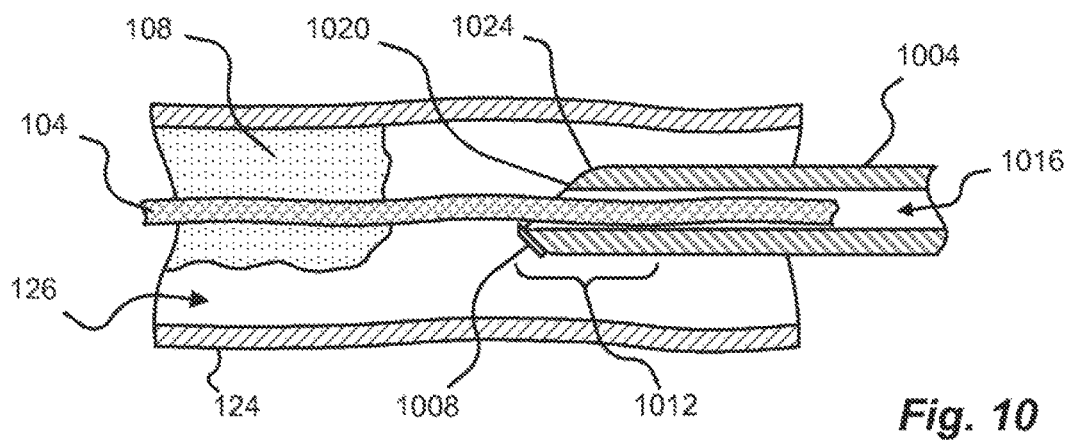
FIG. 10 shows a first embodiment of a tissue slitting device inside an area of vasculature having formed tissue surrounding an implanted lead in accordance with embodiments of the present disclosure.
Figure 11:
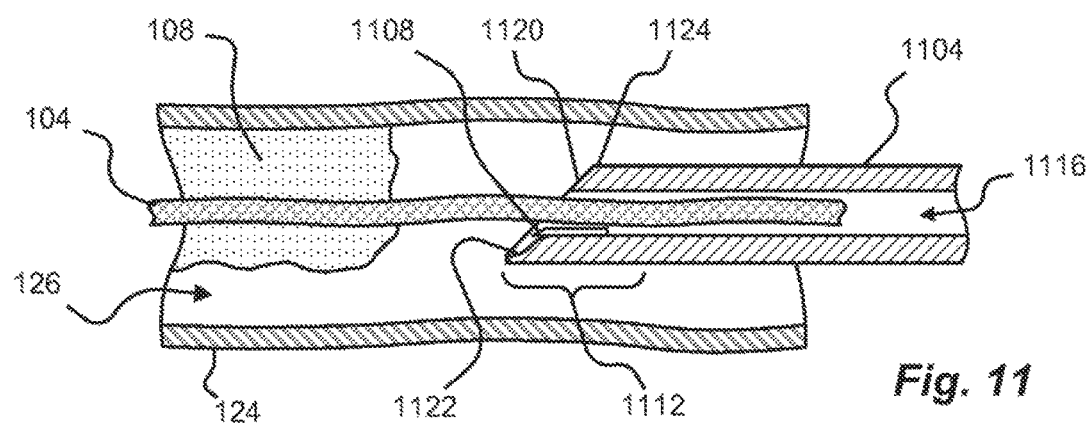
FIG. 11 shows a second embodiment of a tissue slitting device inside an area of vasculature having formed tissue surrounding an implanted lead in accordance with embodiments of the present disclosure.
Figure 12:
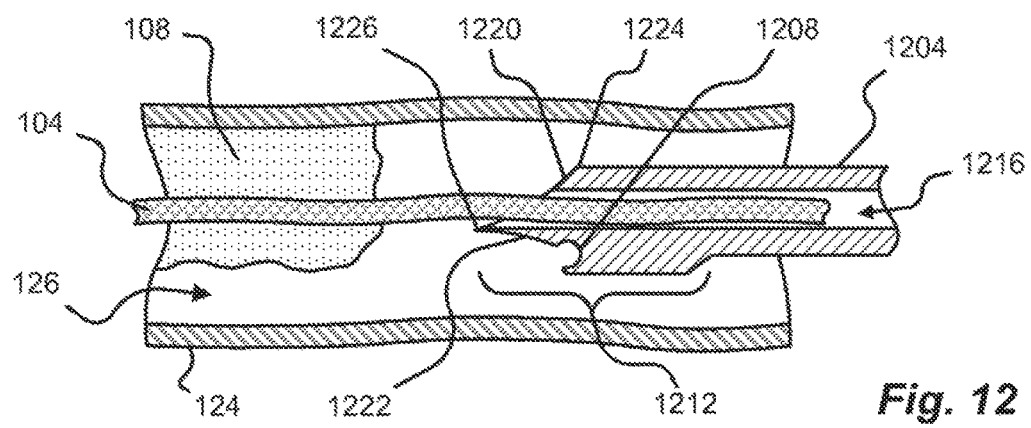
FIG. 12 shows a third embodiment of a tissue slitting device inside an area of vasculature having formed tissue surrounding an implanted lead in accordance with embodiments of the present disclosure.

FIGS. 7A-12 are directed to embodiments of a tissue slitting device that include one or more cutting features that are configured to cut at least a portion of a tissue growth 108 along a lead 104 implanted in a patient 102. FIGS. 10-12 show embodiments of the tissue slitting device inside an area of vasculature where an implanted lead 104 is encapsulated by a tissue growth 108. In addition to surrounding the lead 104 along a section, the tissue growth 108 is connected to a portion of the vessel wall.

In any of the embodiments disclosed herein the cutting surface may be guarded by a mechanical sheath. A mechanical sheath may include at least one surface that acts to guard and/or protect a cutting surface from being accidentally exposed to one or more sensitive areas of the vasculature during navigation of a tissue slitting device within a patient 102. In one embodiment, a mechanical sheath may at least partially shroud a portion of a cutting surface with a compliant material (e.g., silicone, polyurethane, rubber, polymer, combinations thereof, and the like). It is anticipated that the compliant material may be compressed when subjected to an operation force. The compression of the compliant material may subsequently expose the cutting surface of the tissue slitting device.

In another embodiment, the mechanical sheath may include a non-compliant material (e.g., metal, carbon fiber, plastic, resin, combinations thereof, and the like) that is configured to at least partially shroud a portion of a cutting surface. The non-compliant material mechanical sheath may be configured to at least partially shroud the cutting surface via a compliant member (e.g., spring, flexure, compliant material, combinations thereof, etc.) in connection with the non-compliant member that maintains a shrouded position of the non-compliant material mechanical sheath. Upon subjecting the non-compliant material mechanical sheath to au operational force, the operational force may be directed to the compliant member, which subsequently exposes the cutting surface from the mechanical sheath.

Figure 7A:
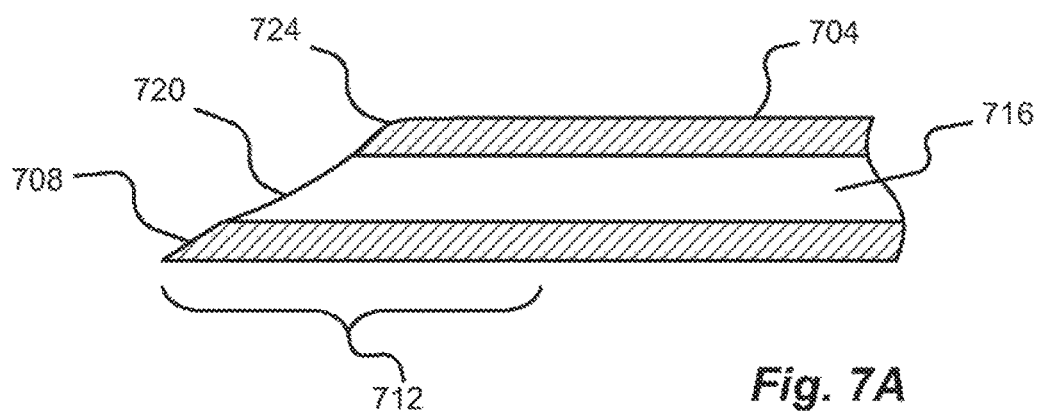
FIG. 7A shows a section view of a tissue slitting device in accordance with embodiments of the present disclosure.
Figure 7B:
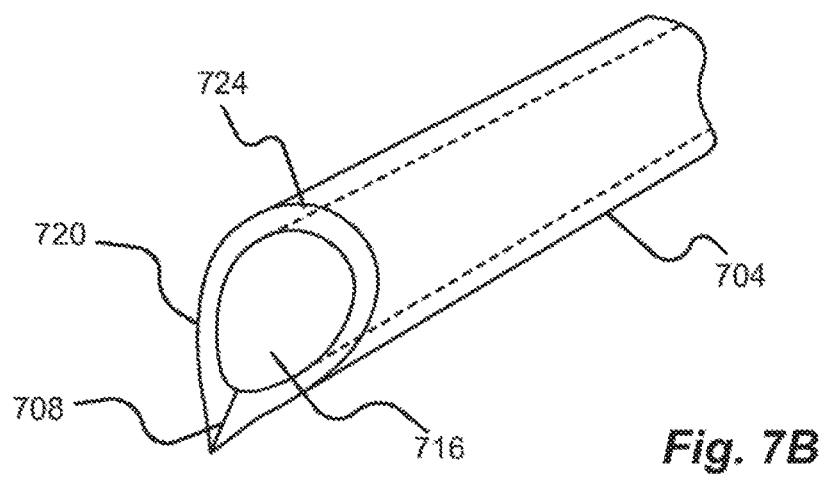
FIG. 7B shows a perspective view of the tissue slitting device of FIG. 7A.

Referring now to FIGS. 7A and 7B a tissue slitting device 704 is shown in accordance with embodiments of the present disclosure. In some embodiments, the tissue slitting device 704 comprises an inner lumen 716, at least one cutting surface, or knife-edge 708, a wedge tapered section 720, and a tapered section transition 724. The inner lumen 716 can be disposed between the proximal and distal end of the tissue slitting device 704. In some embodiments, the inner lumen 716 may be configured to allow a lead 104 and/or other objects to pass therethrough (e.g., a lead-locking device, traction device, snare tool. etc). As can be appreciated, the tissue slitting device 704 may be indexed and/or guided along the lead 104 via the inner lumen 716 of the device 704.

The tissue slitting device 704 may be configured to engage with the tissue growth 108 in a patient 102 at a distal tip 712 of the device 704. In some embodiments, the distal tip 712 of the device may be equipped with a knife-edge 708 configured to cut the tissue growth 108. Additionally, the knife-edge 708 may be configured to part the tissue as it cuts. In other words, the knife-edge 708 of the distal tip 712 may include a wedge shape 720. As the knife-edge 708 is moved into the tissue growth 108, the cutting surface of the knife-edge 708 may sever the tissue while simultaneously parting it along the wedge shape 720 of the device 704. In some embodiments, the wedge shape 720 may cause a parting of separated tissue and bias the cutting surface of the knife-edge 708 against remaining tissue growth 108 attached to the lead 104. Additionally or alternatively, the wedge shape 720 may be configured as a scalloped shape that can provide added strength to the structure of the distal tip 712 of the tissue slitting device 704.

In some embodiments, the distal tip 712 of the tissue slitting device 704 includes a knife-edge 708 disposed at the most distal portion of the tip 712 and a tapered wedge section 720 proximal to the knife-edge 708. The tapered wedge section 720 may be configured in one or more shapes designed to slope proximal from the knife-edge 708 distal end. The proximal end point of the tapered wedge section may include a smooth surface 724 that transitions from the tapered slope angle of the tip to the circumferential surface of the device 704. In some embodiments, the smooth surface 724 may include a radius joining the circumferential surface with the distal tip 712. The taper and/or radius may be configured to reduce trauma during navigation through the vasculature and/or during the cutting of tissue.

In any of the embodiments disclosed herein, the taper associated with the distal tip of the tissue slitting device may be configured with various shapes, angles, and dimensions. In one embodiment, the taper may be arranged at an angle ranging from 10 to 50 degrees from a plane that is coincident with at least two points on an axis running along the lumen of the tissue slitting device. As can be appreciated, the tapered section of the distal tip of the tissue slitting device may be defined by its axial length from the distal end. In one embodiment, the axial length of the tapered section of the distal tip may range from 0.025" to 0.500". In another embodiment, the axial length of the tapered section of the distal tip may range from 0.050" to 0.300".

Figure 8:
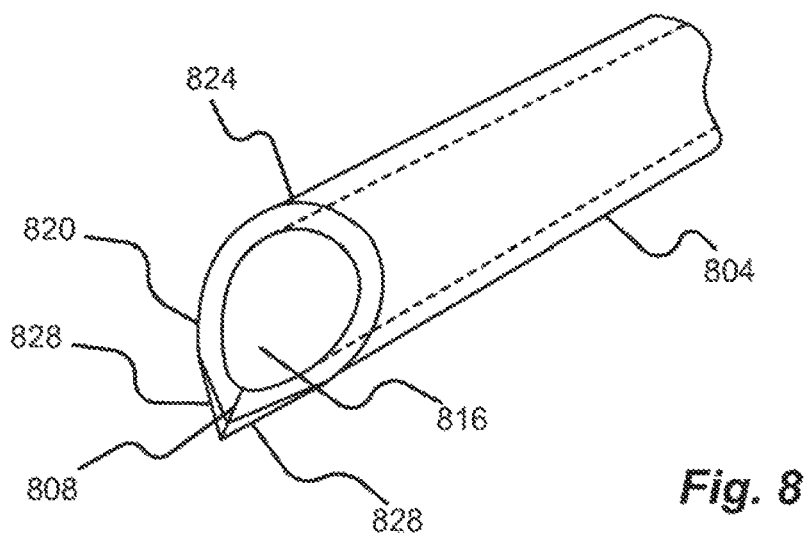
FIG. 8 shows a perspective view of a tissue slitting device in accordance with embodiments of the present disclosure.

FIG. 8 shows a perspective view of a tissue slitting device 804 in accordance with embodiments of the present disclosure. In some embodiments, the tissue slitting device 804 comprises an inner lumen 816, at least one cutting surface, or knife-edge 808, a tapered section 820, and a tapered section transition 824. The inner lumen 816 may be configured to allow a lead 104 and/or other objects to pass therethrough (e.g., a lead-locking device, traction device, snare tool, etc). As can be appreciated, the tissue slitting device 804 may be indexed and/or guided along the lead 104 via the inner lumen 816 of the device 804. In one embodiment, the knife-edge 808 may at least partially surround the leading edges 828 adjacent to the knife-edge 808 at the distal portion of the tissue slitting device 804. In other embodiments, the knife-edge 808 may completely surround the leading edges at the distal portion of the tissue slitting device 804. As can be appreciated, embodiments of the present disclosure anticipate including a sufficiently sharp portion of the knife-edge configured to slit tissue. For example, some leads 104, or implanted devices may include dual-coils, exposed coils, and/or other undulating geometry. As such, tissue may be caused to form in and/or around the coils/geometry. It is anticipated that a tissue slitting tip, or knife-edge 808, with an extended blade portion 828 disposed at least partially around its distal circumference may remove this additionally formed tissue growth 108.

FIGS. 9A and 9B show a tissue slitting device 904 showing various cutting surface locations in accordance with embodiments of the present disclosure. In some embodiments, the tissue slitting device 904 comprises an inner lumen 916, at least one cutting surface, or knife-edge 908, a tapered section 920, and a tapered section transition 924. As shown in FIG. 9A, it is anticipated that the knife-edge 908 may be disposed at a distal end of the tissue slitting device 904. In other words, the knife-edge 908 may be oriented at a leading edge of a tissue slitting device 904. In one embodiment, and as shown in FIG. 9B. the knife-edge 908 may be disposed at least partially inside the lumen 916 of the tissue slitting device 904.

Additionally, tissue slitting devices disclosed herein may include at least one fluorescing material or marker (e.g., radiopaque band, marker, and the like). In some embodiments, the radiopaque marker may be arranged about and/or adjacent to a knife-edge 908 of the tissue slitting device 904. The radiopaque marker, may assist in identifying a location of the knife-edge 908 via a monitoring device. Examples of radiopaque markers may include, but are in no way limited to, materials and/or particles containing tantalum, tungsten, carbide, iridium, bismuth oxide, barium sulfate, cobalt, platinum and/or alloys and combinations thereof. In some embodiments, the inner lumen 916 may be configured to allow a lead 104 and/or other objects to pass therethrough (e.g., a lead-locking device, traction device, snare tool, etc). As can be appreciated, the tissue slitting device 904 may be indexed and/or guided along the lead 104 via the inner lumen 916 of the device 904. Referring to FIG. 9B, a knife-edge 908 is oriented at least partially within the lumen 916 of the tissue slitting device 904, which may allow the device 904 to be routed through the vasculature of a patient 102 without presenting sharp edges, cutting surfaces, or knife-edges 908 toward sensitive areas. The knife-edge 908 oriented at least partially within the lumen 916 of the tissue slitting device 904 may allow the cutting surface of the knife-edge 908 to be biased toward the tissue growth 108 in connection with the lead 104. In another embodiment, the knife-edge 908 may be configured as a blade positioned perpendicular to the outer circumferential surface of the lead. The blade may be spring-loaded and/or arranged such that lead 104 is pushed against the blade when the tissue slitting device 904 is actuated along the axial length of the lead 104. Additionally, the blade may be equipped with a wedge 920 to peel the tissue away as it is being cut by the blade portion. Additionally or alternatively, the angle of the blade relative to the axis, and/or outer circumferential surface, of the lead 104 may be configured to achieve an adequate cutting angle in the tissue growth 108, such that the tissue 108 is slit in a manner to best achieve lead 104 removal. That is, due to the overall size of the lumen, a small angle itself may create a sharp leading edge sufficient to cut and slit the tissue growth 108. The angle may also create smooth translation and slitting of the remainder of the tissue as the tissue slitting device 904 traverses longitudinally along a direction of the lead 104.

Referring now to FIG. 10, a first embodiment of a tissue slitting device 1004 inside an area of vasculature having tissue growth 108 surrounding an implanted lead 104 is shown in accordance with embodiments of the present disclosure. In some embodiments, the tissue slitting device 1004 comprises an inner lumen 1016, at least one cutting surface 1008, a tapered section 1020, and a tapered section transition 1024. The inner lumen 1016 may be configured to allow a lead 104 and/or other objects to pass therethrough (e.g., a lead-locking device, traction device, snare tool, etc). As can be appreciated, the tissue slitting device 1004 maybe indexed and/or guided along the lead 104 via the inner lumen 1016 of the device 1004. In one embodiment, a cutting surface (e.g., a blade) 1008 may be disposed such that the cutting surface 1008 is tangent to an inner lumen, or opening, 1016 in the body/sheath of the tissue slitting device 1004 (e.g., similar to a planing blade). As can be appreciated, the cutting surface 1008 may be arranged at an angle at the leading edge of the tissue slitting device 1004. The angle may be configured to present the cutting surface in the direction of formed tissue that is distally adjacent to the tip of the tissue slitting device 1004. As the device 1004 is further engaged with the tissue growth 108, the planing-style blade 1008 may be configured to remove a section of tissue 108 along at least one of a length arid width of a lead 104.

FIG. 11 shows a second embodiment of a tissue slitting device 1104 inside an area of vasculature having tissue growth 108 surrounding an implanted lead 104 in accordance with embodiments of the present disclosure. In some embodiments, the tissue slitting device 1104 comprises an inner lumen 1116, at least one knife-edge 1408, a wedge and/or ramp 1122, a tapered section 1120, and a tapered section transition 1124. The inner lumen 1116 may be configured to allow a lead 104 and/or other objects to pass therethrough (e.g., a lead-locking device, traction device, snare tool, etc). As can be appreciated, the tissue slitting device 1104 may be indexed and or guided along the lead 104 via the inner lumen 1116 of the device 1104. The knife-edge 1108 may include a blade that is positioned tangent to the outer circumferential surface of the lead 104. The blade may be spring-loaded and/or arranged such that the lead 104 is pushed against the blade when the tissue slitting device 1104 is actuated along the axial length of the lead 104. Additionally, the knife-edge 1108, or blade, may be equipped with a wedge, or ramp, 1120 to part the tissue as it is being cut by the blade. As can be expected, the angle of the blade relative to the axis of the lead 104 may be configured to achieve an adequate stripping of tissue growth 108 in a specific area, such that the tissue 108 is slit at the specific area.

In some embodiments, the knife-edge 1108 may be mechanically actuated to assist in cutting tissue growth 108. For instance, the knife-edge 1108 may be configured to move along an axis defined by at least one sharp edge of the knife-edge 1108. Actuation of the knife-edge 1108 may be achieved via a mechanism operatively connected to the knife-edge 1108 that can move the blade from one direction along the axis defined by at least one sharp edge to the opposite direction along the axis defined by the at least one sharp edge. This oscillating movement may be made at a sub-ultrasonic frequency. Additionally or alternatively, the oscillating blade may move at. an ultrasonic frequency. In one embodiment, the frequency of oscillation of the knife-edge 1108 may be adjusted to suit preferences of the operator.

In another embodiment, the knife-edge 1108 may be configured to move along an axis that is perpendicular to an axis created by the at least one sharp edge of the knife-edge 1108. In other words, the knife-edge 1108 may be configured to move from a proximal position to a distal position along the axis of the tissue slitting device 1104. As can be appreciated, the movement of the knife-edge 1108 may be actuated to repetitively move from the proximal position to the distal position and back to the proximal position. This oscillating movement may be made at a sub-ultrasonic frequency. Additionally or alternatively, the oscillating blade may move at an ultrasonic frequency. In one embodiment the frequency of oscillation of the knife-edge 1108 may be adjusted to suit preferences of the operator.

FIG. 12 shows a third embodiment of a tissue slitting device 1204 inside an area of vasculature having formed tissue growth 108 surrounding an implanted lead 104 in accordance with embodiments of the present disclosure. In some embodiments, the tissue slitting device 1204 comprises an inner lumen 1216, at least one cutting surface 1208, a tapered section 1220, a tapered section transition 1224, and a tissue tension taper 1222. The inner lumen 1216 may be configured to allow a lead 104 and/or other objects to pass therethrough (e.g., a lead-locking device, traction device, snare tool, etc). As can be appreciated, the tissue slitting device 1204 may be indexed and/or guided along the lead 104 via the inner lumen 1216 of the device 1204. In one embodiment, the cutting surface 1208 of the tissue slitting device 1204 may be oriented proximal to the leading edge 1226 of the distal tip 1212 of the tissue slitting device 1204. The cutting surface 1208 may be arranged such that any sharp edge is concealed behind a smooth and/or dull surface. This arrangement can allow the tissue slitting device 1204 to be safely routed within a convoluted vasculature of a patient 102. Additionally or alternatively, the tapered surfaces 1220, 1222 of the leading edge 1226 allows the tissue growth to be stretched as it is engaged and presented to the cutting surface. As disclosed herein, the stretching of the tissue growth 108 fibers assists in the cutting operation performed by the tissue slitting device 1204. Among other things, the tension placed on the tissue growth 108 fibers provide a taught area for the cutting surface 1208 to engage and cut along. In some embodiments, the leading edge 1226 of the distal tip 1212 of the tissue slitting device 1204 may comprise a non-traumatic surface. For example, the leading edge 1226 may include a non-traumatic surface where at least some of the exposed sharp edges have been removed (e.g., a ball end, radiused surface, other curved section, etc.). Additionally or alternatively, the tapered surface 1222 may include a cutting surface. For instance, as the tapered surface 1222 wedges into and engages a tissue growth 108, it may simultaneously cut the tissue along the tapered surface 1222 as it stretches the fibers of the tissue growth 108.

In accordance with embodiments of the present disclosure, the knife-edge 708, 808, 908, 1008, 1108, 1208 may be advanced into the tissue growth 108. This advancement may be continuous or periodic. Additionally or alternatively, the knife-edge 708, 808, 908, 1008, 1108, 1208 may be actuated in a direction toward and away from the tissue such that the knife-edge 708, 808, 908, 1008, 1108, 1208 is presented to an area of the tissue growth 108, removed from the area, and represented to an area of the tissue growth 108 to successively cut the tissue growth 108 over a number of movements. For example, the tissue growth 108 is cut in a similar manner to that of an axe chopping at a tree. In any embodiment disclosed herein, traction force may be applied to the lead 104 during the cutting of the tissue growth 108. Among other things, traction force 120 can prevent tears, punctures, and other catastrophic failures caused by the force exerted on the tissue growth and/or adjacent vasculature by the tissue slitting device 704, 804, 904, 1004, 1104, 1204.

It is anticipated that the knife-edge may be manufactured from a material with a suitable hardness for slitting tissue. In some embodiments, the knife-edge 708, 808, 908, 1008, 1108, 1208 may be manufactured from a polymeric material with a durometer configured to cut a patient's tissue. Examples of polymeric material may include, but are not limited to, plastics, silicone, polytetrafluoroethylene ("PTFE"), polyethylene, polyurethane, polycarbonate, polypropylene, polyvinyl chloride ("PVC"), polystyrene, acetal, polyacetal, acetal resin, polyformaldehyde, and the like. In one embodiment, the knife-edge 708, 808, 908, 1008, 1108, 1208 may be constructed from a crystalline or amorphous metal alloy. The knife-edge 708, 808, 908, 1008, 1108, 1208 may comprise at least a portion of the distal tip of the tissue slitting device 704, 804, 904, 1004, 1104, 1204. As can be appreciated, the knife-edge 708, 808, 908, 1008, 1108, 1208 may comprise a metal insert. Examples of knife-edge 708, 808, 908, 1008, 1108, 1208 metals may include, but are not limited to, steel, stainless steel (e.g., austenitic type 304, 316, martensitic type 420, 17-4, etc.), aluminum, titanium, tungsten carbide, silver, platinum, copper, and combinations thereof. In one embodiment, the metal may be hardened to, among other things, maintain a sharp edge during the tissue slitting process.

Additionally or alternatively, the knife-edge 708, 808, 908, 1008, 1108, 1208 or cutting surface may be removably attached to the distal tip of the tissue slitting device 704, 804, 904, 1004, 1104, 1204. Benefits of a removably attached knife-edge 708, 808, 908, 1008, 1108, 1208 allow for quick replacement of cutting surfaces during lead removal procedures. As can be appreciated, the replacement of the cutting surface may be initiated upon detecting that the cutting surface is dulling. In some cases the cutting surface may be replaced with a different style of blade. The style of blade may be configured to suit a number of desires, including but not limited to, navigating difficult areas in a patient (e.g., using a curved blade, etc.), cutting difficult, dense, and/or hard tissue (e.g., using a serrated blade, a hardened blade, and combinations thereof, etc.), cutting tissue in confined and/or low-growth areas (e.g., using a miniature blade), and even removing the blade completely (e.g., using the tissue slitting device as a counter-traction sheath, etc.).

In some embodiments, the tissue slitting devices disclosed herein may include at least one non-traumatic leading edge disposed at the most distal end of the device. The non-traumatic leading edge may include a distal end and a proximal end. Non-traumatic surfaces on the leading edge of the device may include but are not limited to, spheroidal, ball-nose, radiused, smooth, round, and/or other shapes having a reduced number of sharp edges. These non-traumatic surfaces may be configured to prevent accidental puncture or harmful contact with the patient 102. The non-traumatic leading edge may be configured to include a tapered and/or a wedge-shaped portion. In some cases the cross-sectional area of the tapered portion increases along a length of the non-traumatic leading edge from the distal end to the proximal end of the leading edge. A knife-edge and/or cutting surface may be disposed proximal to or along the tapered portion of the non-traumatic leading edge of the tissue slitting device.

The non-traumatic leading edge may be positioned to insert into an area between the tissue growth 108 and the implanted lead 104. In some cases the tapered geometry and the arrangement of the tissue slitting device tip may allow the most distal portion of the non-traumatic leading edge to bias against the lead 104 and wedge under any surrounding tissue growth 108. As the non-traumatic leading edge is indexed further into the tissue growth 108, the tissue growth is caused to stretch and pull away from the lead 104. Once the non-traumatic leading edge is engaged with the tissue growth 108, the cutting surface of the tissue slitting device may be caused to slit the tissue along a length of the tissue growth. As can be appreciated, the cutting surface may include but is not limited to one or more knife-edge and/or cutting devices disclosed herein.

Actuated Slitting Embodiments

Figure 13:
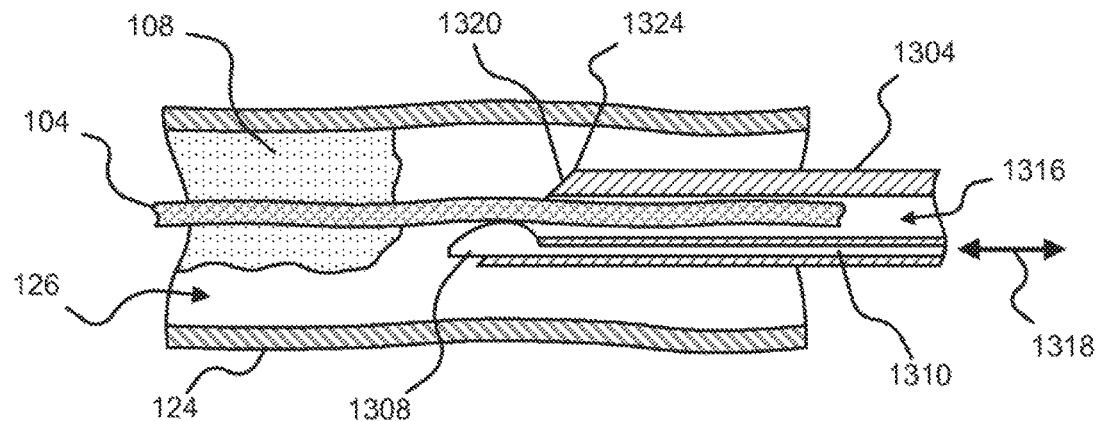
FIG. 13 shows a fourth embodiment of a tissue slitting device inside an area of vasculature having formed tissue surrounding an implanted lead in accordance with embodiments of the present disclosure.

FIG. 13 shows a fourth embodiment of a tissue slitting device 1304 inside an area of vasculature having formed tissue growth 108 surrounding an implanted lead 104 in accordance with embodiments of the present disclosure. In some embodiments, the tissue slitting device 1304 comprises an inner lumen 1316, at least one reciprocating cutting blade 1308, a reciprocating blade actuation element 1310, a tapered section 1320, and a tapered section transition 1324. The inner lumen 1316 may be configured to allow a lead 104 and/or other objects to pass therethrough (e.g., a lead-locking device, traction device, snare tool, etc). As can be appreciated, the tissue slitting device 1304 may be indexed and/or guided along the lead 104 via the inner lumen 1316 of the device 1304. In one embodiment, the knife-edge may be configured as a reciprocating blade 1308. In other words, the knife-edge may be configured to move back-and-forth in an axial direction 1318. This actuation may be independent of the movement of the outer shaft of the device 1304. The reciprocating motion of the blade 1308 may be achieved via a reciprocating actuator that is operatively connected proximal to the distal tip. The reciprocating actuator may be an electrical motor that is located at the proximal end of the flexible shaft. In some embodiments, the reciprocating actuator may be manually operated via a mechanical movement at the proximal end of the flexible shaft. In any event, energy from the actuator may be transferred to the blade 1308 via an actuation element 1310. It is anticipated that the actuation element 1310 may comprise one or more of a shaft, rod, bar, link, and the like, that is configured to transmit force from the proximal end of the tissue slitting device 1304 to the blade 1308.

In one embodiment, the reciprocating blade 1308 may be configured to move a cutting surface horizontal to the central axis of the tissue slitting device. In other words, rather than reciprocating along an axis of the tissue slitting device, as previously disclosed, the reciprocating blade in this embodiment may operate across (or side-to-side) the distal tip of the tissue slitting device. Additionally or alternatively, the actuation of the blade 1308, whether axial or side-to-side, may be provided at a frequency below 20 kHz. In some embodiments, the actuation frequency of the blade 1308 may exceed 20 kHz (e.g., ultrasonic range). In either case, it is anticipated that the actuation frequency of the blade 1308 may be adjusted higher or lower to suit a cutting application (e.g., index speed, tissue type, operator preference, and the like).

In accordance with embodiments of the present disclosure, the blade 1308, or other cutting surface, may be deployed from within a shaft of the tissue slitting device 1308. Additionally or alternatively, any tissue slitting member (e.g., cutting tip, grinding tips, laser ablation, RF cutting, pressurized fluid cutters) may be shielded. Accordingly, any sharp or working members may be concealed from exposure to the patient 102 and/or vasculature, during navigation to a tissue growth 108 site. This concealment and/or shielding may act to prevent damage to a patient 102. As can be appreciated, any of the tissue slitting devices disclosed herein may utilize a deployable and/or shielded slitting member.

Figure 14A:
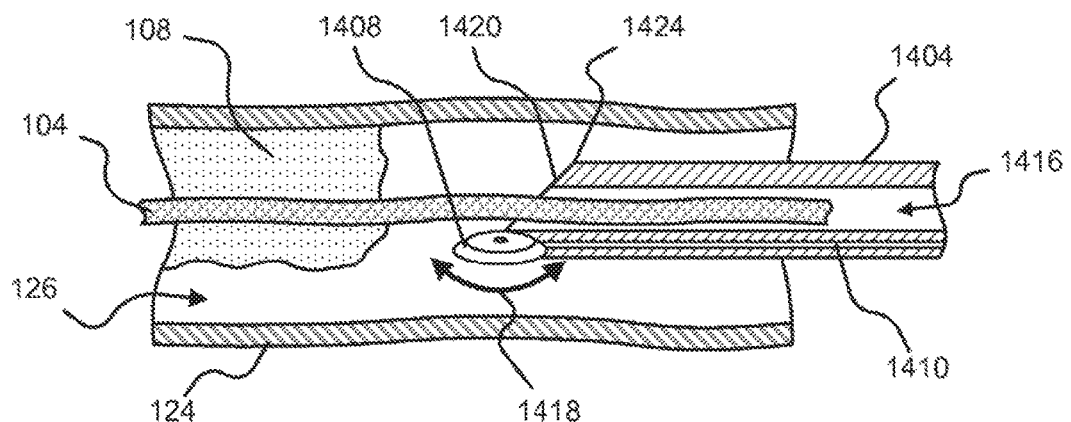
FIG. 14A shows a first configuration of a fifth embodiment of a tissue slitting device inside an area of vasculature having formed tissue surrounding an implanted lead in accordance with embodiments of the present disclosure.
Figure 14B:
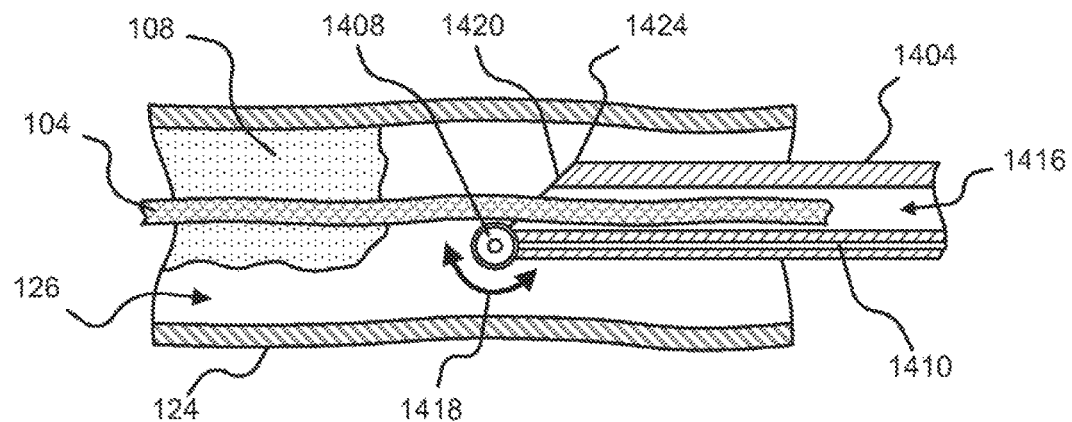
FIG. 14B shows a second configuration of the fifth embodiment of a tissue slitting device inside an area of vasculature having formed tissue surrounding an implanted lead in accordance with embodiments of the present disclosure.

FIGS. 14A and 14B show a disk-style tissue slitting device 1404 inside an area of vasculature in accordance with embodiments of the present disclosure. In some embodiments, the tissue slitting device 1404 comprises an inner lumen 1416, at least one disk-style cutting blade 1408, a disk-style cutting blade actuation element 1410, a tapered section 1420, and a tapered section transition 1424. The inner lumen 1416 may be configured to allow a lead 104 and/or other objects to pass therethrough (e.g., a lead-locking device, traction device, snare tool, etc). As can be appreciated, the tissue slitting device 1404 may be indexed and/or guided along the lead 104 via the inner lumen 1416 of the device 1404. As shown, the disk-style cutting blade 1408 can move in one or more rotational direction 1418. In some embodiments, the disk-style cutting blade 1408 may rotate continually in one direction, while actuated. For example, the actuation element 1410 may be operatively connected to the disk-style cutting blade 1408 at a point that is off of the axis of revolution of the blade 1408. By moving the actuation element 1410 axially in this example the off-axis motion could engender rotation about a fixed axis of revolution. Alternatively, the actuation element 1410 may be an electrical connection to a power source at the proximal end of the tissue slitting device 1404. In this example, the disk-style cutting blade 1408 may include a motor at the distal end that is operatively attached to the blade 1408 and is powered by a power source connected to the electrical connection.

In other embodiments, the disk-style cutting blade 1408 may repeatedly alternate directions of rotation (e.g., from a clockwise to a counterclockwise direction, and so forth). When the cutting blade 1408 is engaged with a tissue growth 108, and actuated, the disk-style cutting blade may cause at least a partial slit in the engaged tissue growth 108.

Referring to FIG. 14A, the disk-style cutting blade 1408 may be oriented such that the cutting surface of the blade 1408 is maintained substantially parallel with the outer surface of the lead 104 during cutting and engagement with a tissue growth 108. In some embodiments, the angle of the disk-style cutting blade 1408 may be arranged such that an obtuse angle is formed between a plane that is coincident with the lead axis 104 and a non-cutting surface of the disk-style cutting blade 1408. Orienting the disk-style cutting blade 1408 at an angle to the tissue growth 108 may assist in the cutting of at least one slit in the tissue growth 108 formed around the lead 104.

FIG. 14B shows the disk-style cutting blade 1408 oriented such that the cutting surface of the blade 1408 is maintained substantially perpendicular to the outer surface of the lead 104 during cutting and engagement with a tissue growth 108. In some embodiments, the disk-style cutting blade 1408 may not be connected to a power source via the actuation element 1410. In this case, the cutting blade 1408 may be free to rotate about a fixed axis of revolution and as such may be presented to the tissue growth 108 and engaged further into the growth 108 to create a slit in the tissue 108.

Figure 15A:
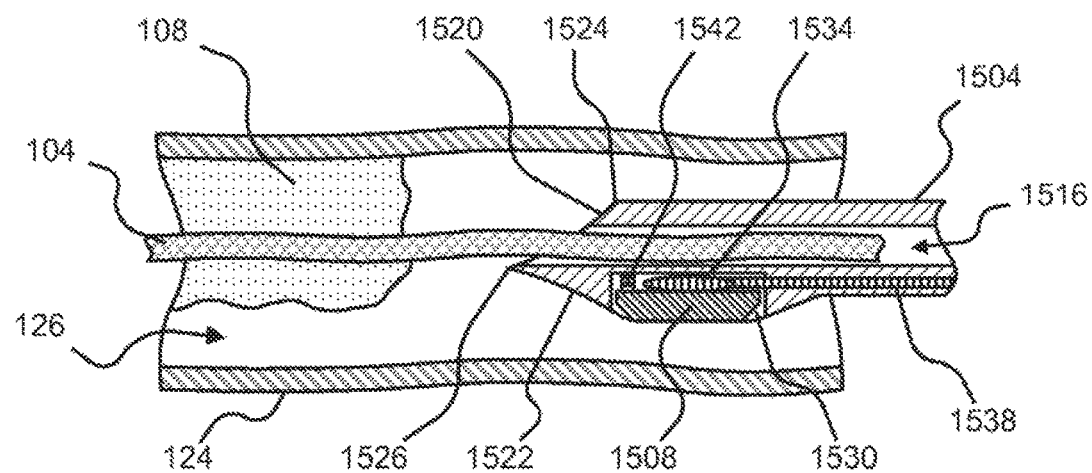
FIG. 15A shows a first configuration of a sixth embodiment of a tissue slitting device inside an area of vasculature having formed tissue surrounding an implanted lead in accordance with embodiments of the present disclosure.
Figure 15B:
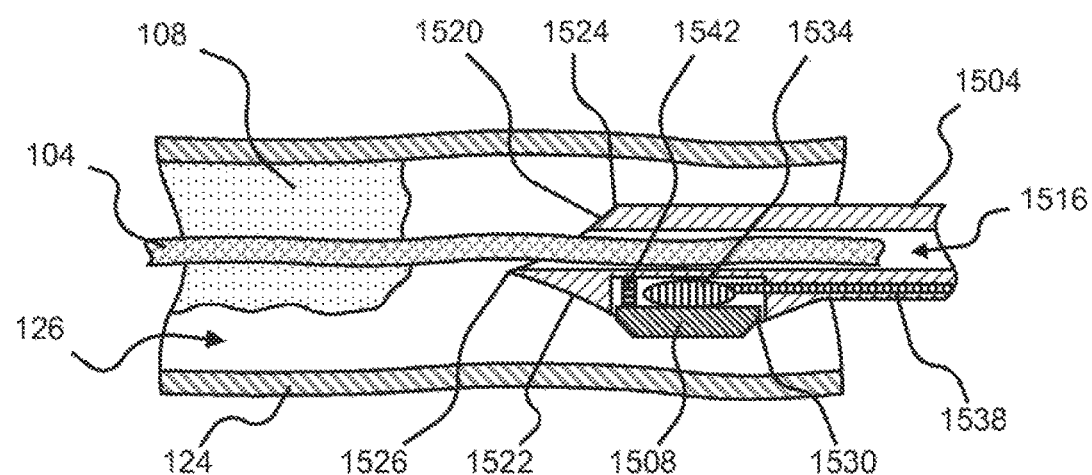
FIG. 15B shows a second configuration of a sixth embodiment of a tissue slitting device inside an area of vasculature having formed tissue surrounding an implanted lead in accordance with embodiments of the present disclosure.

FIGS. 15A and 15B show a deployable cutting element tissue slitting device 1504 inside an area of vasculature in accordance with embodiments of the present disclosure. In some embodiments, the tissue slitting device 1504 comprises an inner lumen 1516, at least one deployable cutting element 1508, a leading edge 1526, a tapered section 1520, a tapered section transition 1524, a tissue tension taper 1522, a cutout 1530, a deployment element 1534 connected to an actuation element 1538, and a cutting element retaining member 1542. The inner lumen 1516 may be configured to allow a lead 104 and/or other objects to pass therethrough (e.g., a lead-locking device, traction device, snare tool. etc). As can be appreciated, the tissue slitting device 1504 may be indexed and/or guided along the lead 104 via the inner lumen 1516 of the device 1504.

In some embodiments, the tissue slitting device 1504 may include a section having a concealed blade or deployable cutting surface. The leading edge 1526 may incorporate a tapered non-traumatic leading edge disposed at the distal most end of the tissue slitting device 1504, as previously disclosed. Additionally or alternatively, one or more features of the tissue slitting device 1504 may be configured to wedge in between the tissue growth 108 and the lead 104. In some embodiments, the tissue slitting device 1504 may include a slot, cutout, keyway, opening, or other volume 1530, housing a cutting surface 1508. In one embodiment the cutting surface 1508 may be operatively attached to a deployment element 1534 that is configured to deploy and/or conceal the cutting surface 1508 upon receiving an input directing an actuation. As can be appreciated, the deployment element 1534 may comprise, but is not limited to, one or more of, a balloon, a ramp, a screw, a wedge, an expansible member, a cam-operated lever, a lever, a cam, and combinations thereof. For example, the tissue slitting device 1504 may be oriented into a position, such that the leading edge 1526 of the tissue slitting device 1504 engages with a tissue growth 108. Once engaged, an operator may deploy the cutting surface 1508 of the tissue slitting device 1504 from a concealed position (see, e.g., FIG. 15A) by actuating the deployment element 1534 via the actuation element 1538. When the cutting surface 1508 is deployed (see, e.g., FIG. 15B), the tissue slitting device 1504 may be indexed further along the lead 104 and into the formed tissue 108. While the cutting surface 1508 is deployed and indexed along the lead 104, the formed tissue 108 is slit along a length adjacent to the cutting surface 1508. This arrangement offers the additional benefit of navigating the cutting surface 1508 (and any sharp and/or hardened blade) inside a patient in a safe collapsed, retracted, concealed, and/or undeployed, state.

In one example, the cutting element 1508 may be deployed by actuating a balloon operatively connected to the cutting element 1508. In other words, in this example, the deployment element 1534 may comprise a balloon, while the actuation element 1538 may comprise a lumen configured to convey a fluid (e.g., gas or liquid) suitable to inflate the balloon and extend the cutting element 1508. In some embodiments, the cutting element may be retained in the cutout 1530 via a retaining member 1542. For instance, the retaining member may include a spring connected to the tissue slitting device 1504 (e.g., at the cutout 1530) and the cutting member 1508. Additionally or alternatively, the retaining member 1542 may assist in returning the cutting element 1508 to a retracted, or concealed, state. In the case of a spring, the retaining member 1542 may exert a force on the cutting element 1508 to resist deployment without sufficient actuation via the deployment element 1534.

In another example, the cutting element 1508 may be deployed via a cam element operatively connected to the cutting element 1508. The cam element may be actuated via a rotation or other movement of the actuation element 1538 that is connected to the cam element. In this case, the retaining member 1542 may include a cam groove, guide, raceway, combinations thereof, or other combination of elements to direct and retain the cutting member 1508.

Grinding Embodiments

Figure 16:
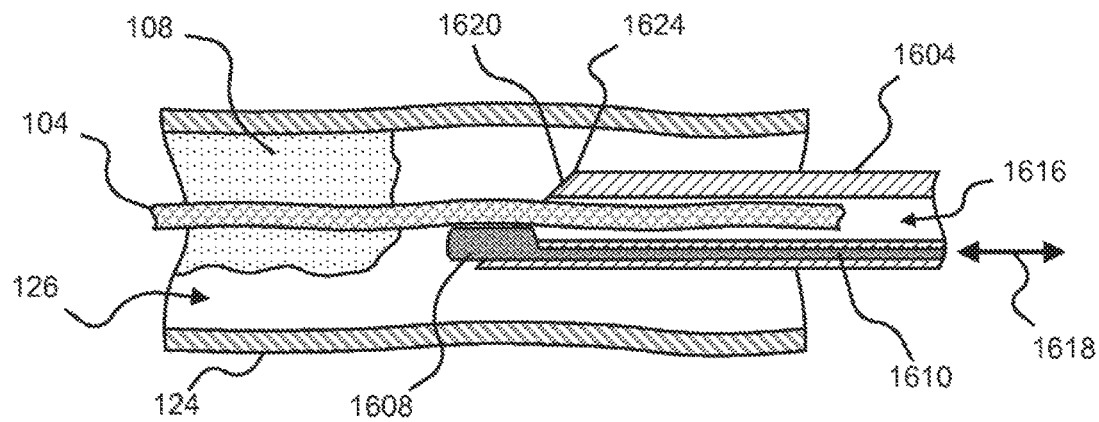
FIG. 16 shows a seventh embodiment of a tissue slitting device inside an area of vasculature having formed tissue surrounding an implanted lead in accordance with embodiments of the present disclosure.

Referring to FIG. 16, au embodiment of a tissue slitting device 1604 inside an area of vasculature having formed tissue 108 surrounding an implanted lead 104 in accordance with embodiments of the present disclosure. In some embodiments, the tissue slitting device 1604 comprises an inner lumen 1616, at least one reciprocating grinder 1608, a reciprocating grinder actuation element 1610, a tapered section 1620, and a tapered section transition 1624. The inner lumen 1616 may be configured to allow a lead 104 and/or other objects to pass therethrough (e.g., a lead-locking device, traction device, snare tool, etc). As can be appreciated, the tissue slitting device 1604 may be indexed and/or guided along the lead 104 via the inner lumen 1616 of the device 1604. In one embodiment, the reciprocating grinder 1608 may be configured to move back-and-forth in an axial direction 1618. This actuation may be independent of the movement of the outer shaft of the device 1604. The reciprocating motion of the grinder 1608 may be achieved via a reciprocating actuator that is operatively connected proximal to the distal tip. The reciprocating actuator may be an electrical motor that Is located at the proximal end of the flexible shaft. In some embodiments, the reciprocating actuator may be manually operated via a mechanical movement at the proximal end of the flexible shaft connected to the tissue slitting device 1604. In any event, energy from the actuator may be transferred to the grinder 1608 via an actuation clement 1610. It is anticipated that the actuation element 1610 may comprise one or more of a shaft, rod, bar, link, and the like, that is configured to transmit force from the proximal end of the tissue slitting device 1604 to the grinder 1608.

In one embodiment, the reciprocating blade 1608 may be configured to move a grinding surface horizontal to the central axis of the tissue slitting device 1604. In other words, rather than reciprocating along an axis of the tissue slitting device 1604, as previously disclosed, the reciprocating grinder in this embodiment may operate across (or side-to-side) the distal tip of the tissue slitting device 1604. Additionally or alternatively, the actuation of the grinder 1608, whether axial or side-to-side, may be provided at a frequency below 20 kHz. In some embodiments, the actuation frequency of the grinder 1608 may exceed 20 kHz (e.g., ultrasonic range). In either case, it is anticipated that the actuation frequency of the grinder 1608 may be adjusted higher or lower to suit a cutting application (e.g., index speed, tissue type, operator preference, and the like).

In some embodiments, the tissue slitting device 1604 may include a grinder disposed at the distal tip of the device 1604. The grinder 1608 may be configured to slit the formed tissue 108 by subjecting the tissue 108 to a moving abrasive surface. In one embodiment, the grinder 1608 may include a grinding tip located at the distal tip of the device 1604. The grinder 1608 may include an abrasive surface disposed on at least one surface that is caused to contact formed tissue 108 on a given side of the lead 104. The grinder 1608 may be engaged with the tissue growth 108 where the grinder 1608 emaciates the formed tissue 108 until the tissue 108 is slit at the point of contact with the grinder 1608. In any of the embodiments disclosed herein, the grinding or abrasive surface may include at least one rough surface, knurl, machined/formed metal, abrasive surface, diamond deposition, and combinations thereof and the like.

Figure 17:
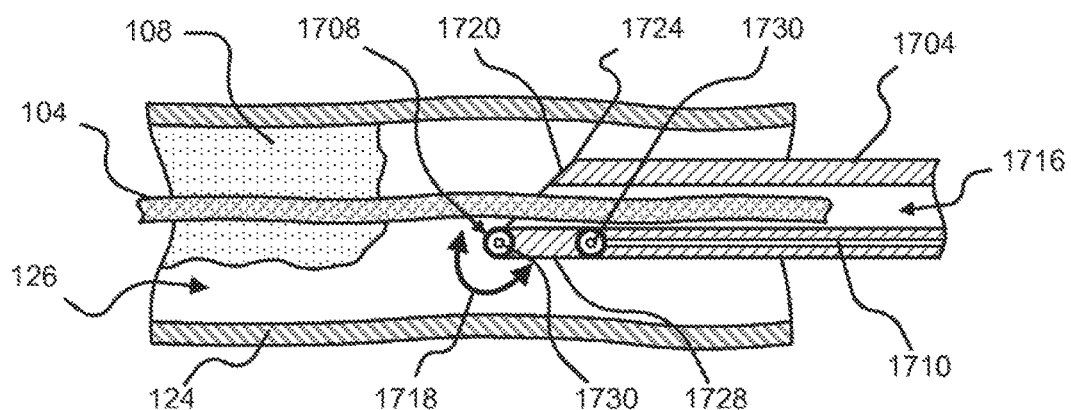
FIG. 17 shows a eighth embodiment of a tissue slitting device inside an area of vasculature having formed tissue surrounding an implanted lead in accordance with embodiments of the present disclosure.

Referring to FIG. 17, an embodiment of a tissue slitting device 1704 inside an area of vasculature having formed tissue 108 surrounding an implanted lead 104 in accordance with embodiments of the present disclosure. In some embodiments, the tissue slitting device 1704 comprises an inner lumen 1716, at least one grinding mechanism 1708 comprising an abrasive element 1728 and at least one roller 1730, an actuation element 1710, a tapered section 1720, and a tapered section transition 1724. The inner lumen 1716 may be configured to allow a lead 104 and/or other objects to pass therethrough (e.g., a lead-locking device, traction device, snare tool, etc). As can be appreciated, the tissue slitting device 1704 may be indexed and/or guided along the lead 104 via the inner lumen 1716 of the device 1704.

As shown, the grinding mechanism 1708 can move in one or more rotational direction 1718. In some embodiments, the grinding mechanism 1708 may rotate continually in one direction, while actuated. For example, the actuation element 1710 may be operatively connected to the at least one roller 1730 to turn the abrasive element 1728. By turning the at least one roller 1730 and the abrasive element 1728 the grinding mechanism 1708 may emaciate tissue it engages at the distal tip of the tissue slitting device 1704. Alternatively, the actuation element 1710 may be an electrical connection to a power source at the proximal end of the tissue slitting device 1704. In this example, the grinding mechanism 1708 may include a motor at the distal end that is operatively attached to the at least one roller 1730 and is powered by a power source connected to the electrical connection.

In other embodiments, the at least one roller 1730 may repeatedly alternate directions of rotation (e.g., from a clockwise to a counterclockwise direction, and so forth). When the abrasive element 1728 is engaged with a tissue growth 108, and actuated, the abrasive element 1728 may cause at least a partial slit in the engaged tissue growth 108.

Figure 18:
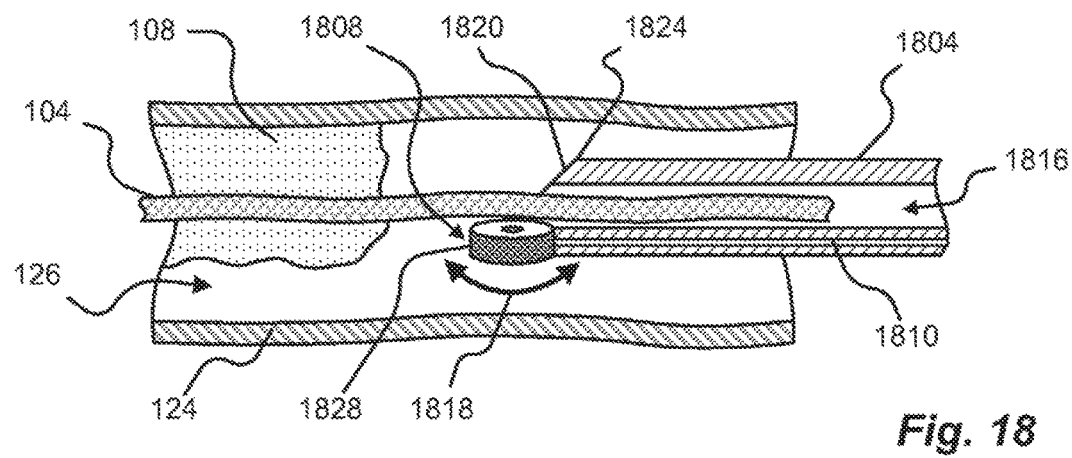
FIG. 18 shows a ninth embodiment of a tissue slitting device inside an area of vasculature having formed tissue surrounding an implanted lead in accordance with embodiments of the present disclosure.

FIG. 18 shows an embodiment of a tissue slitting device 1804 inside an area of vasculature having formed tissue 108 surrounding an implanted lead 104 in accordance with embodiments of the present disclosure. In some embodiments, the tissue slitting device 1804 comprises an inner lumen 1816, at least one grinding wheel 1808 comprising at least one abrasive surface 1828, an actuation element 1810, a tapered section 1820, and a tapered section transition 1824. The inner lumen 1816 may be configured to allow a lead 104 and/or other objects to pass therethrough (e.g., a lead-locking device, traction device, snare tool, etc). As can be appreciated, the tissue slitting device 1804 may be indexed and/or guided along the lead 104 via the inner lumen 1816 of the device 1804.

As shown, the grinding wheel 1808 can move in one or more rotational direction 1818. In some embodiments, the grinding wheel 1808 may rotate continually in one direction, while actuated. For example, the actuation element 1810 may be operatively connected to the at least wheel 1808 to rotate the wheel 1808 about a fixed axis. As the grinding wheel 1808 is rotated it can emaciate tissue it engages at the distal tip of the tissue slitting device 1804. Alternatively, the actuation element 1810 may be an electrical connection to a power source at the proximal end of the tissue slitting device 1804. In this example, the grinding wheel 1808 may include a motor at the distal end that is operatively attached to the grinding wheel 1808 and is powered by a power source connected to the electrical connection.

In other embodiments, the grinding wheel 1808 may repeatedly alternate directions of rotation (e.g., from a clockwise to a counterclockwise direction, and so forth). When the abrasive surface 1828 is actuated and then engaged with a tissue growth 108, the grinding wheel 1808 may cause at least a partial slit in the engaged tissue growth 108 by emaciating contacted tissue growth 108.

Figure 19A:
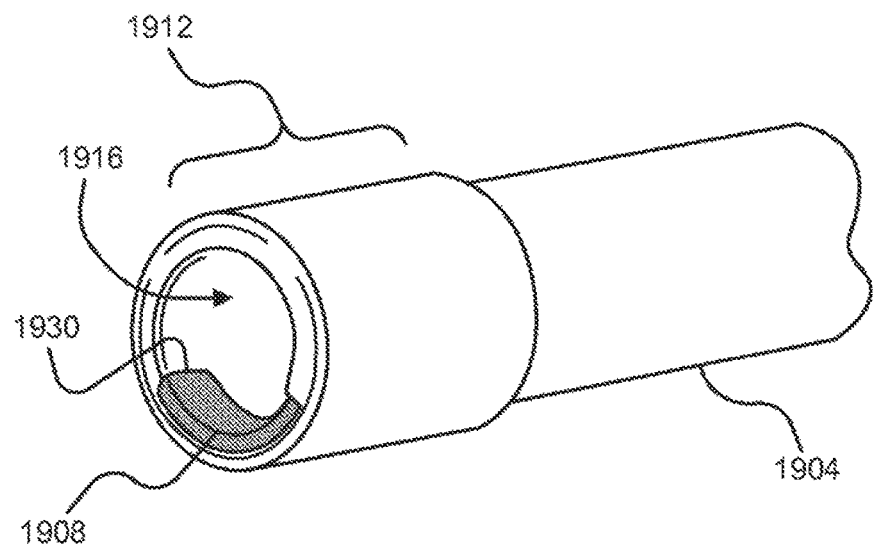
FIG. 19A shows a perspective view of a tenth embodiment of a tissue slitting device in accordance with embodiments of the present disclosure.
Figure 19B:
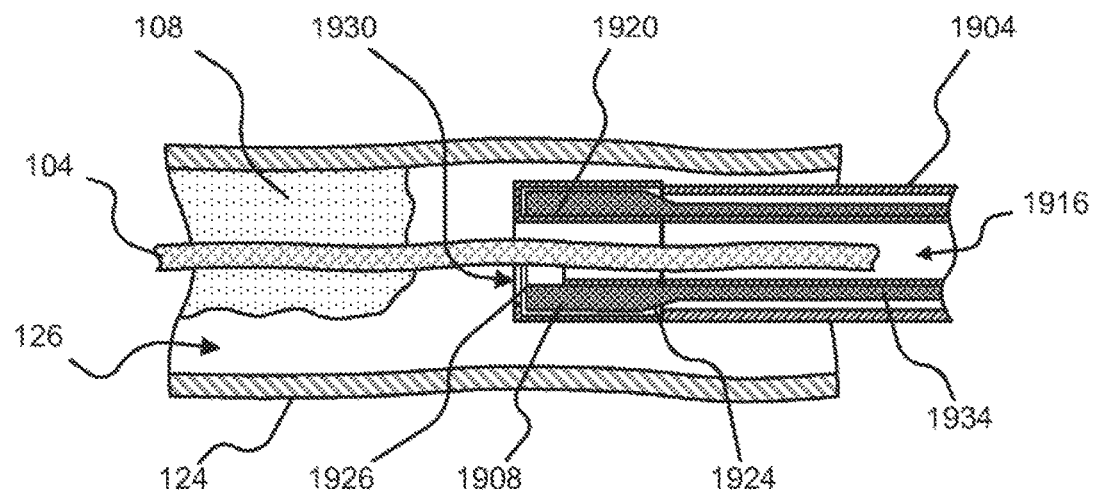
FIG. 19B shows a section view of the tissue slitting device of FIG. 19A.

Referring to FIGS. 19A and 19B, an embodiment of an abrasive tissue slitting device is shown in accordance with embodiments of the present disclosure. In some embodiments, the tissue slitting device 1904 comprises an inner lumen 1916, at least one grinding surface 1908 having an exposed edge 1926 inside a lumen cutout 1930 of the distal tip 1912, a shielded lumen portion 1920, a tapered transition 1924, and a transmission shaft 1934. The inner lumen 1916 may be configured to allow a lead 104 and/or other objects to pass therethrough (e.g., a lead-locking device, traction device, snare tool, etc). As can be appreciated, the tissue slitting device 1904 may be indexed and/or guided along the lead 104 via the inner lumen 1916 of the device 1904.

In some embodiments, the tissue slitting device 1904 provides a rotating grinding surface 1908 to emaciate tissue growth 108 along one side of the lead 104. In other words, the tissue slitting device 1904 includes a cutout 1930 to expose a grinding edge 1926 to the tissue growth 108. It is anticipated that the grinding surface 1908 may be rotated and/or operate similarly to the previously disclosed grinding embodiments. In other words, the grinding surface 1908 may be rotated in one direction continuously and/or periodically, and/or in alternate directions (e.g., clockwise and counterclockwise) continuously and/or periodically.

In one embodiment the grinding surface may be partially covered by a shielded lumen portion 1920. The shielded lumen portion 1920 may prevent contact of the grinding surface with areas of the vasculature, or lead 104, other than a section of the formed tissue 108 surrounding the lead 104. As can be expected, the partial covering may present an exposed section of the grinding surface 1908 to contact the formed tissue that is engaged with the distal tip of the tissue slitting device 1904. In some embodiments, the grinding surface 1908 may be angled, or disposed at an angle, in relation to the distal tip 1912 of the tissue slitting device 1904.

Laser Ablation Embodiments

FIGS. 20-25 show embodiments of a tissue slitting device utilizing laser ablation and one or more light guides that are configured to transmit light to ablate the tissue 108 surrounding at least a portion of the lead 104. It should be noted that the laser ablation embodiments may be used alone or in combination with any of the other embodiments set forth in this disclosure. That is, the laser ablation embodiments may be used in conjunction with the cutting, grinding, planing, high-pressure solution, and other embodiments discussed herein.

Figure 20:
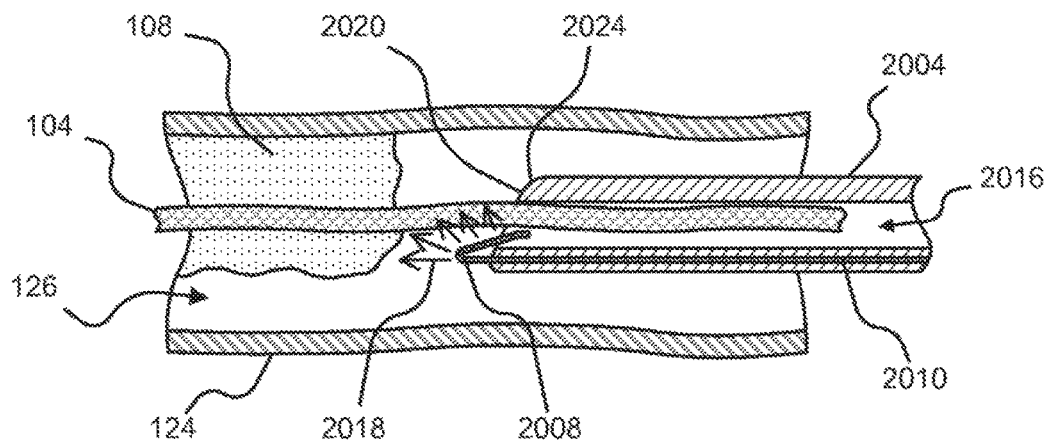
FIG. 20 shows an eleventh embodiment of a tissue slitting device inside an area of vasculature having formed tissue surrounding an implanted lead in accordance with embodiments of the present disclosure.

FIG. 20 shows an embodiment of a tissue slitting device 2004 inside an area of vasculature having formed tissue 108 surrounding an implanted lead 104 in accordance with embodiments of the present disclosure. In some embodiments, the tissue slitting device 2004 comprises an inner lumen 2016, a light-emitting distal end 2008, at least one light guide 2010, a tapered section 2020, and a tapered section transition 2024. The inner lumen 2016 may be configured to allow a lead 104 and/or other objects to pass therethrough (e.g., a lead-locking device, traction device, snare tool, etc). As can be appreciated, the tissue slitting device 2004 may be indexed and/or guided along the lead 104 via the inner lumen 2016 of the device 2004.

The light-emitting distal end 2008 of the tissue slitting device 2004 may comprise one or more terminated light guides 2010. In one embodiment, the one or more terminated light guides 2010 may be optical fibers that can are arranged such that light is directed along a path 2018 toward a tissue growth 108 surrounding an area of a lead 104. It is anticipated that the optical fibers can conduct laser light generated by a laser system located at the proximal end of the tissue slitting device 2004. In some cases, the laser light may be generated in the 308 nM range. Exemplary laser light may include pulsed laser light created by an XeCl Excimer laser system.

In accordance with one aspect of the present disclosure, the wavelength of the laser light conducted by the optical fibers, and/or light guides 2010, as disclosed herein may be adjusted to match a desired ablation energy for various deposits and/or growths inside a patient. As can be appreciated, different deposits and/or growths may require different laser wavelengths for efficient ablation. These deposits may include tissue, fat, collagen, elastin, lipid accumulation, fibrotic layers, plaque, calcified layers, and the like. In one example, the wavelength of the laser system may be selectively tuned using one or more optical components to provide a second laser wavelength. In other words, the one or more optical components may alter a characteristic associated with the light energy emitted by a laser source. Examples of such optical components may include, but are not limited to, one or more filters, lenses, prisms, coatings, films, and deposited layers of optically transmissive material. In another example, a second laser system may be optically coupled with the optical fibers and/or light guides to provide the second laser wavelength. This second laser system and the corresponding second wavelength may be activated in conjunction with the laser system. Alternatively, the second laser system and second laser wavelength may be activated separately from the laser system.

It is an aspect of the present disclosure that the wavelength of the laser light conducted by the optical fibers and/or light guides may be adjusted during an ablation operation. As can be appreciated, an operator may select an appropriate wavelength of laser light as required to ablate various deposits. This selection may be performed without requiring removal of the optical fibers and/or light guides from the patient. In other words, a switch from one laser wavelength to another laser wavelength can be performed outside of the patient at the laser system and/or the second laser system.

In one embodiment, the tissue slitting device 2004 may include features that contact the lead 104 and allow the light-emitting distal end 2008 to accept deviations in lead geometry and location. For instance, the features may include a spring, band, or other elastic member that is operatively connected to an area of the light-emitting distal end 2008. In this example, what the distal end 2008 contacts a change in lead 104 geometry, the tissue growth 108, or other foreign object, the elastic member can accommodate the change and adjust a position and/or orientation of the light-emitting distal end 2008.

In accordance with embodiments of the present disclosure, the tissue slitting device 2004 may configured to cause an ablation of tissue in a given width and/or depth along an axial length of the lead 104. In some instances, the light-emitting distal end 2008 may be configured to cauterize, ablate, or otherwise separate tissue growth 108 along a thin section. For instance, the tissue slitting device 2004 may create an initial separation of tissue as wide as the array of one or more optical fibers. As can be appreciated, the width of the initial tissue separation can be correlated to the arrangement and width of the one or more light guide 2010 of the tissue slitting device 2004.

In another embodiment, the one or more light guide 2010 may direct light at least partially inward toward the central axis of the lead 104. The one or more light guide 2010 may be disposed to conduct at least portion of the light angularly toward the distal end of the tissue slitting device 2004 and/or toward the central axis of the lead 104. As the tissue slitting device 2004 engages the tissue growth 108, the laser light may be activated and the tissue 108 may be severed along the line of conducted light.

Figure 21:
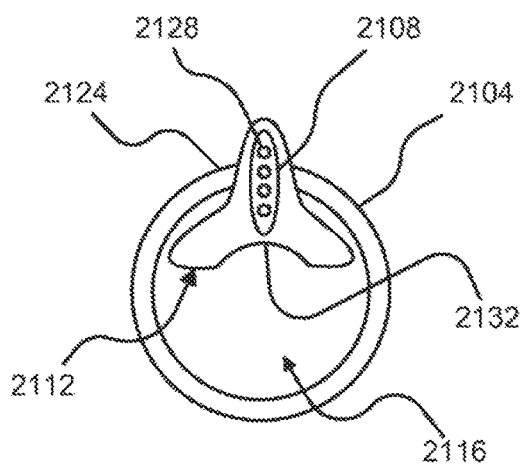
FIG. 21 shows an end view of a twelfth embodiment of a tissue slitting device in accordance with embodiments of the present disclosure.

FIG. 21 shows an embodiment of a tissue slitting device 2104 in accordance with embodiments of the present disclosure. In some embodiments, the tissue slitting device 2104 comprises an inner lumen 2116, a laser member 2112 comprising a light-emitting distal end 2108 at least one light guide 2128 and a lead engagement feature 2132, and a tapered section transition 2124. The inner lumen 2116 may be configured to allow a lead 104 and/or other objects to pass therethrough (e.g., a lead-locking device, traction device, snare tool, etc). As can be appreciated, the tissue slitting device 2104 may be indexed and/or guided along the lead 104 via the inner lumen 2116 of the device 2104.

The laser member 2112 may include one or more features 2132 to engage with an implanted lead 104. One example of such a lead engagement feature 2132 may include an arcuate surface that is disposed on the lead 104 side of the laser member 2112. As can be appreciated, the arcuate surface of the lead engagement feature 2132 may substantially contact the lead 104 at more than one point. This multiple-point contact may provide stability to the tissue slitting device 2104 as it is indexed along the lead 104.

In some cases, a plurality of light guides 2128 may be arranged vertically. As such, the light guides 2128 may direct laser light along a plane that runs along, or parallel to, the lead 104 axis. In other words, the tissue slitting device 2104, when actuated and presented adjacent to a tissue growth 108, may cause a separation of tissue in a tissue growth 108 along an axial length of the growth 108.

Figure 22:
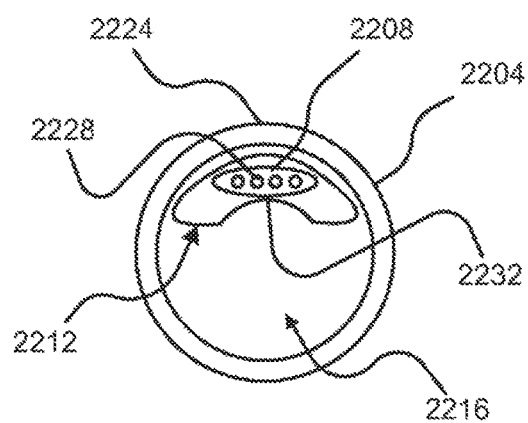
FIG. 22 shows an end view of a thirteenth embodiment, of a tissue slitting device in accordance with embodiments of the present disclosure.

FIG. 22 shows an embodiment of a tissue slitting device 2204 in accordance with embodiments of the present disclosure. In some embodiments, the tissue slitting device 2204 comprises an inner lumen 2216, a laser member 2212 comprising a light-emitting distal end 2208 at least one light guide 2228 and a lead engagement feature 2232, and a tapered section transition 2224. The inner lumen 2216 may be configured to allow a lead 104 and/or other objects to pass therethrough (e.g., a lead-locking device, traction device, snare tool, etc). As can be appreciated, the tissue slitting device 2204 may be indexed and/or guided along the lead 104 via the inner lumen 2216 of the device 2204.

The laser member 2212 may include one or more features 2232 to engage with an implanted lead 104. One example of such a lead engagement feature 2232 may include an arcuate surface that is disposed on the lead 104 side of the laser member 2212. As can be appreciated, the arcuate surface of the lead engagement feature 2232 may substantially contact the lead 104 at more than one point. This multiple-point contact may provide stability to the tissue slitting device 2204 as it is indexed along the lead 104.

In some cases, a plurality of light guides 2228 may be arranged horizontally. As such, the light guides 2228 may direct laser light along a plane that runs along, or parallel to, the outer circumference of the lead 104. In other words, the tissue slitting device 2204, when actuated and presented adjacent to a tissue growth 108, may cause a separation of tissue in a tissue growth 108 along an axial length and width of the growth 108. This separation of tissue is similar to the removal of tissue provided by the embodiment disclosed in FIG. 11.

Figure 23:
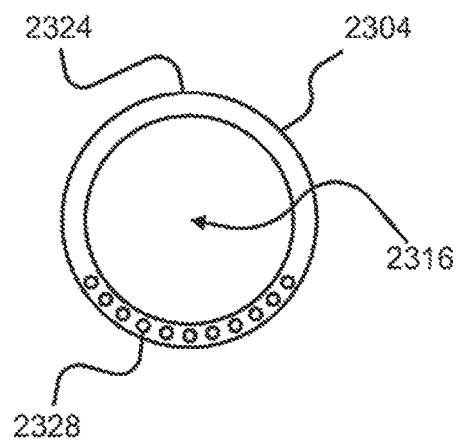
FIG. 23 shows an end view of a fourteenth embodiment of a tissue slitting device in accordance with embodiments of the present disclosure.

FIG. 23 shows a distal end view of a laser tissue slitting device 2304 in accordance with embodiments of the present disclosure. In some embodiments, the tissue slitting device 2304 comprises a shaft 2324, an inner lumen 2316, and a plurality of optical fibers 2328, illustrates a tube having a distal end with optical fibers included therein. The inner lumen 2316 may be configured to allow a lead 104 and/or other objects to pass therethrough (e.g., a lead-locking device, traction device, snare tool, etc). As can be appreciated, the tissue slitting device 2304 may be indexed and/or guided along the lead 104 via the inner lumen 2316 of the device 2304. The optical fibers 2328 may be used to ablate a section of tissue growth 108 surrounding a lead 104. Additionally or alternatively, the optical fibers 2328 may be disposed in a portion of the shaft 2324 or about the entire periphery of the shaft 2324.

Figure 24:
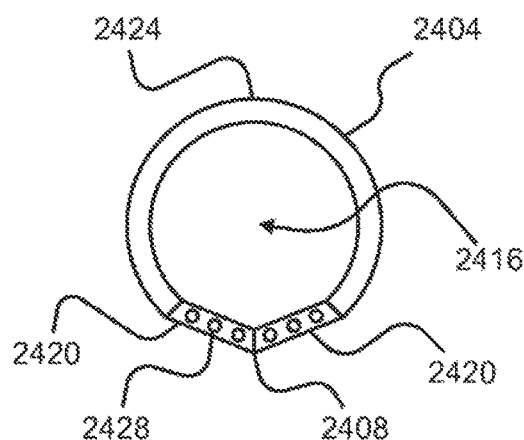
FIG. 24 shows an end view of a fifteenth embodiment of a tissue slitting device in accordance with embodiments of the present disclosure.
Figure 25:
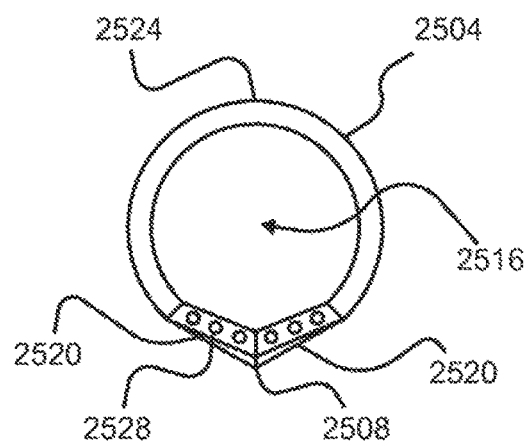
FIG. 25 shows an end view of a sixteenth embodiment of a tissue slitting device in accordance with embodiments of the present disclosure.

FIGS. 24-25 show embodiments where one or more laser ablation features are combined with other tissue slitting embodiments as disclosed or suggested herein.

Referring to FIG. 24, a distal end view of a tissue slitting device 2404 is shown in accordance with embodiments of the present disclosure. In some embodiments, the tissue slitting device 2404 comprises a shaft 2424, an inner lumen 2416, at least one wedge feature 2420, and a plurality of optical fibers 2428. Additionally or alternatively, the tissue slitting device 2404 may include a cutting edge 2408. The inner lumen 2416 may be configured to allow a lead 104 and/or other objects to pass therethrough (e.g., a lead-locking device, traction device, snare tool, etc). As can be appreciated, the tissue slitting device 2404 may be indexed and/or guided along the lead 104 via the inner lumen 2416 of the device 2404. The optical fibers 2428 may be used to ablate a section of tissue growth 108 surrounding a lead 104. The optical fibers 2428 may be disposal in a portion of the shaft 2424 or about the entire periphery of the shaft 2424. In some embodiments, when the optical fibers 2428 are included in only a portion of the shaft 2424, it may be preferable to bias the optical fibers 2428 adjacent to the cutting edge 2408 or cutting tip of the shaft 2424 as shown. Alternatively, it may be preferable to include the optical fibers 2428 at a distance away from the cutting edge 2408 or cutting tip of the shaft 2424. In some embodiments, it may be preferable to include as many optical fibers 2428 as possible within the circumference of the shaft 2424.

FIG. 25 shows a distal end view of a tissue slitting device 2504 in accordance with embodiments of the present disclosure. In some embodiments, the tissue slitting device 2504 comprises a shaft 2524, an inner lumen 2516, at least, one cutting wedge feature 2520, and a plurality of optical fibers 2528. Additionally or alternatively, the tissue slitting device 2504 may include a distal cutting edge 2508. The inner lumen 2516 may be configured to allow a lead 104 and/or other objects to pass therethrough (e.g., a lead-locking device, traction device, snare tool, etc). As can be appreciated, the tissue slitting device 2504 may be indexed and/or guided along the lead 104 via the inner lumen 2516 of the device 2504. The optical fibers 2528 may be used to ablate a section of tissue growth 108 surrounding a lead 104. The optical fibers 2528 may be disposed in a portion of the shaft 2524 or about the entire periphery of the shaft 2524. In some embodiments, when the optical fibers 2528 are included in only a portion of the shaft 2524, it may be preferable to bias the optical fibers 2528 adjacent to the distal cutting edge 2508 or cutting tip of the shaft 2524 as shown. Alternatively, it may be preferable to include the optical fibers 2528 at a distance away from the cutting edge 2508 or cutting tip of the shaft 2524. In some embodiments, it may be preferable to include as many optical fibers 2528 as possible within the circumference of the shaft 2524.

Additionally or alternatively, the tissue slitting edge may utilize other wavelengths of emitted radiation energy, such as thermal or infrared energy, electromagnetic radiation, and/or other radiation wavelengths to slit or cut the formed tissue. The tissue slitting edge can, for example, be an energy device, such as a power sheath (of a catheter), which typically applies a form of energy at the sheath tip to cut the scar tissue away from the lead thus allowing for removal. As the sheath is pushed over the lead and comes to an area of attachment, the operator can turn on the sheath's energy source to heat or vaporize scar tissue, forming the desired slit. One such sheath uses electrocautery, similar to what is used to cut through tissue in surgery. Another sheath has one or more tiny energy emitters at its lip or edge. When activated, the emitted energy vaporizes water molecules in scar tissue within about 1 mm, thereby forming the desired slit or cut. Additionally or alternatively, dilating telescopic sheaths or cutting balloons of a catheter having a longitudinally positioned tissue slitting edge can be fully or partially expanded or inflated, thereby deploying the tissue slitting edge to form the desired slit.

In some embodiments, the distal tip of the tissue slitting device 2504 may include a wedge cutting feature 2520. The wedge cutting feature 2520 may comprise a blade and a wedge configured to peel the tissue away from the cutting edge 2508 of the tissue slitting device 2504 as it is being cut by the cutting edge 2508 and the blade. Utilizing a combination of laser ablation embodiments with other tissue slitting embodiments allows for creative solutions to various tissue growths 108. For example, the laser light in a laser tissue slitting device 2504 may be actuated in pulses to ablate sections of difficult tissue growth 108 while the wedge cutting feature 2520 acts to cut and separate ablated and other areas of the tissue growth 108. As can be appreciated, various laser embodiments and/or actuation techniques and other tissue slitting features may be combined to best suit individual tissue growth 108 in a patient 102.

It should be noted that the laser ablation embodiments, as well as the other embodiments disclosed herein, may be used alone or in combination with the non-traumatic leading edge, wedges, tapers, and/or other tissue slitting embodiments disclosed without limitation. Additionally or alternatively, the tissue slitting devices disclosed herein may include at least one fluorescing material or marker (e.g., radiopaque band, marker, and the like). In some embodiments, the radiopaque marker may be arranged about and/or adjacent to a tissue cutting area (e.g., laser optical fibers, blades, planers, electromagnetic radiation emitter, RF devices, high-pressure fluid, grinders, sanders, drills, ultrasonic devices, and the like) of the tissue slitting device. The radiopaque marker, may assist in identifying a location of the tissue cutting area via a monitoring device. Examples of radiopaque markers may include, but are in no way limited to, materials and/or particles containing tantalum, tungsten, carbide, iridium, bismuth oxide, barium sulfate, cobalt, platinum and/or alloys and combinations thereof.

High-Pressure Solution Embodiments

Figure 26:
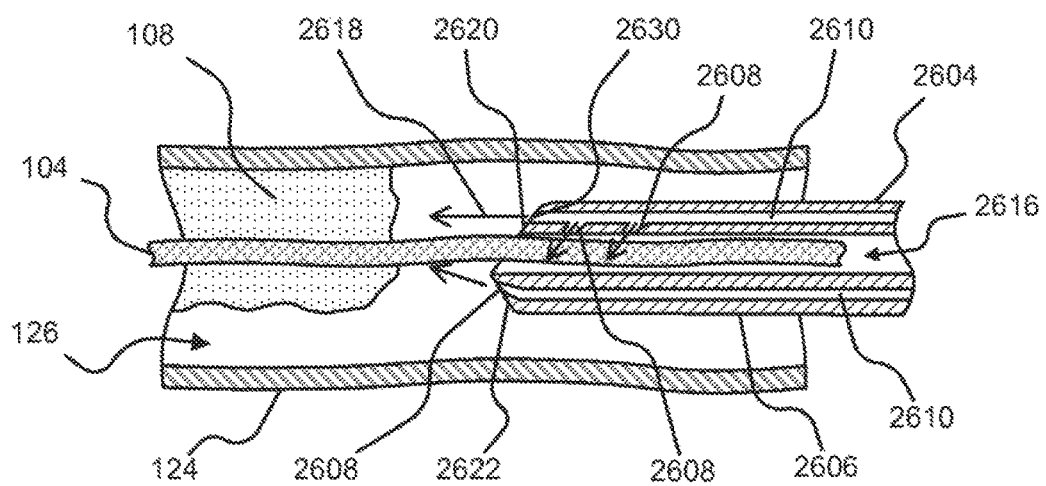
FIG. 26 shows a seventeenth embodiment of a tissue slitting device inside an area of vasculature having formed tissue surrounding an implanted lead in accordance with embodiments of the present disclosure.

FIG. 26 shows a tissue slitting device 2604 inside an area of vasculature having tissue growth 108 surrounding an implanted lead 104 in accordance with embodiments of the present disclosure. In some embodiments, the tissue slitting device 2604 comprises a shaft 2606, an inner lumen 2616, at least one fluid channel 2610, at least one nozzle 2608, a tissue-side taper 2620, and an opening-side taper 2608. Additionally or alternatively, the tissue slitting device 2604 may include a port opening 2630. The inner lumen 2616 may be configured to allow a lead 104 and/or other objects to pass therethrough (e.g., a lead-locking device, traction device, snare tool, etc). As can be appreciated, the tissue slitting device 2604 may be indexed and/or guided along the lead 104 via the inner lumen 2616 of the device 2604. Embodiments of the present disclosure anticipate using a solution (e.g., NaCl, MgCl, saline, etc.) directed under pressure to remove formed tissue 108 attached to an implanted lead 104. A fluid channel 2610 having a proximal end, a distal end, and an inner lumen running from the proximal end of the fluid channel 2610 to an area of the distal end of the tissue slitting device 2604, may be disposed substantially parallel to the shaft 2606 to contain the pressurized solution (e.g., NaCl, saline, etc.).

In some embodiments, the channel 2610 may taper in the form of a nozzle 2608 at the distal end to focus fluid expelled from the channel 2610. As can be appreciated, the focus of the fluid out of the nozzle 2608 increases the pressure of the fluid that contacts a tissue growth 108. Alternatively, a fluid channel 2610 may include a port opening 2630 that does not include any taper. As such, the fluid is not focused as it is expelled from the fluid port opening 2630. In some embodiments, the channel 2610 may include a plurality of orifices configured to expel saline solution. This plurality of orifices may include one or more nozzle 2608 features to control the rate of flow of the saline solution. Additionally or alternatively, the at least one orifice may be directed toward the lead 104, formed tissue 108, or other object and/or obstruction. In one embodiment, a first orifice may be oriented at a first angle to the lead 104 and/or formed tissue 108, and a second orifice may be oriented at a second angle to the lead 104 and/or formed tissue 108. In another embodiment, the angle and/or shape of the nozzle 2608, opening 2630, or orifices may be affected by the angle of the tissue-side taper 2620 and/or the opening-side taper 2608. Among other things, the orifices may be used to clear obstructions, clean the lead 104 as the tissue slitting device 2604 is moved along the lead 104, and/or provide lubrication for the inner lumen 2616 of tissue slitting device 2604 as it is moved along a lead 104.

Additionally or alternatively, solution may be forced between the tissue growth 108 and the lead 104 via at least one channel 2610 associated with the tissue slitting device 2604. The forced solution may act to expand and/or dilate the tissue growth 108 formed around a lead 104 or object. In some embodiments, the dilation of the formed tissue 108 created by the solution may create an opening for insertion of the distal end of the tissue slitting device 2604.

As can be appreciated, use of the forced solution may be combined with any other device and/or method disclosed herein. In one embodiment, the forced solution may cause the formed tissue 108 to expand around the lead 104 such that the formed tissue 108 no longer applies any forces to the lead 104. In such cases, the lead 104 may be removed from the formed tissue 108 while it is dilated.

Figure 27:
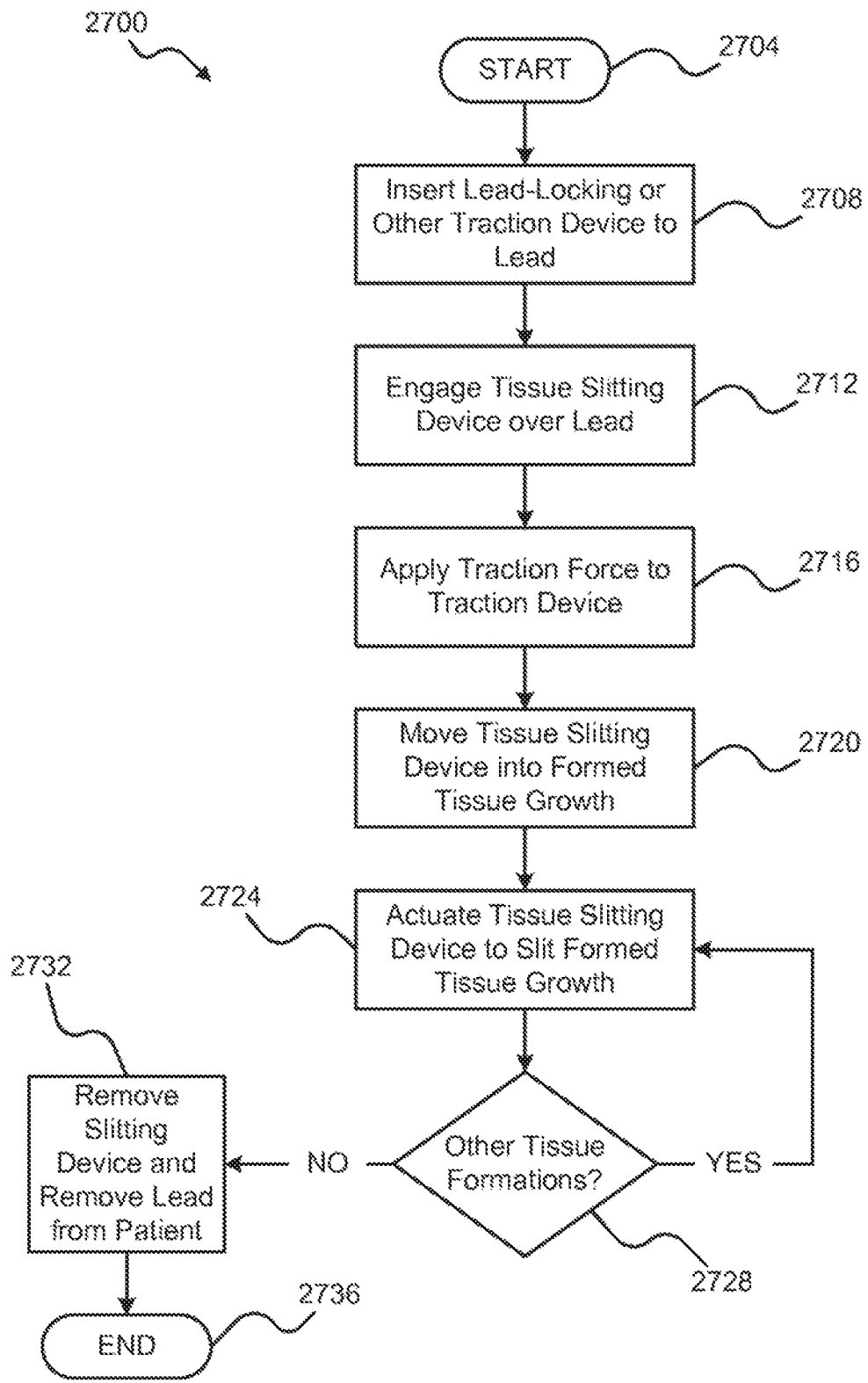
FIG. 27 is a flow diagram depicting a tissue slitting method in accordance with embodiments of the present disclosure.

Referring to FIG. 27, a tissue slitting method 2700 will be described in accordance with at least some embodiments of the present disclosure. The method 2700 starts at 2704 and begins by connecting a lead-locking device or other traction device to the lead 104 (step 2708). In some embodiments, the lead-locking device may be inserted into the core of an implanted lead 104. In other embodiments, a traction device may be connected to the lead 104 to provide traction on the lead 104. For instance, mechanical traction can be achieved in leads 104 by inserting a locking stylet into the lead 104 and applying a pull force onto the lead 104 via the locking stylet.

Once a traction device is attached to the lead 104, the traction device can be threaded through the internal, or inner, lumen of the tissue slitting device (step 2712). For example, the lead-locking device may be inserted through the lumen in an implanted lead 104 and attached to the internal portions of the implanted lead 104, which can be at the distal portion or proximal to the distal portion of the lead 104. The tissue slitting device may be part of a catheter that rides over the external portion of the lead 104 and lead-locking device and is configured to remove tissue along an axial length of the tissue 108 in contact with the lead 104.

As the tissue slitting device is engaged with the lead 104, a slight traction force may be applied to the lead 104 to allow the tissue slitting device to guide along the lead 104 (step 2716). The tissue slitting device can be moved toward the first formed tissue growth while applying a mechanical traction force to the lead 104 itself or through a locking stylet, or other traction device. Mechanical traction force should be applied with appropriate force to prevent tearing the vein or artery wall by moving the lead 104 and tissue before they are separated. In some embodiments, the tissue slitting device may be observed moving inside a patient 102 via a fluoroscope or other monitor. It is anticipated that the distal tip, or some other area, of the tissue slitting device may include a fluorescing material or marker (e.g., radiopaque band, and the like). This fluorescing material or marker may be used to aid in monitoring the movement of the tissue slitting device when it is inside a patient.

Next, the tissue slitter is moved into contact with the formed tissue growth (step 2720). In some embodiments, the slitting portion of the tissue slitting device may be oriented toward the center of the vein, or away from the vein wall connecting the lead 104 to the vein. In addition to preventing accidental puncture, trauma, or other damage to the delicate surfaces of the vasculature this orientation of the tissue slitting device may aid in the slitting and peeling away of the tissue 108 from the implanted lead 104. For example, a tissue slitting device may include a distal tip with a wedge and/or tapered portion proximal to the sharp portion of the tissue slitting device. It is anticipated that the distal tip of the tissue slitting device may include a non-traumatic leading edge. In some cases, the non-traumatic leading edge and the tapered portion may comprise the distal tip of the tissue slitting device. While applying mechanical traction force, the leading portion (of the tissue slitting device) may include a sharp, cutting, ablating, or grinding portion, which may be configured to cut into the tissue growth 108. As the tissue slitting device traverses along the lead 104, the cutting portion of the tissue slitting device continues to separate the formed tissue 108. Additionally the leading portion, which may include a wedge and/or tapered portion, can act to cause a stretching of the formed tissue growth 108 at the point where it engages with the tissue slitting device. This stretching of tissue may assist in the slitting operation by causing tension on the fibers of the tissue growth 108 that, when slit, pull back (or away) from the tissue slitting device engagement area.

Once the tissue slitting device is engaged with, and/or slitting, the formed tissue, the tissue slitting device may be actuated and moved along the lead to further engage with the tissue growth 108 (step 2724). In some embodiments, the tissue slitting device may be indexed forward (into the tissue formation 108) continuously or periodically. In other embodiments, the tissue slitting device may be repeatedly indexed into and removed from the engagement area of the formed tissue growth 108. It is anticipated that each time the tissue slitting device is indexed into the engagement area the device can make a successively longer slit in the formed tissue 108.

The method 2700 may be continued by determining whether other tissue growths exist, and if so, indexing the tissue slitting device through each formed tissue growth 108 that is surrounding a section of the implanted lead 104 in the vasculature (step 2728).

Once all of the formed tissue growths 108 are slit, the tissue slitting device may be removed from the patient 102 (step 2732). Additionally or alternatively, once the slits have been made the lead 104 may be removed by applying a pull force to the lead-locking device in the same direction as the mechanical traction force previously applied to the lead 104. It is anticipated that any movement of the tissue slitting device may be accompanied by an applied mechanical traction force to the lead/lead-locking device. The method 2700 ends at step 2736.

Other Embodiments

Figure 28:
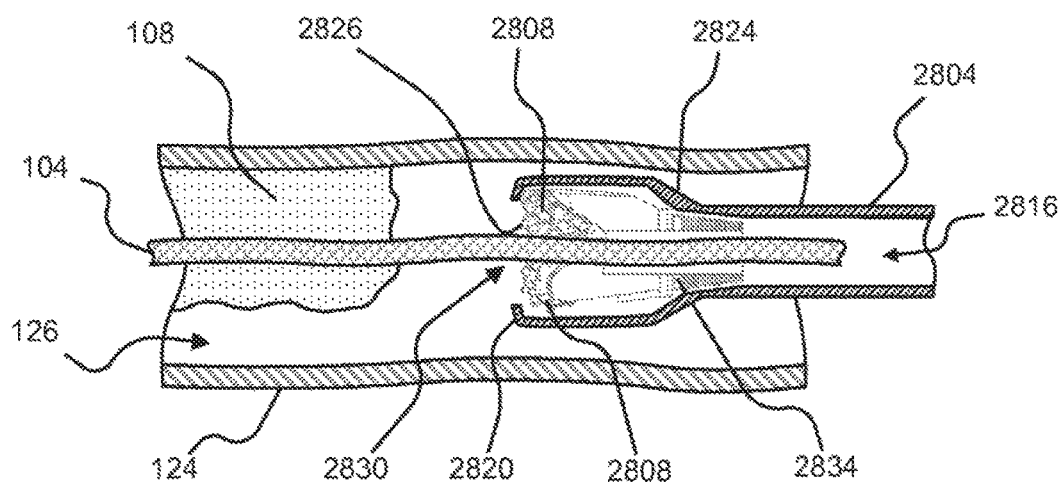
FIG. 28 shows an embodiment of a grinding tissue slitting device inside an area of vasculature having formed tissue surrounding an implanted lead in accordance with embodiments of the present disclosure.

Referring to FIG. 28, an embodiment of an abrasive tissue slitting device is shown in accordance with embodiments of the present disclosure. In some embodiments, the tissue slitting device 2804 comprises an inner lumen 2816, at least one grinding surface 2808 having an exposed portion 2826 at least partially surrounded by a distal tip shield 2820, a tapered transition 2824, and a transmission shaft 2834. The inner lumen 2816 may be configured to allow a lead 104 and/or other objects to pass therethrough (e.g., a lead-locking device, traction device, snare tool, etc). As can be appreciated, the tissue slitting device 2804 may be indexed and/or guided along the lead 104 via the inner lumen 2816 of the device 2804.

In some embodiments, the tissue slitting device 2804 provides one or more rotating grinding surface 2808 to emaciate tissue growth 108 along at least one side of the lead 104. In other words, the tissue slitting device 2804 includes at least one opening 2830 to expose a grinding edge 2826 to the tissue growth 108. It is anticipated that the grinding surface 2808 may be rotated and/or operate similarly to the previously disclosed grinding embodiments. In other words, the grinding surface 2808 may be rotated in one direction continuously and/or periodically, and/or in alternate directions (e.g., clockwise and counterclockwise) continuously and/or periodically. As can be appreciated, the tissue slitting device 2804 may include one or more grinding surfaces 2808 that can be linked and/or geared together. For example, in instances where the tissue slitting device 2804 includes two or more grinding surfaces 2808, the two or more grinding surfaces may be geared to operate simultaneously. Additionally, the grinding surfaces may be directly geared and/or indirectly geared to rotate/move in alternate and/or similar rotational directions, respectively.

In one embodiment, the grinding surface 2808 may be partially covered by a shielded portion 2820. The shielded portion 2820 may prevent contact of the grinding surface with areas of the vasculature, or lead 104, other than a section of the formed tissue 108 surrounding the lead 104. As can be expected, the partial covering may present an exposed section of the grinding surface 2808 to contact the formed tissue that is engaged with the distal tip of the tissue slitting device 2804. In some embodiments, the grinding surface 2808 may be angled, or disposed at an angle, in relation to the distal tip of the tissue slitting device 2804.

In the appended figures, similar components and/or features may have the same reference label. Further, various components of the same type may be distinguished by following the reference label by a letter that distinguishes among the similar components. If only the first reference label is used in the specification, the description is applicable to any one of the similar components having the same first reference label irrespective of the second reference label.

Presented herein are embodiments of a tissue separating device, system, and method. As described herein, the device(s) may be electrical, mechanical, electro-mechanical, and/or combinations thereof.

Also, while the flowcharts have been discussed and illustrated in relation to a particular sequence of events, it should be appreciated that changes, additions, and omissions to this sequence can occur without materially affecting the operation of the disclosed embodiments, configuration, and aspects.

A number of variations and modifications of the disclosure can be used. It would be possible to provide for some features of the disclosure without providing others. By way of illustration, any methodology or modality of cutting tissue may be employed as described herein to effect lead removal from an encased tissue growth.

The present disclosure, in various aspects, embodiments, and/or configurations, includes components, methods, processes, systems and/or apparatus substantially as depicted and described herein, including various aspects, embodiments, configurations embodiments, subcombinations, and/or subsets thereof. Those of skill in the art will understand how to make and use the disclosed aspects, embodiments, and/or configurations after understanding the present disclosure. The present disclosure, in various aspects, embodiments, and/or configurations, includes providing devices and processes in the absence of items not depicted and/or described herein or in various aspects, embodiments, and/or configurations hereof, including in the absence of such items as may have been used in previous devices or processes, e.g., for improving performance, achieving ease and/or reducing cost of implementation.

The foregoing discussion has been presented for purposes of illustration and description. The foregoing is not intended to limit the disclosure to the form or forms disclosed herein. In the foregoing Summary for example, various features of the disclosure are grouped together in one or more aspects, embodiments, and/or configurations for the purpose of streamlining the disclosure. The features of the aspects, embodiments, and/or configurations of the disclosure may be combined in alternate aspects, embodiments, and/or configurations other than those discussed above. This method of disclosure is not to be interpreted as reflecting an intention that the claims require more features than are expressly recited in each claim. Rather, as the following claims reflect, inventive aspects lie in less than all features of a single foregoing disclosed aspect, embodiment, and/or configuration. Thus, the following claims are hereby incorporated into this Summary, with each claim standing on its own as a separate preferred embodiment of the disclosure.

Moreover, though the description has included description of one or more aspects, embodiments, and/or configurations and certain variations and modifications, other variations, combinations, and modifications are within the scope of the disclosure, e.g., as may be within the skill and knowledge of those in the art, after understanding the present disclosure. It is intended to obtain, rights which include alternative aspects, embodiments, and/or configurations to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A tissue slitting apparatus comprising:
a shaft, wherein the shaft is flexible, the shaft having a proximal end and a distal end, wherein the distal end comprises an opening and a circumference, wherein the circumference has a perimeter completely surrounding the opening, and wherein the shaft includes an inner lumen extending proximally from the opening to receive at least one of an implanted object and a mechanical traction device, the inner lumen defining a longitudinal axis of the shaft;
a tissue abrading device disposed adjacent to the opening, the tissue abrading device comprising:
a leading edge disposed at a distal portion of the tissue abrading device; and
an abrading tip, wherein the abrading tip is disposed adjacent to the leading edge, wherein the abrading tip includes at least one reciprocating grinder, the at least one reciprocating grinder having at least one abrasive surface, wherein the at least one reciprocating grinder is configured to be operatively coupled with an actuator, wherein the at least one reciprocating grinder is configured to reciprocate in a direction relative to the shaft via an actuation force provided by the actuator, and wherein the at least one reciprocating grinder only reciprocates along a portion of the perimeter of the circumference.

2. The tissue slitting apparatus of claim 1, wherein the abrasive surface is manufactured from a material with at least one of a rough surface, knurl, machined surface, formed surface, and diamond deposition surface.

3. The tissue slitting apparatus of claim 2, wherein the material is made of metal.

4. The tissue slitting apparatus of claim 2, wherein the material is made of plastic.

5. The tissue slitting apparatus of claim 1, wherein the abrading tip is configured to move relative to the leading edge from a first position to a second position as the tissue abrading device contacts the tissue growth.

6. The tissue slitting apparatus of claim 1, wherein the at least one reciprocating grinder moves axially relative to the shaft.

7. The tissue slitting apparatus of claim 1, wherein the actuator is powered by an electric motor.

8. The tissue slitting apparatus of claim 1, wherein the actuator is powered by a pneumatic motor.

9. The tissue slitting apparatus of claim 1, wherein the actuator is powered by a hydraulic motor.

10. The tissue slitting apparatus of claim 1, wherein the at least one reciprocating grinder moves across the abrading tip.

11. The tissue slitting apparatus of claim 1, wherein the at least one reciprocating grinder moves axially relative to the shaft and independently of movement of the shaft.

12. The tissue slitting apparatus of claim 1, wherein the at least one reciprocating grinder reciprocates along about 50% or less of the perimeter of the circumference.

13. The tissue slitting apparatus of claim 1, wherein the at least one reciprocating grinder reciprocates along less than 50% of the perimeter of the circumference.

* * * * *